US009434985B2

(12) United States Patent
Dekker et al.

(10) Patent No.: US 9,434,985 B2
(45) Date of Patent: Sep. 6, 2016

(54) METHODS OF IDENTIFYING INTERACTIONS BETWEEN GENOMIC LOCI

(75) Inventors: Job Dekker, Princeton, MA (US); Erez Lieberman, Cambridge, MA (US); Nynke Van Berkum, The Hague (NL); Andreas Gnirke, Wellesley, MA (US); Eric Lander, Cambridge, MA (US); Chad Nusbaum, Nowtoa, MA (US); Louise Williams, Reading, MA (US); Alexandre Melnikov, Bellingham, MA (US); Georgia Giannoukos, Cambridge, MA (US)

(73) Assignees: University of Massachusetts, Boston, MA (US); Massachusetts Institute Of Technology, Cambridge, MA (US); President And Fellows Of Harvard College, Cambridge, MA (US); Whitehead Institute For Biomedical Research, Cambridge, MA (US)

( * ) Notice: Subject to any disclaimer, the term of this patent is extended or adjusted under 35 U.S.C. 154(b) by 211 days.

(21) Appl. No.: 13/121,158

(22) PCT Filed: Sep. 22, 2009

(86) PCT No.: PCT/US2009/005249
§ 371 (c)(1),
(2), (4) Date: Mar. 29, 2012

(87) PCT Pub. No.: WO2010/036323
PCT Pub. Date: Apr. 1, 2010

(65) Prior Publication Data
US 2013/0096009 A1    Apr. 18, 2013

Related U.S. Application Data

(60) Provisional application No. 61/100,151, filed on Sep. 25, 2008.

(51) Int. Cl.
C12Q 1/68         (2006.01)

(52) U.S. Cl.
CPC ............... *C12Q 1/6837* (2013.01); *C12Q 1/68* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | 435/7.9 |
| 3,850,752 A | 11/1974 | Schuurs et al. | 435/7.93 |
| 3,939,350 A | 2/1976 | Kronick et al. | 250/365 |
| 3,996,345 A | 12/1976 | Ullman et al. | 436/537 |
| 4,275,149 A | 6/1981 | Litman et al. | 435/7.91 |
| 4,277,437 A | 7/1981 | Maggio | 422/401 |
| 4,366,241 A | 12/1982 | Tom et al. | 435/7.91 |
| 2007/0231817 A1 | 10/2007 | De Laat et al. | 435/5 |
| 2007/0238101 A1* | 10/2007 | Ruan et al. | 435/6 |
| 2009/0191598 A1 | 7/2009 | Ruan et al. | 435/91.52 |

OTHER PUBLICATIONS

Dotsie et al., Genome Research, 2006, vol. 16, pp. 1299-1309.*
Burns et al., J Clin Pathol, 1985, vol. 38, pp. 1085-92.*
Holland et al., PNAS, 1991, vol. 88, pp. 7276-80.*
Dekker et al., Science, 2002, vol. 295, pp. 1306-1311.*
Dekker, Trends in Biochemical Sciences, 2003, vol. 28, p. 277-280.*
Allison et al., Fundamental Molecular Biology, 2007, Blackwell Publishing, Chapter 8.*
Ahmad, et al., "The genetic basis for cardiac remodeling." Annu Rev Genomics Hum Genet., 6:185-216 (2005).
Bacolla, et al., "The involvement of non-B DNA structures in gross chromosomal rearrangements." DNA Repair (Amst)., 5:1161-1170 (2006).
Bagby, et al., "Fanconi anemia." Semin Hematol. 43:147-156 (2006).
Bell, et al., "Insulators and Boundaries: Versatile Regulatory Elements in the Eukaryotic Genome." Science, 291:447 (2001).
Bernstein, et al., "Genomic Maps and Comparative Analysis of Histone Modifications in Human and Mouse." Cell, 120:169 (2005).
Bindoff, et al., "The genetic basis of muscle disease." Tidsskr Nor Laegeforen., 123:2588-2592 (2003).
Blackwood, et al., "Going the Distance: A Current View of Enhancer Action." Science, 281:60 (1998).
Boyle, et al.,"The spatial organization of human chromosomes within the nuclei of normal and emerin-mutant cells." Hum Mol Genet., 10:211 (2001).
Briese, et al., "Is spinal muscular atrophy the result of defects in motor neuron processes?" Bioessays, 27:946-957 (2005).
Brown, et al., "Association between active genes occurs at nuclear speckles and is modulated by chromatin environment." J Cell Biol., 182:1083 (2008).
Bruneau, "The developmental genetics of congenital heart disease." Nature, 451:943-948 (2008).
Burt, et al., "Genetic testing for inherited colon cancer." Gastroenterolog; 128: 1696-1716 (2005).
Caforio, et al., "Genetically determined myocarditis: clinical presentation and immunological characteristics." Curr Opin Cardiol., 23:219-226 (2008).
Castro, et al., "The complex immunogenetic basis of systemic lupus erythematosus." Autoimmun Rev., 7:345-351 (2008).
Cockett, et al., "The callipyge mutation and other genes that affect muscle hypertrophy in sheep." Genet Sel Evol., 37 Suppl 1 :S65-S81 (2005).

(Continued)

Primary Examiner — Anne Gussow
Assistant Examiner — Mindy G Brown
(74) Attorney, Agent, or Firm — Medlen & Carroll, LLP

(57) ABSTRACT

The disclosed Hi-C protocol can identify genomic loci that are spatially co-located in vivo. These spatial co-locations may include, but are not limited to, intrachromosomal interactions and/or interchromosomal interactions. Hi-C techniques may be applied to many different scales of interest. For example, on a large scale, Hi-C techniques can be used to identify long-range interactions between distant genomic loci.

18 Claims, 55 Drawing Sheets

(56) References Cited

OTHER PUBLICATIONS

Cremer, et al., "Chromosome territories, nuclear architecture and gene regulation in mammalian cells." Nat Rev Genet., 2:292 (2001).
Croft, et al.,"Differences in the Localization and Morphology of Chromosomes in the Human Nucleus." J Cell Biol., 145:1119 (1999).
Dekker, et al., "Capturing chromosome conformation." Science 295:1306-1311 (2002).
Dekker, et al., "Capturing chromosome conformation." Science 295:1306-1311 Supplementary Material (2002).
Dekker, "Gene regulation in the third dimension." Scienc,e 319:1793 (2008a).
Dekker, "Mapping in vivo chromatin interactions in yeast suggests an extended chromatin fiber with regional variation in compaction." J Biol., Chem., 283:34532 (2008b).
Dernburg, et al., "Perturbation of nuclear architecture by long-distance chromosome interactions." Cell, 85:745 (1996).
Dostie, et al., "Chromosome Conformation Capture Carbon Copy (5C): A massively parallel solution for mapping interactions between genomic elements." Genome Research, 16:1299-1309 (2006).
Dostie, et al., "Chromosome Conformation Capture Carbon Copy (5C): A massively parallel solution for mapping interactions between genomic elements." Genome Research, 16:1299-1309 Supplemental Materials Document (2006).
Dostie, et al., "Chromosome Conformation Capture Carbon Copy (5C): A massively parallel solution for mapping interactions between genomic elements." Genome Research, 16:1299-1309 Supp Table 1 (2006).
Dostie, et al., "Chromosome Conformation Capture Carbon Copy (5C): A massively parallel solution for mapping interactions between genomic elements." Genome Research, 16:1299-1309 Supp Table 2 (2006).
Dostie, et al., "Chromosome Conformation Capture Carbon Copy (5C): A massively parallel solution for mapping interactions between genomic elements." Genome Research, 16:1299-1309 Supp Table 3 (2006).
Dostie, et al., "Chromosome Conformation Capture Carbon Copy (5C): A massively parallel solution for mapping interactions between genomic elements." Genome Research, 16:1299-1309 Supp Table 4 (2006).
Dostie, et al., "Chromosome Conformation Capture Carbon Copy (5C): A massively parallel solution for mapping interactions between genomic elements." Genome Research, 16:1299-1309 Supp Table 5 (2006).
Dostie, et al., "Chromosome Conformation Capture Carbon Copy (5C): A massively parallel solution for mapping interactions between genomic elements." Genome Research, 16:1299-1309 Supp Table 6 (2006).
Dostie, et al., "Chromosome Conformation Capture Carbon Copy (5C): A massively parallel solution for mapping interactions between genomic elements." Genome Research, 16:1299-1309 Supp Table 7 (2006).
Dostie, et al., "Chromosome Conformation Capture Carbon Copy (5C): A massively parallel solution for mapping interactions between genomic elements." Genome Research, 16:1299-1309 Supp Table 8 (2006).
Dostie, et al., "Chromosome Conformation Capture Carbon Copy (5C): A massively parallel solution for mapping interactions between genomic elements." Genome Research, 16:1299-1309 Supp Fig. 1 (2006).
Dostie, et al., "Chromosome Conformation Capture Carbon Copy (5C): A massively parallel solution for mapping interactions between genomic elements." Genome Research, 16:1299-1309 Supp Fig. 2 (2006).
Dostie, et al., "Chromosome Conformation Capture Carbon Copy (5C): A massively parallel solution for mapping interactions between genomic elements." Genome Research, 16:1299-1309 Supp Fig. 3 (2006).
Dostie, et al., "Chromosome Conformation Capture Carbon Copy (5C): A massively parallel solution for mapping interactions between genomic elements." Genome Research, 16:1299-1309 Supp Fig. 4 (2006).
Dostie, et al., "Chromosome Conformation Capture Carbon Copy (5C): A massively parallel solution for mapping interactions between genomic elements." Genome Research, 16:1299-1309 Supp Fig. 5 (2006).
Dostie, et al., "Chromosome Conformation Capture Carbon Copy (5C): A massively parallel solution for mapping interactions between genomic elements." Genome Research, 16:1299-1309 Supp Fig. 6 (2006).
Elkharwily, et al., "The pancreas in familial adenomatous polyposis." J Pancreas, 9:9-18 (2008).
Fouchier, et al., "Management of hereditary dyslipidaemia; the paradigm of autosomal dominant hypercholesterolaemia." Eur J Hum Genet., 1 3:1247-1253 (2005).
Fraser, et al., Review Article, "Nuclear organization of the genome and the potential for gene regulation." Nature 447:413 (2007).
Freeman, et al., "Development of minimal residual disease-directed therapy in acute myeloid leukemia." Semin Oncol. ,35:388-400 (2008).
Gammon, et al., "Can we identify the high-risk patients to be screened? A genetic approach." Digestion, 76:7-19 (2007).
Ganguly, "Association studies of lung function in mice." Dtsch Tierarztl Wochenschr., 115:276-284.(2008).
Goodeve, "Genetics of type 1 von Willebrand disease." Curr Opin Hematol., 14:444-449 (2007).
Grosberg, et al., "The role of topological constraints in the kinetics of collapse of macromolecules." J. Phys. France, 49:2095 (1988).
Grosberg, et al., "Crumpled Globule Model of the Three-Dimensional Structure of DNA." Europhysics Letters, 373 (1993).
Haber, et al., "Alpha 1 antitrypsin phenotypes and alcoholic pancreatitis." Gut. 32:945-948 (1991).
Hesselberth, et al., "Global mapping of protein-DNA interactions in vivo by digital genomic footprinting." Nat Methods, 6:283 (2009).
Kibbey, et al., "Molecular Property eXplorer: a novel approach to visualizing SAR using tree-maps and heatmaps." J Chem Inf Model, 45:523-32 (2005).
Kilpivaara, et al., "JAK2 and MPL mutations in myeloproliferative neoplasms." Acta Haematol., 119:218-225 (2008).
Knowles, et al., "Mild cystic fibrosis in a consanguineous family." Ann Intern Med., 1 10:599-605 (1989).
Kolesov, et al., "Protein knot server: detection of knots in protein structures ." Nucleic Acids Res., 35:W425 (2007).
Kosak, et al., "Form follows function: the genomic organization of cellular differentiation." Genes Dev., 18:1371 (2004).
Lovering, et al., "The muscular dystrophies: from genes to therapies." Tiys Ther., 85:1372-1388 (2005).
Lua, et al., "Fractal and statistical properties of large compact polymers: a computational study." Polymer, 45:717 (2004).
Lua, et al., "Statistics of knots, geometry of conformations, and evolution of proteins." PLoS Comput Biol., 2:e45 (2006).
Mateos-Langerak, et al.,"Spatially confined folding of chromatin in the interphase nucleus." Proc Natl Acad Sci USA, 106:3812 (2009).
Mateos-Langerak, et al.,"Spatially confined folding of chromatin in the interphase nucleus." Proc Natl Acad Sci USA, 106:3812 Supplemental (2009).
Mikkelsen, et al.,"Genome-wide maps of chromatin state in pluripotent and lineage-committed cells." Nature, 448:553 (2007).
Misteli, "Beyond the sequence: cellular organization of genome function." Cell, 128:787 (2007).
Münke, et al., "Chromosome structure predicted by a polymer model." Physical Review E, 57:5888 (1998).
Muntoni, et al., "The congenital muscular dystrophies in 2004: a century of exciting progress." Neuromuscul Disord., 14:635-49 (2004).
Naumann, et al., "Complete karyotype characterization of the K562 cell line by combined application of G-banding, multiplex-fluorescence in situ hybridization, fluorescence in situ hybridization, and comparative genomic hybridization." Leuk Res., 25:313 (2001).
Osborne, et al., "Active genes dynamically colocalize to shared sites of ongoing transcription." Nat Genet., 36:1065 (2004).

(56) References Cited

OTHER PUBLICATIONS

Padiyar, et al.,"Genetic and genomic approaches to glomerulosclerosis." Curr Mol., Med., 5:497-507 (2005).
Parkes, et al., "Genetic factors in sleep disorders." J Neurol Neurosurg Psychiatry, Suppl:101-108 (1989).
Phillips, et al., "CTCF: Master Weaver of the Genome." Cell 137:1194 (2009).
Rao, et al., "Causes and consequences of the autoimmune lymphoproliferative syndrome." Hematology, 11 :15-23 (2006).
Raizen, et al., "Genetic basis for sleep regulation and sleep disorders." Semin Neurol., 26:467-483 (2006).
Ralston, "Genetics of osteoporosis." Voc Afafr-Soc. 66:158-165 (2007).
Rioux, et al., "Paths to understanding the genetic basis of autoimmune disease." Nature, 435:584-589 (2005).
Rossi, et al., "SPINKl /PSTI mutations are associated with tropical pancreatitis in Bangladesh. A preliminary report." Pancreatology, 1 :242-245 (2001).
Sabo, et al.,"Genome-scale mapping of DNase I sensitivity in vivo using tiling DNA microarrays." Nat Methods, 3:511 (2006).
Sambrook, et al., *In: Molecular Cloning: A Laboratory Manual*, Cold Spring Harbor Press, NY, pp. 7.39-7.52, (1989).
Sambrook, et al., *In: Molecular Cloning: A Laboratory Manual*, Cold Spring Harbor Press, NY, pp. 9.31-9.58, (1989).
Seng, et al., "The success of the genome-wide association approach: a brief story of a long struggle" Eur J Hum Genet. 16:554-564 (2008).
Sexton, et al., "Gene regulation through nuclear organization." Nat Struct Mol Biol., 14:1049 (2007).
Shimada, et al., "The Folding Thermodynamics and Kinetics of Crambin Using an All-atom Monte Carlo Simulation."J Mol Biol., 308:79 (2001).
Shopland, et al., "Folding and organization of a contiguous chromosome region according to the gene distribution pattern in primary genomic sequence." J Cell Biol., 174:27 (2006).
Shopland, et al., "Folding and organization of a contiguous chromosome region according to the gene distribution pattern in primary genomic sequence." J Cell Biol., 174:27 Index of Supplemental Material (2006).
Shopland, et al., "Folding and organization of a contiguous chromosome region according to the gene distribution pattern in primary genomic sequence." J Cell Biol., 174:27 Supplemental Fig. 1 (2006).
Shopland, et al., "Folding and organization of a contiguous chromosome region according to the gene distribution pattern in primary genomic sequence." J Cell Biol., 174:27 Supplemental Fig. 2 (2006).
Shopland, et al., "Folding and organization of a contiguous chromosome region according to the gene distribution pattern in primary genomic sequence." J Cell Biol., 174:27 Supplemental Fig. 3 (2006).
Shopland, et al., "Folding and organization of a contiguous chromosome region according to the gene distribution pattern in primary genomic sequence." J Cell Biol., 174:27 Supplemental Fig. 4 (2006).
Shopland, et al., "Folding and organization of a contiguous chromosome region according to the gene distribution pattern in primary genomic sequence." J Cell Biol., 174:27 Supplemental Table 1 (2006).
Simonis, et al., "Nuclear organization of active and inactive chromatin domains uncovered by chromosome conformation capture—on-chip (4C)." Nature Genetics, 38:1341-1347 (2006).
Taheri, "The genetics of sleep disorders." Minerva Med., 95:203-212 (2004).
Tanabe, et al., "Non-random radial arrangements of interphase chromosome territories: evolutionary considerations and functional implications." Mutat Res 504:37 (2002).
Toumpanakis, et al., "Molecular genetics of gastroenteropancreatic neuroendocrine tumors." Am J Gastroenterol.,, 103:729-732 (2008).
Vasilyev, et al., "Theoretical and Mathematical Physics." 134:142 (2003).
Virnau, et al., "Intricate Knots in Proteins: Function and Evolution." PLoS Comput Biol., 2:e122 (2006).
Vologodskii, et al.,"Conformational and Thermodynamic Properties of Supercoiled DNA." J Mol Biol., 227: 1224 (1992).
Wagner, "Genetic diseases of muscle." Neurol Clin., 20:645-678 (2002).
Whitcomb, "Hereditary pancreatitis: a model for understanding the genetic basis of acute and chronic pancreatitis." Pancreatology, 1:565-570 (2001).
Yasmin, et al., "Genetics of arterial structure and function: towards new biomarkers for aortic stiffness?" Clin Sd (Lond), 114:661-677 (2008).
Yokota, et al., "Evidence for the organization of chromatin in megabase pair-sized loops arranged along a random walk path in the human G0/G1 interphase nucleus." J Cell Biol., 130:1239 (1995).
Yokota, et al., "Evidence for the organization of chromatin in megabase pair-sized loops arranged along a random walk path in the human G0/G1 interphase nucleus." J Cell Biol., 130:1239 correction (1995).
Zhang, et al., "Interactive analysis of systems biology molecular expression data." BMC Syst Biol., 2:23 (2008).
Zhao, et al., "Circular chromosome conformation capture (4C) uncovers extensive networks of epigenetically regulated intra- and interchromosomal interactions." Nature Genetics, 38:1348-1354 (2006).
ISR PCT2009005249.
Auburn, Recent Advances in the Determination of Three Three-Dimensional Chromosomal Conformation. http://biochem218.stanford.edu/Projects%202009/Auburn%202009.pdf (2009) A pp. 1-3.
Auburn, Recent Advances in the Determination of Three Three-Dimensional Chromosomal Conformation. http://biochem218.stanford.edu/Projects%202009/Auburn%202009.pdf (2009) B pp. 4-10.
Fullwood, et al., "An oestrogen-receptor-alpha-bound human chromatin interactome." Nature, 5:462(7269):58-64 (2009).
Hu, et al., "Enhancing nuclear receptor-induced transcription requires nuclear motor and LSD1-dependent gene networking in interchromatin granules." *Proc Natl Acad Sci U S A.*, 105(49):19199-204 (2008).
Lieberman-Aiden, et al., "Comprehensive Mapping of Long-Range Interactions Reveals Folding Principles of the Human Genome." *Science*, 326(5950):289-293 (2009).
McBride, et al., "Rounding up active cis-elements in the triple C corral: combining conservation, cleavage and conformation capture for the analysis of regulatory gene domains." *Brief Funct Genomic Proteomic.*, 3(3):267-79 (2004); and.
Wang, et al., "DNA interaction networks: an information highway for regulated gene expression in the 3-dimentional space of the nucleus." *Cell Research.*, 19:1316-1319 (2009).

\* cited by examiner

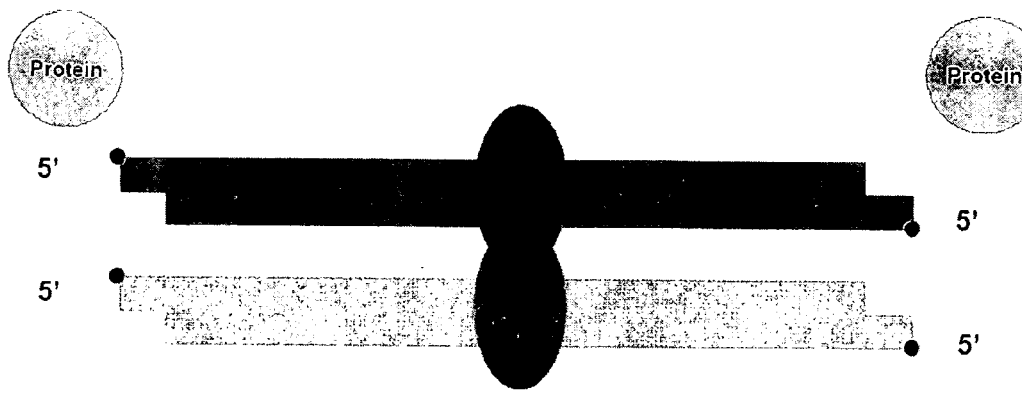
| 5' A    AGCTT 3' | → | 5' AA    AGCTT 3' |
| 3' TTCGA    A 5' |   | 3' TTCGA    AA 5' |
| *sticky overhangs* |   | *non-sticky overhangs* |
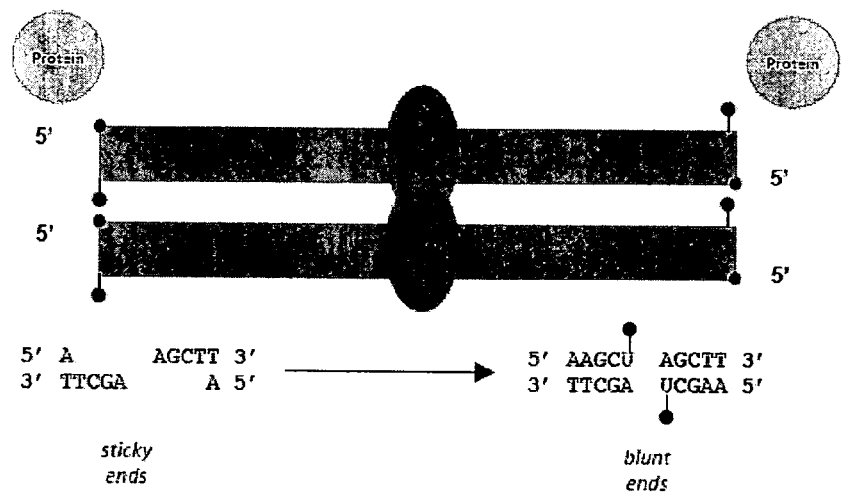
| 5' A    AGCTT 3' | → | 5' AAGCU AGCTT 3' |
| 3' TTCGA    A 5' |   | 3' TTCGA UCGAA 5' |
| *sticky ends* |   | *blunt ends* |
Figure 3B

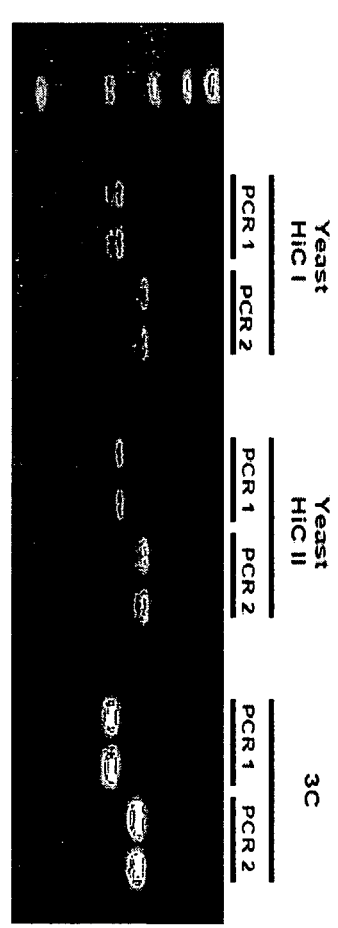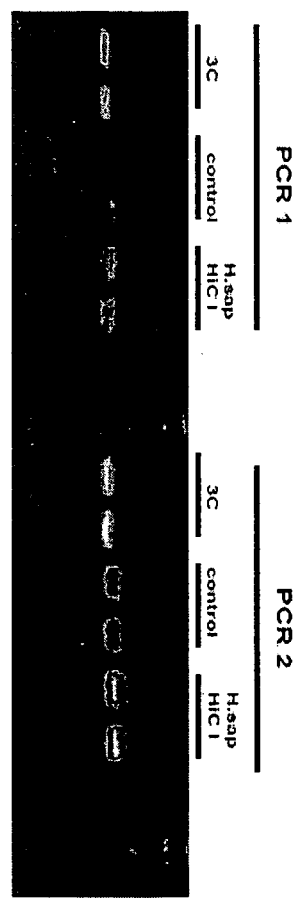
Figure 11

| Volume | Side | #Cubes | Int/Cube | #Interactions | #Possible Interactions | #I/#P | Change |
|--------|------|--------|----------|---------------|------------------------|-------|--------|
| N/4    | s/2  | 4      | 4s/2 = 2s | 8s           | $s^4$                  | $8/s^3$ |      |
| N/16   | s/4  | 16     | 4s/4 = s  | 16s          | $s^4/4$                | $64/s^3$ | 8   |

Smooth

Total Volume ~ N $s^2 = N$

Equilibrium globules
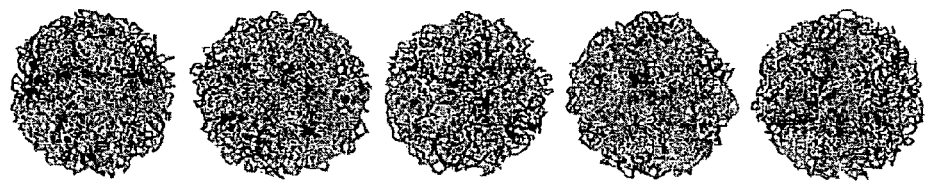
Fractal globules
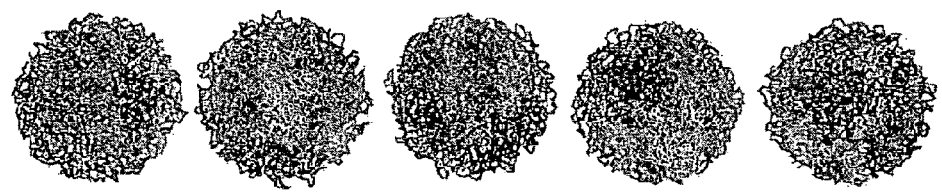
Figure 43

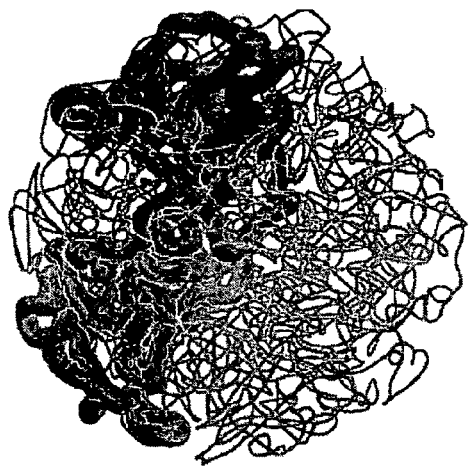 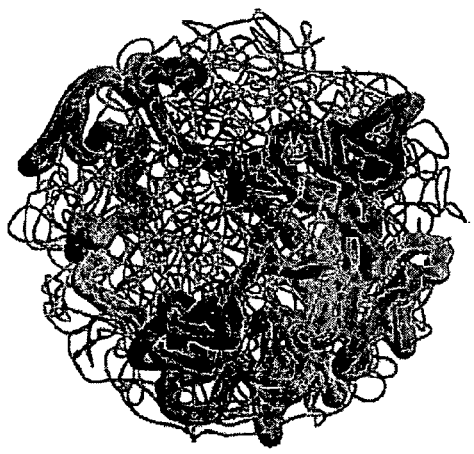
Fractal Globule                Equilibrium Globule
Figure 45

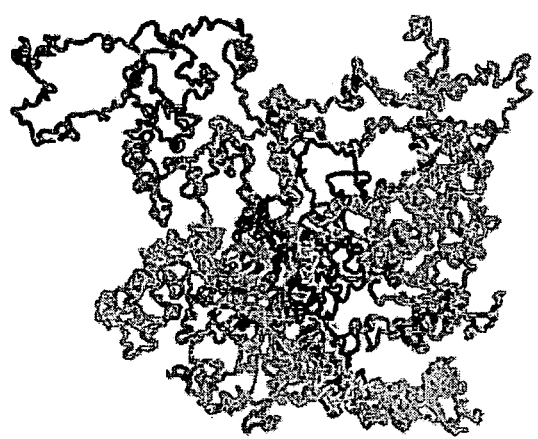 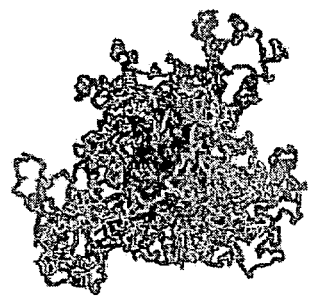
Fractal Globule  Equilibrium Globule
Figure 48

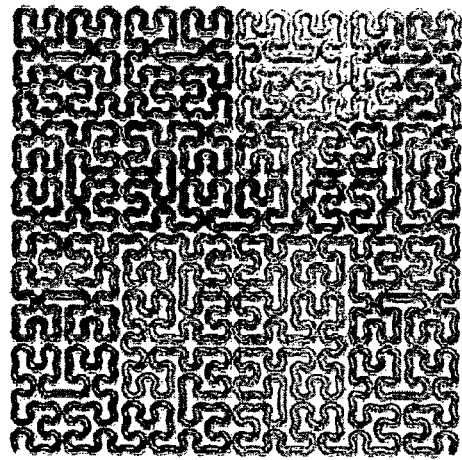 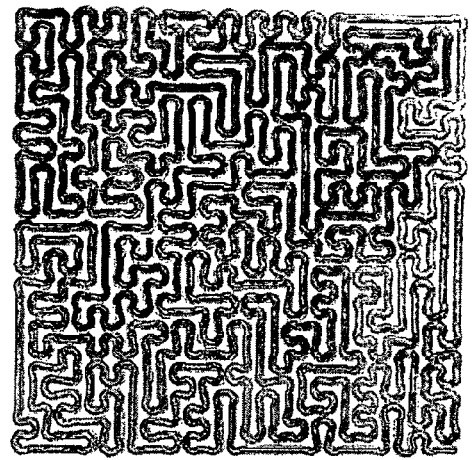
Peano Curve          Hamiltonian Path
Figurre 51

METHODS OF IDENTIFYING INTERACTIONS BETWEEN GENOMIC LOCI

This application for patent under 35 U.S.C. §111(a) claims priority to Provisional Application Ser. No. 61/100,151 filed on Sep. 25, 2008 under 35 U.S.C. §111(b).

FEDERALLY SPONSORED RESEARCH OR DEVELOPMENT

This invention was made with government support under grant no. HG003143 awarded by the National Institutes of Health. The government has certain rights in the invention.

FIELD OF INVENTION

The present invention is related to the field of genomic interactions and methods of detecting genomic interaction pathways. This detection method allows rapid and exhaustive analysis of chromosomal interactions throughout complete genomes, which allows unbiased identification of regulatory elements, and interactions between these elements, in any genome (ranging from prokaryotes to higher eukaryotes including human), in different cell types and in both normal and disease states. The method can be used to characterize and differentiate disease states from normal states, and can be used to assess effects of therapeutic interventions on genome regulation and function. The method can also be used as a diagnostic by detecting disease-correlated chromosome conformations.

BACKGROUND

Chromosomes, and genomes in general, are generally believed to be organized in three dimensions such that functionally related genomic elements, e.g. enhancers and their target genes, are directly interacting or are located in very close spatial proximity. Such close physical proximity between genomic elements has been reported to play a role in genome biology both in normal development and homeostasis and in disease.

Genomes are believed to be multicompositional complexes comprising of mainly nucleic acids and proteins. Polymers of both biological building blocks have primary, secondary, and tertiary conformational structure. For example, a primary conformational structure is believed to be represented by a linear sequence of individual nucleotides, thereby forming a polynucleotide or a linear sequence of individual amino acids, thereby forming a protein (i.e., includes the first dimension).

On the other hand, both secondary and tertiary conformational structures describe torsional considerations of the polynucleotide or protein in response to the ionic charges and steric interactions of the various chemical moieties that make up the primary sequences. Secondary structure is related to twisting and turning relative to the longitudinal axis of the polymer (i.e., includes the first and second dimensions). Tertiary structure is related to folding and looping of the polymer (i.e., includes the first, second and third dimensions).

What is needed in the art is a method by which direct intra- and interchromosomal interactions between remote regulatory elements, or spatial proximity of these elements, may be identified in a comprehensive manner and utilized to diagnose specific medical and/or biological conditions.

SUMMARY

The present invention is related to the field of genomic interactions and methods of detecting genomic interactive pathways. This detection method allows rapid and exhaustive identification of chromosomal interactions throughout complete genomes, which allows unbiased discovery of regulatory elements, or interactions between regulatory elements, or interactions between genomic loci that reflect or contribute to three-dimensional structure of chromosomes, in any genome (ranging from prokaryotes to higher eukaryotes including human), in different cell types and in both normal and disease states. The method can be used to characterize and differentiate disease states from normal states and can be used to assess effects of therapeutic interventions on genome regulation and function. The method can also be used as a diagnostic by detecting disease-correlated chromosome conformations.

The present invention contemplates a Hi-C genomic assay technology having many possible embodiments. In particular, embodiments including, but not limited to, fixation, fragmentation, marking of ligation junctions, purification, and analysis can be accomplished using a multiplicity of methods. Consequently, the final assay and subsequent data analysis can also vary widely.

In one embodiment, the present invention contemplates a method comprising: i) fragmenting a cross-linked genome thereby creating a plurality of fragments, ii) ligating the fragments under conditions such that the created ligation junctions are marked; iii) selectively purifying the fragments on the basis of the marked ligation junctions; and iv) analyzing the marked ligation junctions in order to determine their identity.

In one embodiment, the present invention contemplates a method comprising: a) providing; i) a nuclear matrix comprising a first region and a second region; and ii) a junction marker; b) incorporating the junction marker into the nuclear matrix; and c) analyzing an interaction frequency. In one embodiment, the analyzing determines the interaction frequency between the first region and the second region. In one embodiment, the method further comprises fragmenting the nuclear matrix. In one embodiment, the junction marker comprises a labeled nucleotide linker (i.e., for example, biotin). In one embodiment, the junction marker comprises a modified nucleotide. In one embodiment, the junction marker comprises a primer linker. In one embodiment, the labeled nucleotide linker comprises two repeating sequences. In one embodiment, the labeled nucleotide linker comprises three repeating sequences. In one embodiment, the first and second regions are located on the same chromosome. In one embodiment, the first and second regions are located on different chromosomes. In one embodiment, the interaction frequency identifies a long range interaction. In one embodiment, the interaction frequency identifies a short range interaction. In one embodiment, the interaction frequency identifies a close neighbor interaction. In one embodiment, the nuclear matrix is derived from a human cell nucleus. In one embodiment, the nuclear matrix is derived from a yeast cell nucleus. In one embodiment, the analyzing identifies an altered primary structure of the nuclear matrix. In one embodiment, the nuclear matris derived from a cell selected from the group including, but not limited to, cows, pigs, horses, dogs, cats, goats, or sheep. In one embodiment, the nuclear matrix is derived from a source including, but not limited to, bacterial, fungus, and/or mold.

In one embodiment, the present invention contemplates a method comprising; a) providing; i) a cell comprising at least one chromosome, wherein the at least one chromosome comprises a first region and a second region; and ii) a junction marker; b) extracting the at least one chromosome from said cell; c) incorporating the junction marker into the extracted chromosome; and d) analyzing an interaction frequency. In one embodiment, the analyzing determines the interaction frequency between the first region and the second region. In one embodiment, the method further comprises fragmenting the at least one chromosome. In one embodiment, the junction marker comprises a labeled nucleotide linker (i.e., for example, biotin). In one embodiment, the junction marker comprises a modified nucleotide. In one embodiment, the junction marker comprises a primer linker. In one embodiment, the labeled nucleotide linker comprises two repeating sequences. In one embodiment, the labeled nucleotide linker comprises three repeating sequences. In one embodiment, the first and second region are located on the same chromosome. In one embodiment, the first and second region are located on different chromosomes. In one embodiment, the interaction frequency identifies a long range interaction. In one embodiment, the interaction frequency identifies a short range interaction. In one embodiment, the interaction frequency identifies a close neighbor interaction. In one embodiment, the at least one chromosome comprises a human chromosome. In one embodiment, the at least one chromosome comprises a yeast chromosome. In one embodiment, the analyzing identifies an altered primary structure of the at least one chromosome. In one embodiment, the chromosome derived from a cell selected from the group including, but not limited to, cows, pigs, horses, dogs, cats, goats, or sheep. In one embodiment, the nuclear matrix is derived from a source including, but not limited to, bacterial, fungus, and/or mold.

In one embodiment, the present invention contemplates a method comprising; a) providing; i) a cell comprising a fixed genome; ii) a join, wherein the join comprises two ligated nucleic acid sequences derived from the fixed genome; and iii) a plurality of paired end sequencing adaptors; b) ligating the paired end adaptors to the join; and c) analyzing the join. In one embodiment, the analyzing comprises nucleic acid sequencing. In one embodiment, the method further comprises step d) comparing the join sequence to the genome. In one embodiment, the cell comprises a non-mammalian cell. In one embodiment, the non-mammalian cell comprises a cell selected from the group including, but not limited to, fish, amphibian, insects, birds, yeast, fungi, bacteria, or mold. In one embodiment, the cell comprises a mammalian cell. In one embodiment, the cell comprises a plant cell. In one embodiment, the mammalian cell comprises a human cell. In one embodiment, the cell comprises a yeast cell. In one embodiment, the fixed genome comprises crosslinks. In one embodiment, the crosslinks are selected from the group including, but not limited to, nucleic acid-nucleic acid crosslinks or protein-nucleic acid crosslinks. In one embodiment, the join sequence comprises identity with at least two genomic regions. In one embodiment, the first genomic region comprises a first gene. In one embodiment, the second genomic element comprises a second gene. In one embodiment, the first genomic region comprises a first regulatory element. In one embodiment, the second genomic region comprises a second regulatory element. In one embodiment, the first genomic region comprises an open reading frame sequence. In one embodiment, the second genomic region comprises a regulatory element. In one embodiment, the regulatory element interacts with the open reading frame sequence. In one embodiment, the analyzing identifies an altered primary sequence of the genome.

In one embodiment, the present invention contemplates a method comprising; a) providing; i) a mammalian cell comprising a crosslinked genome; ii) a join, wherein the join comprises two ligated nucleic acid sequences derived from the crosslinked genome; and iii) a plurality of paired end sequencing adaptors; b) ligating the paired end adaptors to the join; c) sequencing the join; and d) comparing the join sequence to the genome. In one embodiment, the mammalian cell comprises a human cell. In one embodiment, the mammalian cell comprises a non-human cell. In one embodiment, the non-human cell is selected from the group including, but not limited to, cows, pigs, horses, dogs, cats, goats, or sheep. In one embodiment, the join sequence comprises identity with at least two genomic regions. In one embodiment, the first genomic region comprises a first gene. In one embodiment, the second genomic element comprises a second gene. In one embodiment, the first genomic region comprises a first regulatory element. In one embodiment, the second genomic region comprises a second regulatory element. In one embodiment, the first genomic region comprises an open reading frame sequence. In one embodiment, the second genomic region comprises a regulatory gene. In one embodiment, the regulatory gene interacts with the open reading frame sequence. In one embodiment, the regulatory element interacts with the open reading frame sequence. In one embodiment, the analyzing identifies an altered primary sequence of the genome. In one embodiment, the regulatory element interacts with disease-related gene. In one embodiment, the open reading frame sequence encodes a protein associated with a medical condition. In one embodiment, the medical condition comprises cancer. In one embodiment, the medical condition comprises a cardiovascular disease. In one embodiment, the medical condition comprises a kidney disease. In one embodiment, the medical condition comprises an autoimmune disease. In one embodiment, the medical condition comprises a pulmonary disease. In one embodiment, the medical condition comprises a pancreatic disease. In one embodiment, the medical condition comprises a muscular disease. In one embodiment, the medical condition comprises a bone disease. In one embodiment, the medical condition comprises a blood disorder disease. In one embodiment, the medical condition comprises a sleep disorder. In one embodiment, the regulatory gene comprises an enhancer. In one embodiment, the regulatory gene comprises a silencer. In one embodiment, the regulatory gene comprises an insulator.

In one embodiment, the present invention contemplates a method, comprising: a) providing; i) a patient expressing at least one symptom of a medical condition; ii) a cell derived from the patient, wherein the cell comprises a first genomic region and a second genomic region; b) analyzing an interaction frequency; and c) diagnosing the medical condition under conditions such that the interaction frequency is outside a normative range. In one embodiment, the analyzing determines the interaction frequency between the first genomic region and the second genomic region. In one embodiment, the first and second genomic regions are located on the same chromosome. In one embodiment, the first genomic region comprises a first gene. In one embodiment, the second genomic element comprises a second gene. In one embodiment, the first genomic region comprises a first regulatory element. In one embodiment, the second genomic region comprises a second regulatory element. In one embodiment, the first and second genomic regions are located on different chromosomes. In one embodiment, the first genomic region comprises an open reading frame sequence. In one embodiment, the second genomic region comprises a regulatory gene. In one embodiment, the regulatory gene interacts with the open reading frame sequence. In one embodiment, the analyzing identifies an altered primary sequence of the first genomic region. In one embodiment, the analyzing identifies an altered primary sequence of the second genomic region. In one embodiment, the open reading frame sequence encodes a protein associated with a medical condition. In one embodiment, the medical condition comprises cancer. In one embodiment, the medical condition comprises a cardiovascular disease. In one embodiment, the medical condition comprises a kidney disease. In one embodiment, the medical condition comprises an autoimmune disease. In one embodiment, the medical condition comprises a pulmonary disease. In one embodiment, the medical condition comprises a pancreatic disease. In one embodiment, the medical condition comprises a muscular disease. In one embodiment, the medical condition comprises a bone disease. In one embodiment, the medical condition comprises a blood disorder disease. In one embodiment, the medical condition comprises a sleep disorder. In one embodiment, the regulatory gene comprises an enhancer. In one embodiment, the regulatory gene comprises a silencer. In one embodiment, the regulatory gene comprises an insulator.

In one embodiment, the present invention contemplates a kit, comprising i) a fixation agent capable of crosslinking nucleic acid and/or protein; ii) an enzyme capable of fragmenting nucleic acids, iii) a junction marker capable of providing selective purification; and iv) a paired end sequencing adaptor compatible with a high throughput sequencing device. In one embodiment, the kit further comprises buffers and reagents capable of supporting the nucleic acid and/or protein fixing. In one embodiment, the kit further comprises buffers and reagents capable of supporting the enzyme nucleic acid fragmentation. In one embodiment, the kit further comprises buffers and reagents capable of supporting selective purification using the junction marker. In one embodiment, the junction marker comprises a labeled nucleotide linker (i.e., for example, biotin). In one embodiment, the junction marker comprises a modified nucleotide. In one embodiment, the junction marker comprises a primer linker. In one embodiment, the labeled nucleotide linker comprises two repeating sequences. In one embodiment, the labeled nucleotide linker comprises three repeating sequences. In one embodiment, the kit further comprises buffers and reagents capable of supporting the high throughput sequencing device using the paired end sequencing adaptors. In one embodiment, the kit further comprises a sheet of instructions. In one embodiment, the sheet of instructions describes the nucleic acid and/or protein fixing. In the sheet of instructions describes the enzyme nucleic acid fragmentation. In one embodiment, the sheet of instructions describes selective purification using the junction markers. In one embodiment, the sheet of instructions describe the high throughput sequencing using the paired end sequencing adaptors.

In one embodiment, the present invention contemplates a method, comprising: a) providing a fixed genome and a junction marker; b) fragmenting said fixed genome to produce a fragmented, fixed genome; and c) treating said fragmented, fixed genome in the presence of said marker under conditions such that there is ligation among at least a portion of the fragments, said ligation creating ligation junctions, said ligation junctions being marked with said junction marker. In one embodiment, the method further comprises d) contacting said marker with a ligand. In one embodiment, the marker comprises biotin. In one embodiment, the ligand comprises streptavidin. In one embodiment, the method further comprises analyzing said ligation junctions. In one embodiment, the analyzing comprises nucleic acid sequencing. In one embodiment, the fixed genome comprises crosslinked nucleic acids. In one embodiment, the fragmenting of step b) comprises digesting said cross-linked genome with one or more restriction enzymes.

In one embodiment, the present invention contemplates a method, comprising i) fixing a genome, wherein the spatial orientation of genomic interactions is immobilized; ii) fragmenting the genome, thereby creating fragments; iii) ligating junction markers to the fragments; iv) purifying the junction markers; and iv) analyzing the junction markers. In one embodiment, the genomic interactions are immobilized by crosslinks, including, but not limited to, protein-protein crosslinks, protein-nucleic acid crosslinks, or nucleic acid-nucleic acid crosslinks. In one embodiment, the spatial orientation comprises a tertiary structure. In one embodiment, the spatial orientation comprises a secondary structure. In one embodiment, the spatial orientation comprises a primary structure. In one embodiment, the junction markers comprise a label. In one embodiment, the purifying comprises using the label. In one embodiment, the analyzing comprises heatmap analysis. In one embodiment, the analyzing comprises nucleic acid sequencing.

In one embodiment, the sequencing is capable of determining whether specific genomic variants are involved in specific genomic interactions. In one embodiment, the genomic variants comprise single nucleotide polymorphisms. In one embodiment, the genomic variants comprise deletions. In one embodiment, the genomic variants comprise additions. In one embodiment, the genomic variants comprise substitutions. In one embodiment, the genomic variants comprise mutations. In one embodiment, the genomic variants comprise splice variants.

In one embodiment, the present invention contemplates a method comprising treating a Hi-C library with a bisulphite compound, wherein unmethylated cytosines are converted into uracil residues. In one embodiment, the method further comprises identifying at least one genomic interaction located at a methylated allele. In one embodiment, the method further comprises identifying at least one genomic interaction located at an unmethylated allele.

In one embodiment, the present invention contemplates a genomic spatial proximity map, wherein the map defines a chromatin complex at a 1 Mb resolution. In one embodiment, the map comprises a genome-wide contact matrix. In one embodiment, the proximity map defines at least one chromosome compartment (i.e., for example, an open compartment or a chromosome territory). In one embodiment, the proximity map defines at least one sub-nuclear positioning pattern. In one embodiment, the spatial proximity map is defined by a plurality of interaction probability. In one embodiment, the map generates a plaid-like pattern. In one embodiment, the map generates a non-plaid-like pattern. In one embodiment, the map generates a sharpened plaid pattern, wherein the interactions were defined using a correlation matrix. In one embodiment, the plaid pattern defines the at least one chromatin compartment. In one embodiment, the map comprises a plurality of preferential chromosome interactions. In one embodiment, a first chromosome compartment comprises an open chromatin compartment. In one embodiment, the first chromosome compartment comprises a first interaction frequency. In one embodiment, a second chromosome compartment comprises a closed chromatin compartment. In one embodiment, the second compartment comprises a second interaction frequency. In one embodiment, the first interaction frequency is greater than the second interaction frequency, wherein the first compartment comprises densely packed chromatin. In one embodiment, the first and second compartments further comprise a genomic genetic or epigenetic feature. In one embodiment, the first and second compartments further comprise an activating chromatin mark or a repressive chromatin mark. In one embodiment, the activating or repressive chromatin mark comprises at least one trimethylation mark. In one embodiment, the chromatin compartment comprises a fractal globule. In one embodiment, the fractal globule is knot-free. In one embodiment, the fractal globule is nearly knot-free In one embodiment, the chromatin compartment comprises a polymer state including, but not limited to, an equilibrium globule, a self-avoiding walk, or a random walk. In one embodiment, the chromatin compartment comprises an ordered state. In one embodiment, the chromatin compartment comprises a statistical ensemble. In one embodiment, the genomic spatial proximity map comprises a heatmap.

In one embodiment, the present invention contemplates a Hi-C library. In one embodiment, the library is created by shearing the DNA and selecting the biotin-containing fragments with streptavidin beads. In one embodiment, the library is analyzed using massively parallel DNA sequencing, thereby producing a catalog of interacting fragments. In one embodiment, the library comprises between approximately 1-25 million read pairs. In one embodiment, the library comprises between approximately 3-15 million read pairs. In one embodiment, the library comprises between approximately 5-10 million read pairs. In one embodiment, the library comprises approximately 8 million read pairs. In one embodiment, between approximately 0.5-20 million read pairs correspond to long range interactions. In one embodiment, between approximately 2-10 million read pairs correspond to long range interactions. In one embodiment, between approximately 5-8 million read pairs correspond to long range interactions. In one embodiment, approximately 7 million read pairs correspond to long range interactions. In one embodiment, the long range interactions are at least greater than 20 Kb apart.

DEFINITIONS

The term "nuclear matrix" as used herein, refers to any composition comprising nucleic acids and protein. The nucleic acids may be organized into chromosomes, wherein the proteins (i.e., for example, histones) may become associated with the chromosomes having a regulatory function.

The term "genomic region" or "region" as used herein, refers to any defined length of a genome and/or chromosome. For example, a genomic region may refer to the association (i.e., for example, an interaction) between more than one chromosomes. Alternatively, a genomic region may refer to a complete chromosome or a partial chromosome. Further, a genomic region may refer to a specific nucleic acid sequence on a chromosome (i.e., for example, an open reading frame and/or a regulatory gene).

The term "junction marker" as used herein, refers to any compound or chemical moiety that is capable of being incorporated within a nucleic acid and can provide a basis for selective purification. For example, a junction marker may include, but not be limited to, a labeled nucleotide linker, a labeled and/or modified nucleotide, nick translation, primer linkers, or tagged linkers.

The term "labeled nucleotide linker" as used herein, refers to a type of junction marker comprising any nucleic acid sequence comprising a label that may be incorporated (i.e., for example, ligated) into another nucleic acid sequence. For example, the label may serve to selectively purify the nucleic acid sequence (i.e., for example, by affinity chromatography). Such a label may include, but is not limited to, a biotin label, a histidine label (i.e., 6His), or a FLAG label.

The term "labeled nucleotide", "labeled base", or "modified base" as used herein, refers to a junction marker comprising any nucleotide base attached to a marker, wherein the marker comprises a specific moiety having a unique affinity for a ligand. Alternatively, a binding partner may have affinity for the junction marker. In some examples, the marker includes, but is not limited to, a biotin marker, a histidine marker (i.e., 6His), or a FLAG marker. For example, dATP-Biotin may be considered a labeled nucleotide. In some examples, a fragmented nucleic acid sequence may undergo blunting with a labeled nucleotide followed by blunt-end ligation.

The term "nick translation" as used herein, refers to a junction marker comprising the introduction of a proto-marker (i.e., for example, a modified base) within a nucleic acid sequence. Such a junction marker is typically linker-free (i.e., no additional nucleotide bases are added to the nucleic acid sequence).

The term "primer linker" as used herein, refers to a junction marker comprising a modified nucleic acid sequence flanked by primer sequences. For example, the primer sequences may comprise universal primers such that the junction sequence may be extracted and amplified by polymerase chain reaction.

The term "interaction frequency" as used herein, refers to measuring the spatial proximity probability of two different genomic regions. As the interaction frequency increases the probability increases that the two genomic regions are physically proximal to one another. Conversely, as the interaction frequency decreases the probability decreases that the two genomic regions are physically proximal to one another. More specifically, two genomic regions with a high interaction frequency most likely share a short range or close neighbor spatial proximity. Alternatively, two genomic regions with a low interaction frequency most likely share a long range spatial proximity.

The term "fragments" as used herein, refer to any nucleic acid sequence that is shorter than the sequence from which it is derived. Fragments can be of any size, ranging from several megabases and/or kilobases to only a few nucleotides long. Experimental conditions can determine an expected fragment size, including but not limited to, restriction enzyme digestion, sonication, acid incubation, base incubation, microfluidization etc.

The term "chromosome" as used herein, refers to a naturally occurring nucleic acid sequence comprising a series of functional regions termed genes, that usually encode proteins. Other functional regions may include microRNAs or long noncoding RNAs, or other regulatory elements. These proteins may have a biological function or they directly interact with the same or other chromosomes (i.e., for example, regulatory chromosomes).

The term "long range interaction" as used herein, refers to the detection of an enriched genomic interaction frequency between genomic regions that are far apart along the linear genome sequence. The baseline interaction frequency for such regions is usually low. This type of interaction may identify two genomic regions that are, for instance, located on different telomeres of the same chromosome, or located on different chromosomes.

The term "short range interaction" as used herein, refers to the detection of an enriched genomic interaction frequency between genomic regions that are not far apart in the genome. The baseline interaction frequency for such regions is usually medium. This type of interaction identifies two genomic regions that are, for instance, located on the same telomere of the same chromosome.

The term "close neighbor interaction" as used herein, refers to the detection of a high genomic interaction frequency. This type of interaction identifies two genomic regions that are close to each other in the linear genome and, for instance, part of the same gene.

The term "cell" as used herein, refers to any small, usually microscopic, mass of protoplasm bounded externally by a semi-permeable membrane, usually including one or more nuclei and various nonliving products, capable alone or interacting with other cells of performing all the fundamental functions of life, and forming the smallest structural unit of living matter capable of functioning independently. Cells used in the present invention may include, but are not limited to, animal cells, plant cells, mammalian cells, yeast cells, or microbial cells.

The term "nucleus" as used herein, refers to any cellular organelle of eukaryotes that comprises a nucleoprotein-rich network from which chromosomes and nucleoli arise, and is enclosed in a definite membrane.

The term "incorporating" as used herein, refers to any process or mechanism by which single components become part of a larger system. For example, a nucleoside may become incorporated into a nucleic acid by forming, for example, a phosphodiester bond. Such an incorporation allows the previously single component to function as one with the larger system.

The term "analyzing" as used herein, refers to any process or method by which a collection of information is used to make a conclusion based upon fact (i.e., for example, scientific data). For example, a genomic interaction frequency may be analyzed by performing a heatmap analysis of a crosslinked genome, wherein signal intensity is reflective of the level of genomic interaction. Analyzing may also comprise sequencing or other techniques.

The term "heatmap", as used herein, refers to any graphical representation of data where the values taken by a variable in a two-dimensional map are represented as colors. Heat maps have been widely used to represent the level of expression of many genes across a number of comparable samples (e.g. cells in different states, samples from different patients) as obtained from DNA microarrays.

The term "fragmenting" as used herein, refers to any process or method by which a compound or composition is separated into smaller units. For example, the separation may include, but is not limited to, enzymatic cleavage (i.e., for example, restriction enzymes acting upon nucleic acids or protease enzymes acting on proteins), base hydrolysis, acid hydrolysis, or heat-induced thermal destabilization.

The term "extracting" as used herein, refers to any process or method by which the individual components of a composition may be separated without loss of individual integrity. For example, the separation may be accomplished by methods including, but not limited to, centrifugation or solubility (i.e., for example, based upon relative pKa values or hydrophobic and hydrophilic properties).

The term "genome" as used herein, refers to any set of chromosomes with the genes they contain. For example, a genome may include, but is not limited to, eukaryotic genomes and prokaryotic genomes.

The term "fixing", "fixation" or "fixed" as used herein, refers to any method or process that immobilizes any and all cellular processes. A fixed cell, therefore, accurately maintains the spatial relationships between intracellular components at the time of fixation. Many chemicals are capable of providing fixation, including but not limited to, formaldyhyde, formalin, or glutaraldehyde.

The term "crosslink", "crosslinking" or "crosslink" as used herein, refers to any stable chemical association between two compounds, such that they may be further processed as a unit. Such stability may be based upon covalent and/or non-covalent bonding. For example, nucleic acids and/or proteins may be crosslinked by chemical agents (i.e., for example, a fixative) such that they maintain their spatial relationships during routine laboratory procedures (i.e., for example, extracting, washing, centrifugation etc.)

The term "join" as used herein, refers to a unique linkage of two nucleic acid sequences by a junction marker. Such linkages may arise by processes including, but not limited to, fragmentation, filling in with marked nucleotides, and blunt end ligation. Such a join reflects the proximity of two genomic regions thereby providing evidence of a functional interaction. A join comprising a junction marker may be selectively purified in order to facilitate a sequencing analysis.

The term "ligated" as used herein, refers to any linkage of two nucleic acid sequences usually comprising a phosphodiester bond. The linkage is normally facilitated by the presence of a catalytic enzyme (i.e., for example, a ligase) in the presence of co-factor reagents and an energy source (i.e., for example, adenosine triphosphate (ATP)).

The term "nucleic acid sequences" as used herein, refers to any polymer of nucleotides (i.e., for example, adenine, thymidine, cytosine, guanosine, and/or uracil) that may result in a functional genomic fragment or gene. A combination of nucleic acid sequences may ultimately comprise a chromosome. A nucleic acid sequence comprising deoxyribonucleosides is referred to as deoxyribonucleic acid (DNA). A nucleic acid sequence comprising ribonucleosides is referred to as ribonucleic acid (RNA).

The term "paired end adaptors" as used herein, refers to any primer pair set that allows automated high throughput sequencing to read from both ends simultaneously. For example, such high throughput sequencing devices that are compatible with these adaptors include, but are not limited to Solexa (Illumina), the 454 System, and/or the ABI SOLiD. For example, the method may include using universal primers in conjunction with poly-A tails.

The term "identity" as used herein, refers a comparison of two polymers that have an exact sequence, both in composition and order. For example, a first nucleic acid sequence of A-T-G has identity to a second nucleic acid sequence of A-T-G. In this manner, an isolated nucleic acid sequence having identity to a genomic sequence can be accurately mapped to a specific chromosomal locus.

The term "open reading frame" or "coding region" as used herein, refers to any nucleic acid sequence encoding a non-regulatory protein.

The term "regulatory gene" or "regulatory elements" as used herein, refers to any nucleic acid sequence encoding a protein, wherein the protein binds to the same or different nucleic acid sequence thereby modulating the transcription rate or otherwise affecting the expression level of the same or different nucleic acid sequence. For example, various regulatory elements may include, but are not limited to, enhancers, repressors, insulators, promoters, The term "regulatory element" as used herein, refers to any nucleic acid sequence that affects activity status of another genomic elements. Examples include, but are not limited, to enhancer, repressors, insulators, boundary elements, origin of DNA replication, telomere, and/or centromere.

The term "medical condition" as used herein, refers to any alteration in physiological and/or biological homeostasis within a patient wherein a therapy is usually required to reestablish the homeostasis. For example, such conditions may include, but are not limited to, cancer, cardiovascular disease, kidney disease, autoimmune disease, pulmonary disease, pancreatic disease, muscle disease, bone disease, blood disorders, or sleep disorders.

The term "symptom" as used herein, refers to any observed subjective evidence of a medical condition, and/or objective evidence of a medical condition detected by the performance of a scientific test.

The term "diagnosing" as used herein, refers to any process or method by which a collection of test results and/or subjective symptoms allows a medical practitioner to recognize the presence of a specific medical condition. Such a diagnosis inherently excludes other similar medical conditions (i.e., for example, a differential diagnosis).

The term "restriction enzyme" as used herein, refers to any protein that cleaves nucleic acid at a specific base pair sequence.

The term "buffer" as used herein, refers to any balanced salt solution that maintains a predetermined pH level.

The term "reagent" as used herein, refers to any chemical or compound having a specific biological or biochemical activity that is added to a reaction mixture to achieve a predetermined outcome.

The term "selective purification" as used herein, refers to any process or method by which a specific compound and/or complex may be removed from a mixture or composition. For example, such a process may be based upon affinity chromatography where the specific compound to be removed has a higher affinity for the chromatography substrate than the remainder of the mixture or composition. For example, nucleic acids labeled with biotin may be selectively purified from a mixture comprising nucleic acids not labeled with biotin by passing the mixture through a chromatography column comprising streptavidin.

The term "sheet of instructions" as used herein, refers to a permanent recording (i.e., for example, written, oral, or graphic) that allows comprehension of a series of stepwise procedures to achieve a desired outcome. For example, the instructions may provide steps to fix and fragment nucleic acid from a mammalian cell. Alternatively, the instructions may provide steps to ligate a junction marker and/or an end paired adaptor into a nucleic acid. Such instructions may be recorded on a tangible media (i.e., for example, paper) or an intangible media (i.e., for example, electronic and/or digital).

The term, "purified" or "isolated", as used herein, may refer to a nucleic acid composition that has been subjected to treatment (i.e., for example, fractionation) to remove various other components, and which composition substantially retains its expressed biological activity. Where the term "substantially purified" is used, this designation will refer to a composition in which the nucleic acid forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeniety" such that there is single nucleic acid sequence (i.e., for example, based upon SDS-PAGE or HPLC analysis). A purified composition is not intended to mean that some trace impurities may remain. As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The term "functionally equivalent codon", as used herein, refers to different codons that encode the same amino acid. This phenomenon is often referred to as "degeneracy" of the genetic code. For example, six different codons encode the amino acid arginine.

A "variant" of a nucleotide is defined as a novel nucleotide sequence which differs from a reference oligonucleotide by having deletions, insertions and substitutions. These may be detected using a variety of methods (e.g., sequencing, hybridization assays etc.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues.

A "substitution" results from the replacement of one or more nucleotides or amino acids by different nucleotides or amino acids, respectively.

The term "derivative" as used herein, refers to any chemical modification of a nucleic acid or an amino acid. Illustrative of such modifications would be replacement of hydrogen by an alkyl, acyl, or amino group. For example, a nucleic acid derivative would encode a polypeptide which retains essential biological characteristics.

The term "portion" when used in reference to a nucleotide sequence refers to fragments of that nucleotide sequence. The fragments may range in size from 5 nucleotide residues to the entire nucleotide sequence minus one nucleic acid residue.

The term "biologically active" refers to any molecule having structural, regulatory or biochemical functions.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of any compound with a nucleic acid or peptide wherein that the interaction is dependent upon the presence of a particular structure (i.e., for example, an antigenic determinant or epitope). For example, if an antibody is specific for epitope "A", the presence of a protein containing epitope A (or free, unlabelled A) in a reaction containing labeled "A" and the antibody will reduce the amount of labeled A bound to the antibody.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed a a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

Low stringency conditions comprise conditions equivalent to binding or hybridization at 42° C. in a solution consisting of 5×SSPE (43.8 g/l NaCl, 6.9 g/l NaH2PO4.H2O and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length. is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., C0 t or R0 t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "Tm" is used in reference to the "melting temperature." The melting temperature is the temperature at which a population of double-stranded nucleic acid molecules becomes half dissociated into single strands. As indicated by standard references, a simple estimate of the Tm value may be calculated by the equation: $Tm=81.5+0.41$ (% G+C), when a nucleic acid is in aqueous solution at 1M NaCl. Anderson et al., "Quantitative Filter Hybridization" In: Nucleic Acid Hybridization (1985). More sophisticated computations take structural, as well as sequence characteristics, into account for the calculation of Tm.

As used herein the term "stringency" is used in reference to the conditions of temperature, ionic strength, and the presence of other compounds such as organic solvents, under which nucleic acid hybridizations are conducted. "Stringency" typically occurs in a range from about Tm to about 20° C. to 25° C. below Tm.

A "stringent hybridization" can be used to identify or detect identical polynucleotide sequences or to identify or detect similar or related polynucleotide sequences. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction. Dieffenbach C. W. and G. S. Dveksler (1995) In: PCR Primer, a Laboratory Manual, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence. DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription. Maniatis, T. et al., Science 236:1237 (1987). Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site. Sambrook, J. et al., In: Molecular Cloning: A Laboratory Manual, 2nd ed., Cold Spring Harbor laboratory Press, New York (1989) pp. 16.7-16.8. A commonly used splice donor and acceptor site is the splice junction from the 16S RNA of SV40.

The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. Efficient expression of recombinant DNA sequences in eukaryotic cells involves expression of signals directing the efficient termination and polyadenylation of the resulting transcript. Transcription termination signals are generally found downstream of the polyadenylation signal and are a few hundred nucleotides in length.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: Molecular Cloning: A Laboratory Manual, Cold Spring Harbor Press, NY, pp 9.31-9.58.

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J. Sambrook, J. et al. (1989) supra, pp 7.39-7.52.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonucleotide probe or RNA probe to detect DNA species complementary to the ribo probe used.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). A biological sample suspected of containing nucleic acid encoding a collagen-like family protein may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "binding" as used herein, refers to any interaction between an infection control composition and a surface. Such as surface is defined as a "binding surface". Binding may be reversible or irreversible. Such binding may be, but is not limited to, non-covalent binding, covalent bonding, ionic bonding, Van de Waal forces or friction, and the like. An infection control composition is bound to a surface if it is impregnated, incorporated, coated, in suspension with, in solution with, mixed with, etc.

BRIEF DESCRIPTION OF THE FIGURES

FIG. 3B presents two embodiments for partially filling in the digested ends. Top Panel: Sticky (i.e., for example, complementary) overhangs are converted into non-sticky (i.e., for example, non-complementary) overhangs by using Klenow+dATP for ~30 min). Bottom Panel: A sticky overhang is converted into a blunt end by using Klenow+dA, dC, dG, and biotin-dU.

FIG. 11 presents exemplary gel electrophoresis isolation of Hi-C libraries generated from a human and a yeast genome. PCR amplified 3C product is shown for comparative purposes.

FIG. 17A: Cells are cross-linked with formaldehyde, resulting in covalent links between spatially adjacent chromatin segments (DNA fragments: dark blue, red; Proteins, which can mediate such interactions, are shown in light blue and cyan). Chromatin is digested with a restriction enzyme (here, HindIII; restriction site: dashed line, see inset) and the resulting sticky ends are filled in with nucleotides, one of which is biotinylated (purple dot). Ligation is performed under extremely dilute conditions to create chimeric molecules; the HindIII site is lost and a NheI site is created (inset). DNA is purified and sheared. Biotinylated junctions are isolated with streptavidin beads and identified by paired-end sequencing.

FIG. 17B: A genome-wide contact matrix, wherein the submatrix corresponds to intrachromosomal interactions on chromosome 14. Each pixel represents all interactions between a 1 Mb locus and another 1 Mb locus; intensity corresponds to the total number of reads (0-50). Tick marks appear every 10 Mb.

FIG. 17C: Comparison of an original experiment to a biological repeat using the same restriction enzyme (range: 0-50 reads)

FIG. 17D: Comparison of an original experiment to a biological repeat using a different restriction enzyme (range: 0-100 reads, NcoI).

FIG. 18A: Probability of contact decreases as a function of genomic distance on chromosome 1, eventually reaching a plateau at ~90M (blue). The level of interchromosomal contact (black dashes) differs for different pairs of chromosomes; loci on chromosome 1 are most likely to interact with loci on chromosome 10 (green dashes) and least likely to interact with loci on chromosome 21 (red dashes). Interchromosomal interactions are depleted relative to intrachromosomal interactions.

FIG. 18B: Observed/expected number of interchromosomal contacts between all pairs of chromosomes. Red indicates enrichment, and blue indicates depletion (up to twofold). Small, gene-rich chromosomes tend to interact more with one another.

FIG. 19A: A map of chromosome 14 at a resolution of 1 Mb (1 tick mark=10 Mb) exhibits substructure in the form of an intense diagonal and a constellation of large blocks (three experiments combined, range: 0-200 reads).

FIG. 19B: An observed/expected matrix showing loci with either more (red) or less (blue) interactions than would be expected given their genomic distance (range: 0.2-5).

FIG. 19C: A correlation matrix illustrating a correlation (red: 1, blue: −1) between the intrachromosomal interaction profiles of every pair of 1 Mb loci along chromosome 14. The plaid pattern indicates the presence of two compartments within the chromosome.

FIG. 19D: An interchromosomal correlation map for chromosome 14 and chromosome 20 (red: 0.25, blue: −0.25). The unalignable region around the centromere of chromosome 20 is indicated in grey. Each compartment on chromosome 14 has a counterpart on chromosome 20 with a very similar genome-wide interaction pattern.

FIG. 19E: Display of probes alternating between Compartment A (L1 and L3) and Compartment B (L2 and L4) to four consecutive loci along Chromosome 14. L3 (blue) was consistently closer to L1 (green) than to L2 (red), despite the fact that L2 lies between L1 and L3 in the primary sequence of the genome. This was confirmed visually and by plotting the cumulative distribution.

FIG. 19F: Display of probes alternating between Compartment A (L1 and L3) and Compartment B (L2 and L4) to four consecutive loci along Chromosome 14. L2 (red) was consistently closer to L4 (green) than to L3 (blue).

FIG. 19G: A correlation map of chromosome 14 at a resolution of 100 kb. The principal component (eigenvector) correlates with the distribution of genes and with features of open chromatin.

FIG. 19H: A 31 Mb window from the chromosome 14 is shown; the indicated region (yellow dashes) alternates between the open and closed in compartment in GM06990 (top, eigenvector and heatmap), but is predominantly open in K562 (bottom, eigenvector and heatmap). The change in compartmentalization corresponds to a shift in chromatin state (DNAseI).

FIG. 21A: L5 (green) was, in general, closer to L7 (blue) than to L6 (red), despite the fact that L5 is closer to L6 than to L7 in the primary sequence of the genome. These results were observed both visually (right) and by plotting the cumulative distribution (middle).

FIG. 21B: L6 (red) was consistently closer to L8 (green) than to L7 (blue).

FIG. 27A: Reads from fragments corresponding to both intrachromosomal (blue) and interchromosomal (red) interactions align significantly closer to HindIII restriction sites as compared to randomly generated reads (green). Both the intrachromosomal reads and interchromosomal reads curves decrease rapidly as the distance from the HindIII site increases until a plateau is reached at a distance of ~500 bp. This corresponds to the maximum fragment size used for sequencing.

FIG. 27B: Hi-C sequences are expected to point (5'-3') in the direction of the ligation junction and therefore should align in the linear genome to the 3' end of HindIII restriction fragments. This tendency is reflected in ~80% of reads from both intrachromosomal (blue) and interchromosomal (red) interactions.

FIG. 43 presents several embodiments of equilibrium and fractal globules. The polymer is colored in rainbow shades from red to blue along its contour length. Equilibrium globules demonstrate extensive mixing of the regions that are distant along the chain (have different colors). Fractal globules, in contrast, exhibit large monochromatic blocks, demonstrating little mixing of distant regions.

FIG. 45 present representative subchains within fractal and equilibrium globules have vastly differing conformations. In a fractal globule, subchains correspond to compact spatial territories (left). In an equilibrium globule, subchains of a comparable size will wander randomly throughout the conformation; their spatial extent is equivalent to that of the globule as a whole.

FIG. 48 presents representative fractal globules expanding readily when the compressive potential is removed; equilibrium globules remain tightly knotted. Here, examples are presented at the same size scale after an equal number of steps in the absence of a compressive potential. The fractal globule expands dramatically; the equilibrium globule is arrested early in its expansion due to knotting.

FIG. 51 presents exemplary data showing a comparison of a finite iteration of a Peano Curve (specifically, the Hilbert Curve) with an ordinary Hamiltonian Path in two dimensions. The former is analogous in structure to the fractal globule; the latter to an equilibrium globule. There is a stronger correspondence between one-dimensional position and d-dimensional position in the Hilbert Curve. In d>2, Hamiltonian paths are highly knotted.

FIG. 52A: Contact probability as a function of genomic distance, averaged across the genome (blue) shows a power law scaling between 500 kb and 7 Mb (shaded region) with a slope of −1.08 (fit shown in cyan).

FIG. 52B: Simulation results for contact probability as a function of distance (1 monomer~6 nucleosomes~1200 bp, SOM) for equilibrium (red) and fractal (blue) globules. The slope for a fractal globule is very nearly −1 (cyan), confirming our prediction (SOM). The slope for an equilibrium globule is −3/2, matching prior theoretical expectations. The slope for the fractal globule closely resembles the slope we observed in the genome.

FIG. 52C: Top: An unfolded polymer chain, 4000 monomers (4.8 Mb) long. Coloration corresponds to distance from one endpoint, ranging from blue to cyan, green, yellow, orange, and red. Middle: An equilibrium globule. The structure is highly entangled; loci that are nearby along the contour (similar color) need not be nearby in 3D. Bottom: A fractal globule. Nearby loci along the contour tend to be nearby in 3D, leading to monochromatic blocks both on the surface and in cross-section. The structure lacks knots.

FIG. 52D: Genome architecture at three scales. Top: Two compartments, corresponding to open and closed chromatin, spatially partition the genome. Chromosomes (blue, cyan, green) occupy distinct territories. Middle: Individual chromosomes weave back-and-forth between the open and closed chromatin compartments. Bottom: At the scale of single megabases, the chromosome consists of a series of fractal globules.

DETAILED DESCRIPTION OF THE INVENTION

Figure 1:
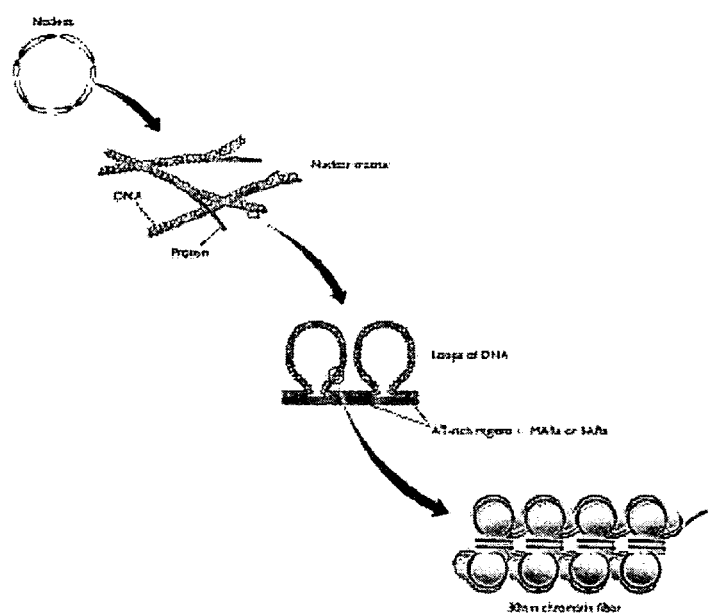
FIG. 1 illustrates a sequential expanding view of a representative nucleus, nuclear matrix, DNA loops, and chromatin fiber structure.

The present invention is related to the field of genomic interactions and methods of detecting genomic interactive pathways. This detection method allows rapid and exhaustive analysis of chromosomal interactions throughout complete genomes, which allows unbiased identification of regulatory elements, and interactions between them, in any genome (ranging from prokaryotes to higher eukaryotes including human), in different cell types and in both normal and disease states. The method can be used to characterize and differentiate disease states from normal states, and can be used to assess effects of therapeutic interventions on genome regulation and function. The method can also be used as a diagnostic by detecting disease-correlated chromosome conformations.

In one embodiment, the present invention contemplates a method comprising probing a three-dimensional architecture of whole genomes by coupling proximity-based ligation with massively parallel sequencing. In one embodiment, the method comprises constructing spatial proximity maps of a genome (i.e., for example, the human genome) at a 1 Mb resolution. In one embodiment, the proximity maps confirm the presence of chromosome territories and the spatial proximity of small, gene-rich chromosomes.

The data presented herein demonstrates an identification of an additional level of genome organization that is characterized by a spatial segregation of open and closed chromatin to form two genome-wide compartments. Although it is not necessary to understand the mechanism of an invention, it is believed that, at a megabase scale, the chromatin conformation is consistent with a fractal globule. In one embodiment, a fractal globule is a knot-free conformation that enables maximally dense packing while preserving the ability to easily fold and unfold any genomic locus. It is further believed that a fractal globule is distinct from a more commonly used globular equilibrium model. The data presented herein demonstrate a method (i.e., for example, a Hi-C method) having sufficient power to map dynamic conformations of whole genomes.

I. Genomic Conformational Structure

Reports suggest that three-dimensional conformation of chromosomes may be involved in compartmentalizing the nucleus and bringing widely separated functional elements into close spatial proximity. Cremer et al., *Nat Rev Genet* 2:292 (2001); Sexton et al., *Nat Struct Mol Biol* 14:1049 (2007); Dekker J., *Science* 319:1793 (2008); Misteli T., *Cell* 128:787 (2007); and Kosak et al., *Genes Dev* 18:1371 (2004). Understanding how chromosomes fold can provide insight into the complex relationships between chromatin structure, gene activity, and the functional state of the cell. Yet beyond the scale of nucleosomes, currently little is known about chromatin organization.

Because deoxyribonucleic acid (DNA) is a linear molecule, the genome is often thought of as linear. But chromosomes are not rigid, and so the spatial distance between two genomic loci need not correspond to their distance along the genome. Regions separated by many megabases can be immediately adjacent in 3-dimensional space. From the standpoint of regulation, understanding long-range interactions between genomic loci may be useful. For example, gene enhancers, silencers, and insulator elements might possibly function across vast genomic distances.

Like the higher-level organization of proteins, the bending and folding of DNA and chromatin create functionally significant structures at a wide variety of scales. At small scales, it is well known that DNA is often wound around proteins such as histones to create a structure known as the nucleosome. These nucleosomes pack into larger 'chromatin fibers', and it is believed that the packing pattern is affected by cellular processes such as transcription.

Functional structures also exist at far larger scales; regions separated by many megabases can be immediately adjacent in 3-dimensional space. From the standpoint of regulation, long-range interactions between genomic loci may play a role: for example, gene enhancer, silencer and insulator elements may all function across vast genomic distances and their primary mode of action could involve a direct physical association with, for example, target genes, noncoding RNAs and/or regulatory elements. Long-range interactions are not limited to elements located in cis, i.e. along the same chromosome, but also occur between genomic loci located in trans, i.e. on different chromosomes.

The existence of long-range interactions complicates efforts to understand the pathways that regulate cellular processes, because the interacting regulatory elements could lie at a great genomic distance from a target gene, even on another chromosome. In the case of oncogenes and other disease-associated genes, identification of long-range genetic regulators would be of great use in identifying the genomic variants responsible for the disease state and the process by which the disease state is brought about.

In one embodiment, the present invention contemplates a method detecting close proximity between a first polynucleic acid region and a second polynucleic acid region. In general, a nucleus comprises a roughly spherical amorphous condensation comprising a nuclear matrix. It is generally believed that a nuclear matrix is composed of chromosomes comprising two strands of hybridized deoxyribonucleic acid (DNA) to which regulatory proteins may attach. One of the DNA strands may be considered a sense strand and comprise DNA loops that are generated by AT-rich regions (i.e., for example, matrix attachment regions (MARS) or scaffold-attachment regions (SARS). The three-dimensional structure of such DNA loops form a chromatin fiber providing a spheroid chromosomal surface that enhances surface availability for regulatory protein binding. See, FIG. 1.

Figure 2:
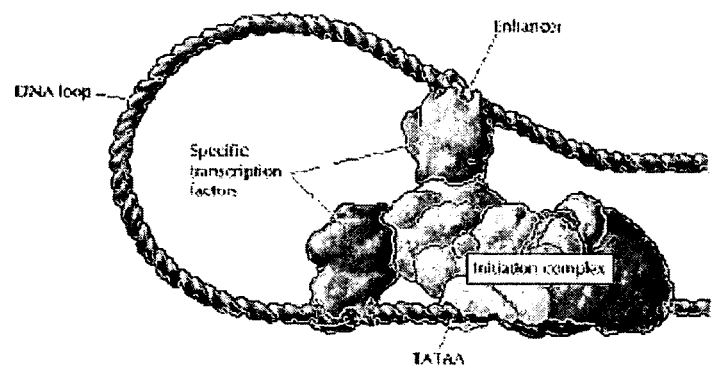
FIG. 2 illustrates one possible intrasequence binding region wherein a transcription initiation complex comprises at least two specific transcription factors having binding to long range genomic locations to regulate transcription of a coding sequence (TATAA: start codon).

The present invention contemplates that the spheroid chromosomal surface also enhances surface availability for binding between a first and second region of the same DNA sequence. Such intrasequence binding need not represent the entire length of a chromosome (i.e., long range interaction), as the tertiary structure within a localized chromosomal area may provide sufficient flexibility for close proximity intrasequence binding to occur. In one embodiment, the present invention contemplates a method that measures intra- and interchromosomal interactions that regulate transcription by regulatory elements. In one embodiment, the intrachromosomal regulatory elements may include, but are not limited to, enhancers, silencer, or insulators. Although it is not necessary to understand the mechanism of an invention, it is believed that such intra- or interchromosomal interactions involve regulatory elements that may account for conserved non-coding elements (CNEs). In one embodiment, the present invention contemplates a method providing a transcription complex comprising a first and second specific transcription factor and an open reading frame sequence (i.e., for example, containing a TATAA binding region) for creating an intra- or interchromosomal binding complex. In one embodiment, the second transcription factor comprises an enhancer, capable of binding to an intrachromosomal DNA sequence. See, FIG. 2.

II. 3C-5C Technology

Figure 3:
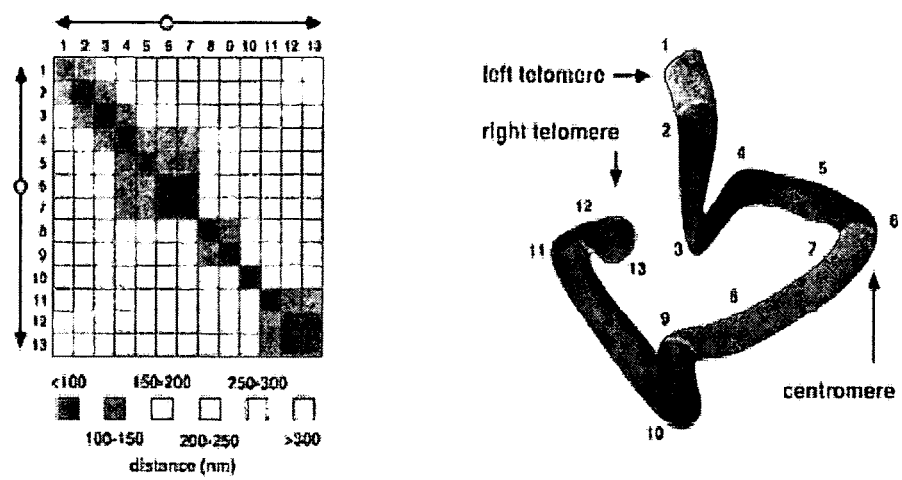
FIG. 3 illustrates exemplary data from a 3C library analysis identifying intrasequence interaction rates as a function of chromosomal region.

The identification of intra- or interchromosomal interaction between genomic loci was made possible by Chromosome Conformation Capture (3C) technology. Dekker et al., "Capturing chromosome conformation" *Science* 295:1306-1311 (2002). In brief, 3C technology creates a 3C library for PCR amplification and sequencing by i) crosslinking nuclear matrix so that genomic loci that are in close spatial proximity become linked; ii) digesting away the intervening DNA loop between the crosslink; iii) ligating & reverse crosslinking the intrasequence regions for addition to a 3C library. The construction of a 3C library thereby provides an ability to identify the frequency of interactions between specific (i.e., known) intrasequence regions. The library creates a matrix capable of estimating chromosomal geometry by plotting interaction rates. Higher interaction rates are observed between areas that are physically closer. See, FIG. 3.

Long-range interactions between specific pairs of loci can also be evaluated with Chromosome Conformation Capture (3C), using spatially constrained ligation followed by locus-specific PCR. Dekker et al., *Science* 295:1306 (2002). Adaptations of 3C have extended the process with the use of inverse PCR (4C). Simonis et al., *Nature Genetics* 38:1341-1347 (2006); and Zhao et al., *Nature Genetics* 38:1348-1354 (2006) or multiplexed ligation-mediated amplification (5C). Dostie et al., *Genome Research* 16:1299-1309 (2006). Each of these previous technologies share at least one disadvantage including, but not limited to: i) requiring prior knowledge of at least one genomic locus (i.e., for example, choosing a set of target loci) that is hypothesized to be involved in long-range interactions; and ii) not allowing unbiased genomewide analysis.

In some embodiments, the present invention contemplates a Hi-C technology that improves upon these techniques and overcomes this major limitation by providing a completely unbiased (i.e., for example, no known sequence is required) and truly genome-wide methodology for identifying and quantifying interactions between any pair of genomic loci.

3C technology has demonstrated that long-range interactions between genomic loci play a role in genome control. For example, enhancers, promoters, insulator/boundary elements and other types of regulatory elements all are found to engage in specific long-range interactions to control specific aspects of genome activity such as gene transcription, chromosome condensation, genome stability, imprinting and dosage compensation.

The 4C technology builds upon the 3C technology but provides an ability to find all loci interacting with a given target sequence, as opposed to only detecting whether an interaction is present. Zhao et al., (supra). In contrast, the 5C technology finds interactions between a specified set of loci. Dostie, (supra). In particular, the 5C technology became burdensome when scaled up to evaluate mammalian genomes. For example, in 5C analysis, the number of utilized primers must equal the number of loci to be evaluated. Currently, the 5C matrix is limited to a 200×200 sequence array, therein only 40,000 possible interactions can be identified.

III. The Hi-C Protocol

Figure 17:
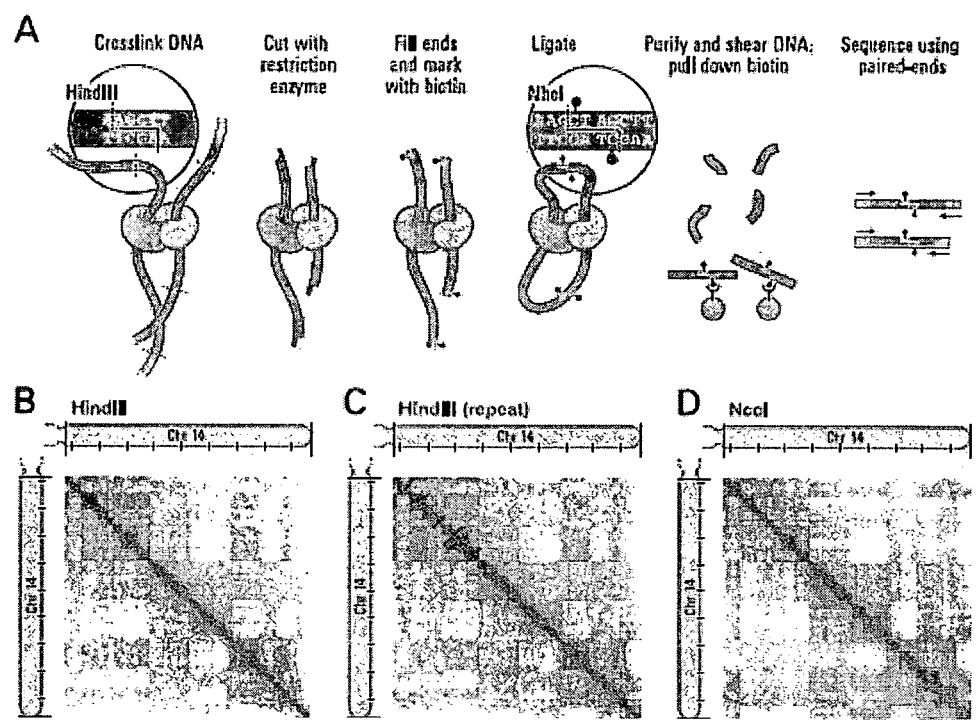
FIG. 17 presents a flow pathway of one embodiment of a Hi-C method.

In one embodiment, the present invention contemplates a method (i.e., for example, a Hi-C method) comprising purifing ligation products followed by massively parallel sequencing. In one embodiment, a Hi-C method allows unbiased identification of chromatin interactions across an entire genome. In one embodiment, the method may comprise steps including, but not limited to, crosslinking cells with formaldehyde; digesting DNA with a restriction enzyme that leaves a 5'-overhang; filling the 5'-overhang that includes a biotinylated residue; and ligating blunt-end fragments under dilute conditions wherein ligation events between the cross-linked DNA fragments are favored. In one embodiment, the method may result in a DNA sample containing ligation products consisting of fragments that were originally in close spatial proximity in the nucleus, marked with the biotin residue at the junction. In one embodiment, the method further comprises creating a library (i.e, for example, a Hi-C library). In one embodiment, the library is created by shearing the DNA and selecting the biotin-containing fragments with streptavidin beads. In one embodiment, the library is then analyzed using massively parallel DNA sequencing, producing a catalog of interacting fragments. See, FIG. 17A.

The data presented herein demonstrates the creation of a Hi-C library from a karyotypically normal human lymphoblastoid cell line (GM06990) that was sequenced on two lanes of an Illumina Genome Analyzer. 8.4 million read pairs were generated that could be uniquely aligned to the human genome reference sequence; of these, 6.7 million corresponded to long-range contacts between segments greater than >20 Kb apart.

One distinctive advantage between Hi-C technology and prior methods, including 3C, 4C, 5C, and 6C, is that the latter are hypothesis-driven approaches that target specific loci (3C, 4C, 5C) or loci bound by a specific protein (6C). Hi-C can provide unbiased coverage of entire genomes (i.e., sequencing is performed after interaction identification, not before). Hi-C is also compatible with a broader array of fragmentation schemes (e.g. is not limited to restriction digestion as are 3C, 4C, 5C and 6C), enabling the examination of spatial organization of genomes, or segments of genomes, at many different scales. Finally, Hi-C does not require large numbers of organism-, target-, or restriction enzyme-specific primers; a small set of common reagents can be used for a wide variety of experiments.

In summary, the Hi-C technique involves conventional DNA fragmentation protocols (i.e., for example, restriction enzyme fragmentation) but includes novel marking of ligation junctions using, for example, a biotinylated linker. The resulting biotinylated ligation junction can then be purified by streptavidin pulldown and then sequenced. The data shown herein shows that the Hi-C technology enables genome-wide identification of long-range interactions in vivo in an unbiased fashion.

Figure 3A:
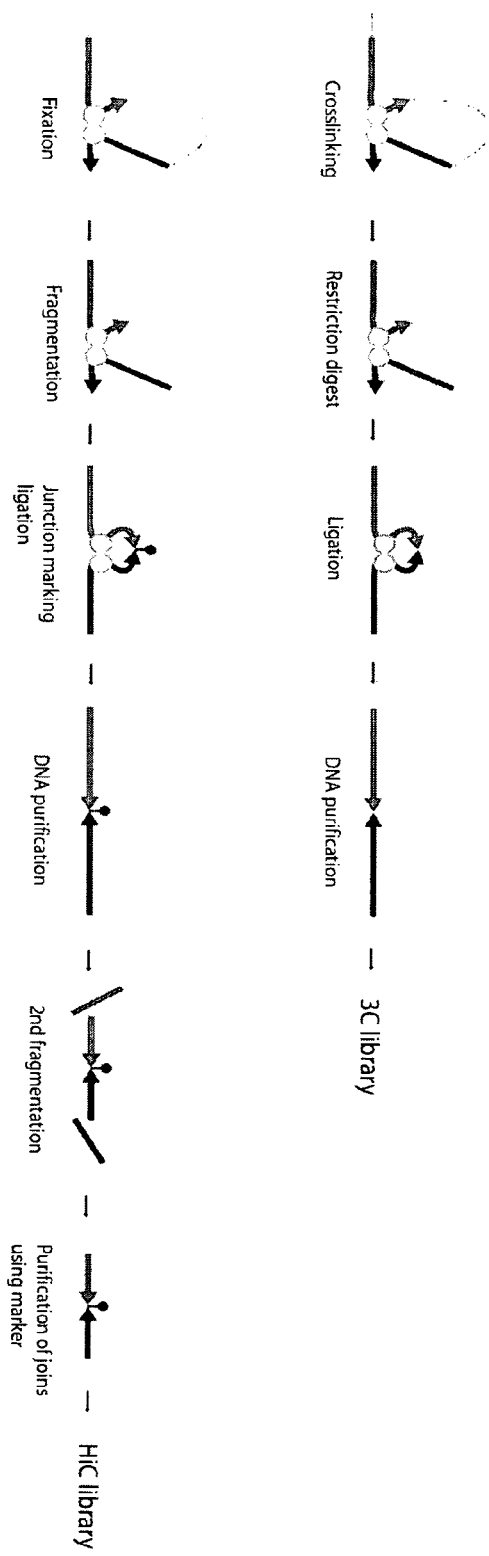
FIG. 3A presents one embodiment of differences between 3C and Hi-C technology. For example, Hi-C utilizes junction marking ligation instead of simple ligation followed by reverse crosslinking.

In some embodiments, the present invention contemplates an improved technology in which a 3C library is modified to a Hi-C library under conditions that nucleic acid sequencing may be automated (i.e., for example, by using a Solexa, Illumina, Inc.), instead of using multiple primer PCR techniques. For instance, shearing a 3C library can be used to generate a large population of oligonucleotides spanning join regions. See, FIG. 3A. In one embodiment, the present invention contemplates a method (i.e., for example, the Hi-C protocol) analyzing long-range physical interactions between loci in a genome. Although it is not necessary to understand the mechanism of an invention, it is believed that the method is not comparable to previous techniques (i.e., for example a 3C assay) due to a series of altered steps, modified steps, and/or additional steps. It is further believed that the Hi-C technology provides an improved and superior interaction analysis because it may be performed in an unbiased fashion and at a genome-wide scale, which is not possible using previously developed methods.

In one embodiment, the present invention contemplates a method for analyzing long-range interactions between loci in a genome at a genome wide scale. Although it is not necessary to understand the mechanism of an invention, it is believed that the method analyzes interactions between two loci that are far apart along the genome when considering the primary nucleic acid sequence order, but are actually close together in 3-dimensional structure of the genome in vivo, resulting from nucleic acid secondary and tertiary structures.

In one embodiment, DNA interactions may be immobilized by fixation (i.e., for example, with formaldehyde) wherein the fixative creates protein-protein crosslinks and/or protein-nucleic acid crosslinks. Although it is not necessary to understand the mechanism of an invention, it is believed that this fixation step preserves the in vivo co-location of genomic loci during subsequent processing in vitro [Step 1].

In one embodiment, the fixed DNA-protein complex may be fragmented (i.e., for example, by using a restriction enzyme) leaving behind DNA fragments comprising sticky ends [Step 2]. In one embodiment, the restriction enzyme comprises HindIII. In one embodiment, the fragmenting reaction is performed overnight.

In one embodiment, the ends of the fragments are partially filled in with only one nucleotide (i.e., for example, Klenow+dATP for approximately 30 minutes), thereby creating a fragment comprising non-sticky (i.e., for example, non-complementary) ends. [Step 3] In one embodiment, the sticky end comprises an overhang sequence:

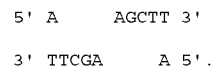

In one embodiment, the non-sticky end comprises an overhang sequence:

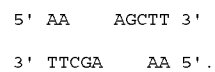

Although it is not necessary to understand the mechanism of an invention, it is believed that this step will prevent the DNA fragments from ligating to each other in the next step, without the addition of a junction marker (i.e., for example, a marked linker sequence). See, FIG. 3B. The restriction enzymes are then deactivated by heating in sodium dodecylsulfate (SDS). [Step 4].

Figure 4:
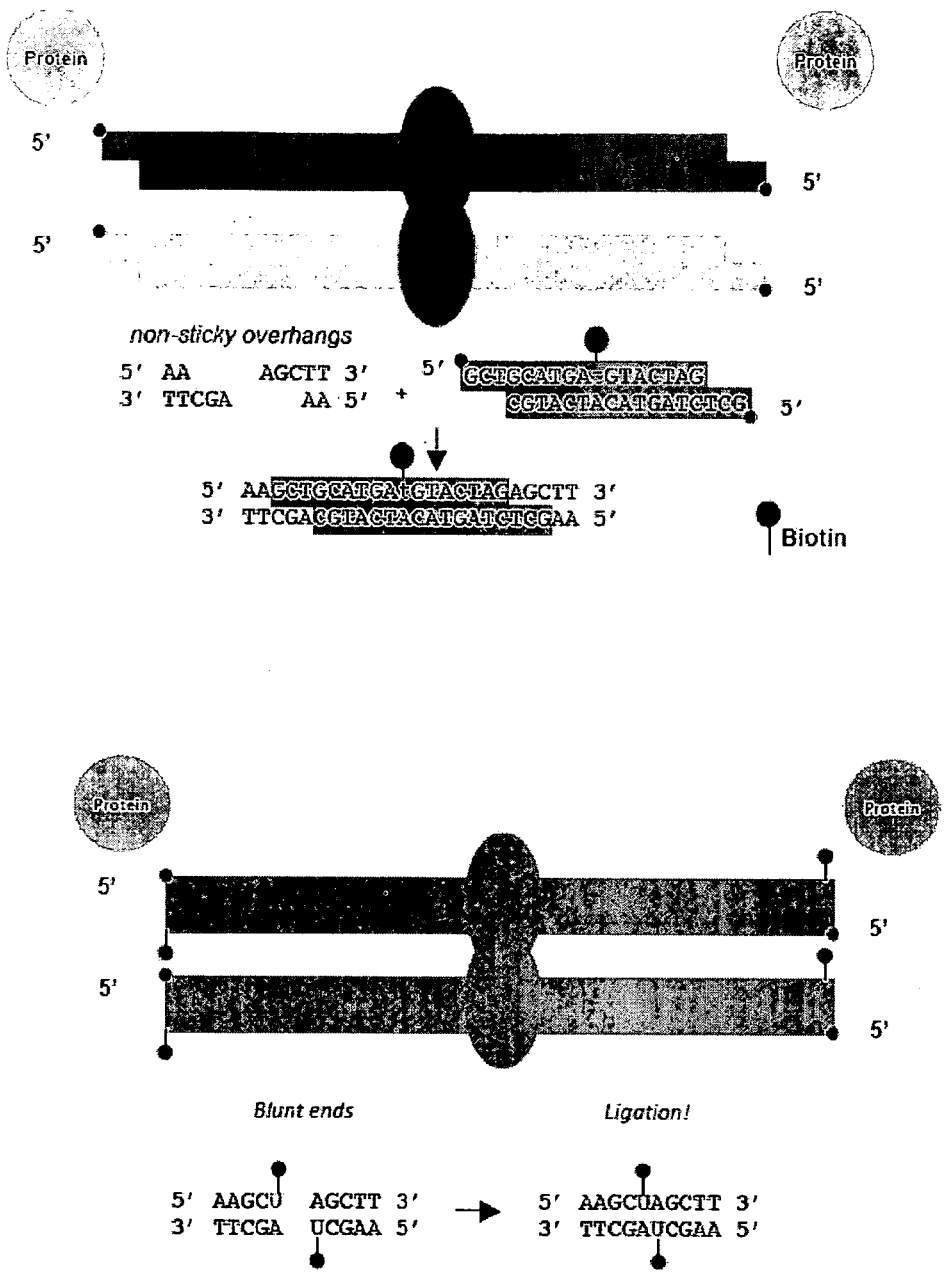
FIG. 4 presents two embodiments of a Hi-C ligation step. Top Panel: Using a biotinylated linker. Bottom Panel: Using blunt end biotin-dU marked DNA fragments.

In one embodiment, a short biotinylated linker sequence complementary to the filled-in restriction fragments is ligated to the DNA non-complementary ends so that the DNA non-complementary ends are joined together [Step 5]. See, FIG. 4. Although it is not necessary to understand the mechanism of an invention, it is believed that because of the prior fixation step, the joining of two DNA fragments using a junction marker has a high likelihood of occurring between two genomic loci which are far apart on the genome, but nearby in 3-dimensional space. Such linkages (i.e., joinings) between two genomic loci are termed 'joins'. Note, that because the DNA fragments were partially filled-in according to Step 3, the DNA ends are rendered non-complementary and are thereby favored to form joins between the genomic fragments (i.e., for example, when a labeled linker is incorporated). In summary, joins represent genomic interactions between separated genomic loci in vivo, as a result of the fixation and fragmentation process.

In one embodiment, the protein-protein and protein-DNA crosslinks are de-crosslinked by overnight heating thereby releasing the ligated DNA fragments. [Step 6].

In one embodiment, residual protein is digested using proteinase K followed by DNA purification by phenol extraction and ethanol precipitation. [Step 7]

In one embodiment, the junction marker and flanking DNA excision is performed by sonication of the join into short fragments, wherein a first subset of the fragments comprises the marker (i.e., for example, biotin) and a second subset of the fragments do not comprise the marker [Step 8].

In one embodiment, the DNA ends of each fragment are processed using T4 polymerase, kinase, and Klenow followed by size selection of both the marked fragments and the non-marked fragments using gel electrophoresis. [Step 9]

In one embodiment, the marked fragments are subjected to selective purification. For example, nucleic acids marked with biotin may be captured via the biotinylated linkers onto streptavidin beads [Step 10]. Although it is not necessary to understand the mechanism of an invention it is believed that the resulting fragments contain ligation junctions, so the two ends of the fragment come from either side of a ligation event.

Figure 5:
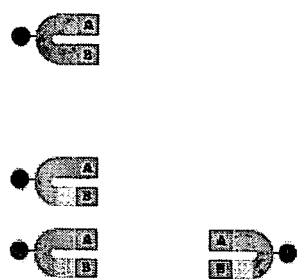
FIG. 5 presents one embodiment of the attachment of sequence adapters (i.e., for example, A and B) to biotin fragments.

In one embodiment, the marked fragments are ligated to paired-end sequencing adapters to create a sequencing library (i.e., for example, Solexa or 454 sequencing adapters, designated, for example, A and B). [Step 11] See, FIG. 5.

In one embodiment, the marked fragments comprising sequencing adapters are amplified by polymerase chain reaction, wherein non-marked amplified product DNA is created. [Step 12].

In one embodiment, the non-marked amplified product DNA comprising sequencing adapters are subjected to high-throughput sequencing (i.e., for example, Solexa or 454) [Step 13]. In one embodiment, the sequence adapters are paired-end sequencing primers. In one embodiment, the sequencing primer comprises sequence adapter A. In one embodiment, the sequencing primer comprises sequence adapter B. In one embodiment, a 454 sequencing system is used, wherein 250-mer reads are long enough to read through the linker and obtain sequence information from both sides of the join. In one embodiment, a Solexa sequencing system is used, wherein paired-end 36-mers may be obtained from both sides of the linker.

Although it is not necessary to understand the mechanism of an invention, it is believed that analysis by either a 454 sequencing system or Solexa sequencing system provides enough sequence from both sides of the join to uniquely align the pair of sequence fragments back to the genome. It is further believed that when the sequence fragments from both sides of the linker are found to lie at a great distance in the genome, this provides strong evidence for the existence of a long-range interaction between the implicated loci.

Other embodiments of the above basic protocol are also contemplated by the present invention. Table 1.

TABLE 1

Alternative Embodiments To The Basic Hi-C Technology

| Step | Preferred Embodiment | Alternative Embodiments |
|---|---|---|
| Fixation | Formaldehyde | 1) Dimethyl Suberimidate<br>2) BS3<br>3) EDC<br>4) UV light (using appropriate amino acid analogs) |
| Fragmentation | Restriction with HindIII | 1) Restriction<br>2) Digestion with non-specific nucleases (i.e. MNase)<br>3) Sonication |
| Junction-marking Ligation | Biotinylated linker | 1) Blunting w/biotinylated bases followed by blunt-end ligation<br>2) Annealing of sticky ends; nick translation; ligation<br>3) Primer-containing linker<br>4) Linker marked with histidine moiety<br>5) Optional clean-up of non-ligated, marked DNA fragments: exonuclease treatment |
| Purification | Streptavidin Pulldown | 1) PCR amplification (if junction is marked with primers)<br>2) Nickel Chelation (if junction is marked with histidine)<br>3) Additional purification: ChIP using antibodies directed against proteins of interest. |
| Analysis | Paired-end Illumina Sequencing | 1) 454 Sequencing (or other sequencing modality)<br>2) Microarray hybridization<br>3) qPCR (or other PCR-based technique) |

Junction marking ligation can be accomplished by a number of different methods. Although it is not necessary to understand the mechanism of an invention, it is believed that one advantage of junction marking is to provide "a handle" at the point of genomic interaction, such that extraction and isolation of the interaction is possible. One method is to incorporate at the genomic interaction site either an individually labeled nucleotide base or a labeled nucleic acid linker sequence (i.e., for example, linkers). Such labeled nucleotide bases and/or linkers are labeled with an affinity marker (i.e., for example, biotin, histidine, or FLAG). When using a linker sequence, gel electrophoresis will detect a shift in molecular weight position when comparing the data to a 3C assay. However, when only using a modified and/or labeled base (i.e., for example, a nucleotide), the shift is too small to detect.

Another method for junction marking ligation is to incorporate modified bases at the genomic interaction site by nick translation. Nick translation may use specific polymerases to replace nucleotides with tagged nucleotides. After replacement, a ligase is used to repair the nick. Two methods of detecting a nick-translated DNA strand compatible with the present invention include, but are not limited to, fluorescence or blotting. When using the technique, as one nucleotide base is substituted with a modified base, gel electorphoresis comparison to a 3C technology will not detect any shift in molecular weight.

The insertion of primers at the genomic interaction site may result in junction marking ligation. These primers may be of a specific and known sequence, or a universal primer. After the joins are isolated, the interaction junctions may be identified by performing PCR using a second set of primers that are complementary to the inserted primers, thereby extracting (i.e, for example, copying) and amplifying the entire junction sequence.

Figure 5A:
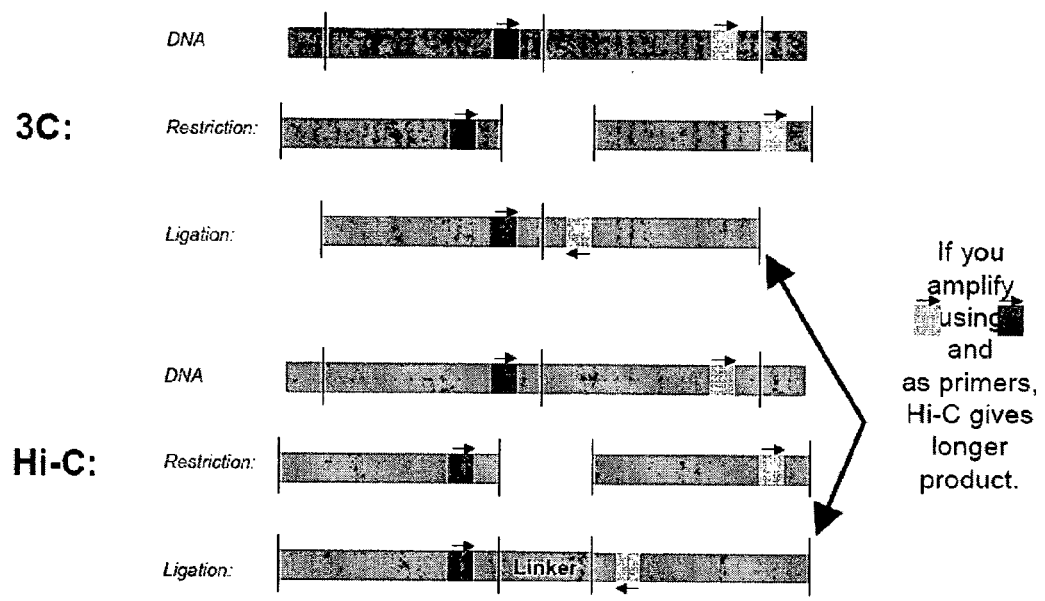
FIG. 5A compares the product lengths between the 3C and Hi-C technologies, using the 3C data as a positive control to show ligation between nearby segments, demonstrating that Hi-C can yield a longer product length due to incorporation of a junction marker.

Hi-C technology provides advantages over the 3C technology in that because a junction marker can be ligated between the disparately located fragments, thereby providing a longer product for analysis. Ligation products between closely located fragments (i.e., for example, those within a few kilobases along the linear genome sequence) are common in 3C. Because the Hi-C fixation protocol used was very similar to the fixation step in 3C, nearby fragments should tend to ligate, and be detectable by Hi-C. In some embodiments, additional linkers may be included to mark the ligation junction ensuring that the Hi-C ligation product is longer than the 3C ligation product. See, FIG. 5A. Although it is not necessary to understand the mechanism of an invention, it is believed that when nick translation is used to mark and/or label a join, the ligation product is not longer and does not result in a gel electrophoretic band shift in comparison to positive control 3C analysis.

Since the PCR amplification of both 3C and Hi-C products can be accomplished with the same primers, it is useful to compare the results of both procedures in order to verify that the junction marker is being incorporated into the ligation products. As expected, PCR analysis on the Hi-C library shows a shifted PCR product, demonstrating that the junction marker is efficiently incorporated into the ligation products (infra). As such, it is processed more efficiently and therefore more accurately.

Figure 6:
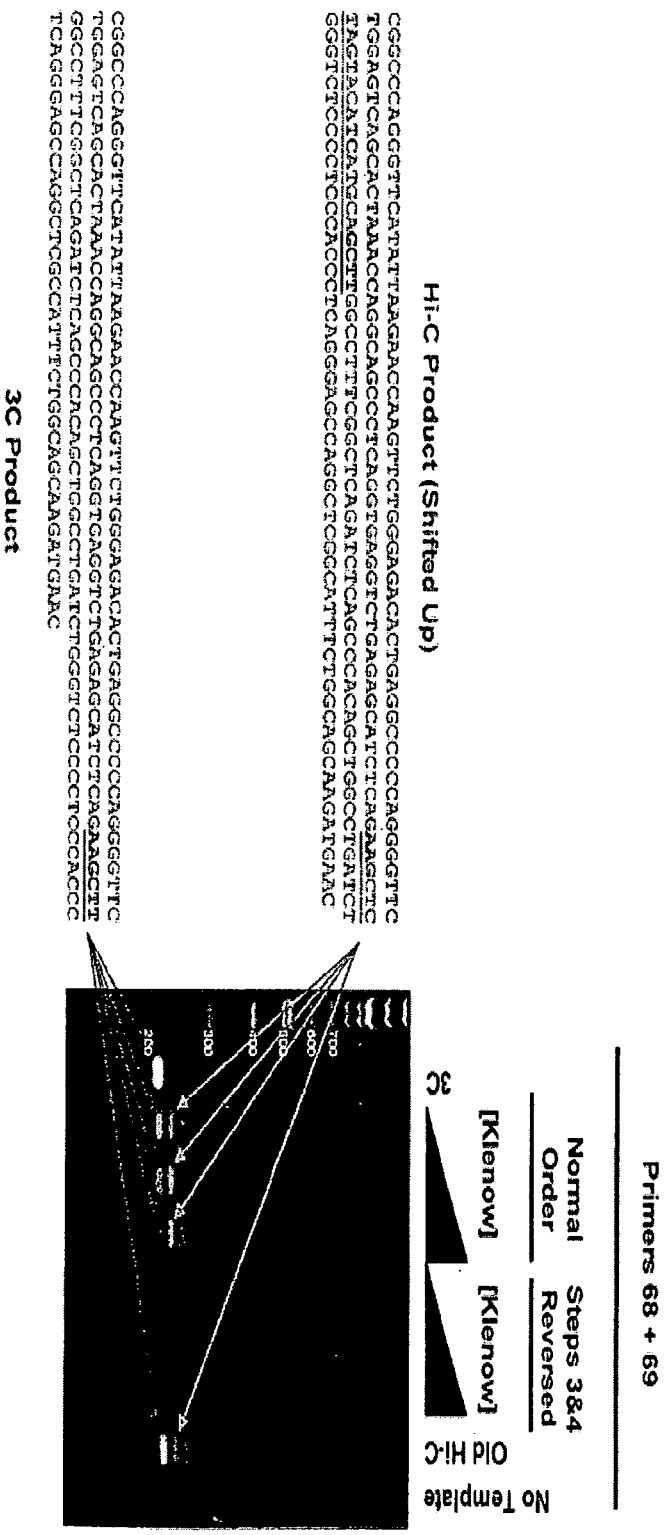
FIG. 6 presents exemplary gel electrophoresis isolation of DNA fragments comparing molecular weights of PCR amplified 3C product and linker-containing Hi-C product. The up-shifted Hi-C product multiple banding patterns indicate linker integration. Exemplary Sanger sequencing data confirming that the Hi-C product integrated the linker sequences by comparison to PCR amplified 3C product (left side).
Figure 7:
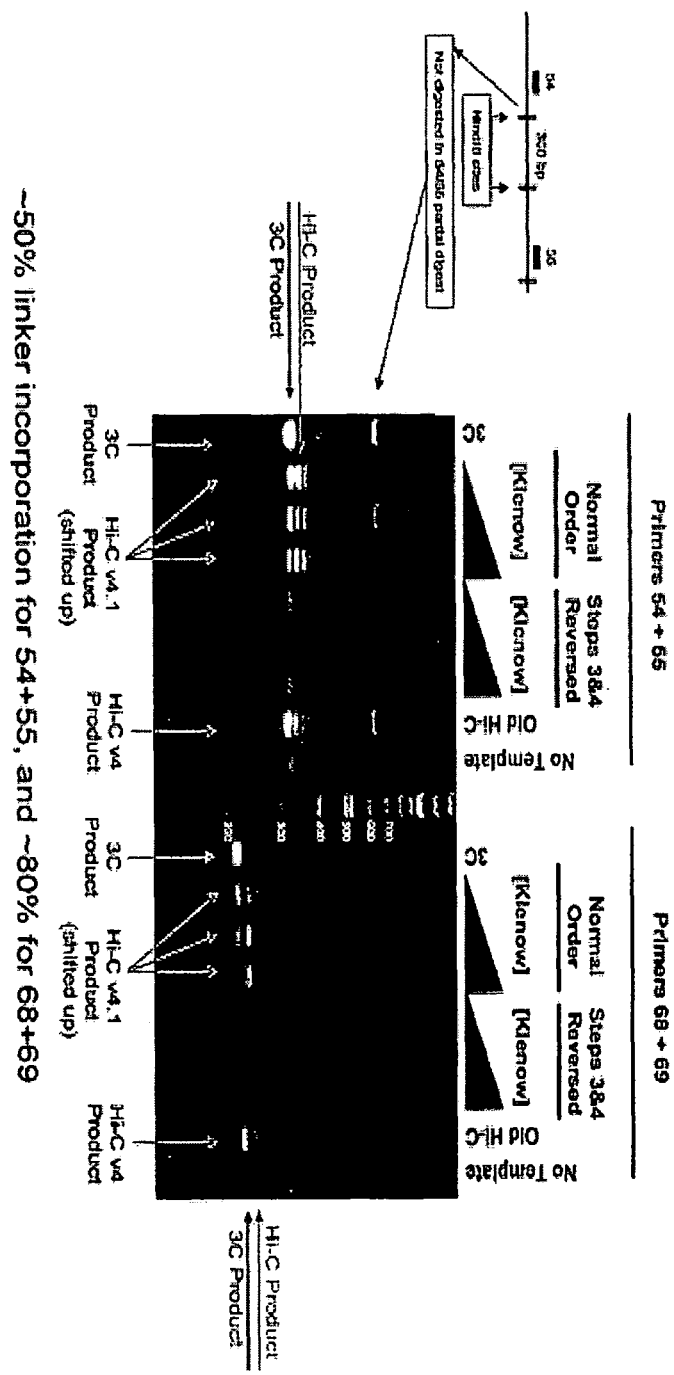
FIG. 7 presents exemplary gel electrophoresis isolation of DNA fragments comparing the molecular weights of PCR amplified 3C product and linker-containing Hi-C product, after using two different primer pairs (i.e., primers 54 & 55 and primers 68 & 69)
Figure 8:
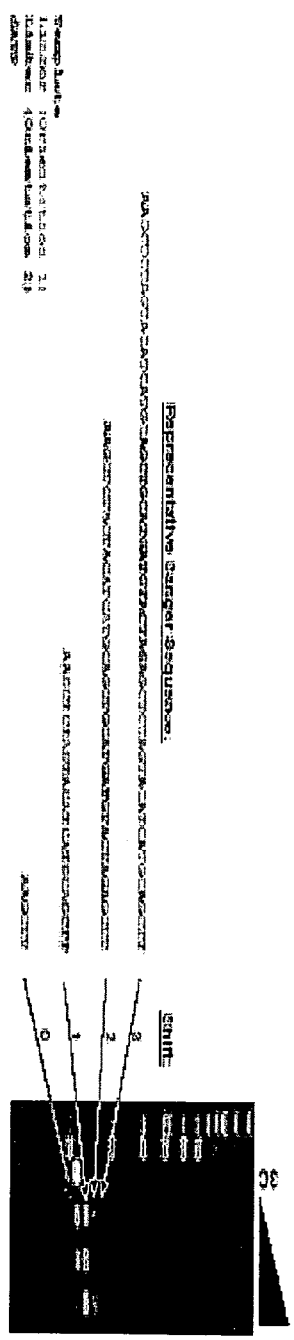
FIG. 8 presents exemplary Sanger sequencing data (left side) demonstrating that multimerization causes extra shifted bands thereby confirming multiple integration of the linker sequence into Hi-C products. Shift 0=no linkers; Shift 1=single linker; Shift 2=double linker; Shift 3=triple linker.

For example, Hi-C product fragments produced multiple banding patterns as opposed to the 3C single banding patterns, thereby providing evidence of junction marker incorporation into the amplified products. For example, a junction marker (i.e., for example, a biotinylated linker) integration into the Hi-C multiple product fragment banding is also reflected in the consistent molecular weight upshifting subsequent to gel electrophoresis isolation of the amplified products. See, FIG. 6. The data also show a high rate of linker incorporation when using the Hi-C technique: primers 54 and 55 demonstrated an approximate 50% linker incorporation, whereas Primers 68 and 69 demonstrated an approximate 80% linker incorporation. Further, linker incorporation into the amplified product was confirmed using Sanger sequencing. For example, the Primer 68 and 69 amplified products were compared between the Hi-C technique and 3C technique. The linker sequence was identified only in the up-shifted Hi-C electrophoretic bands. See, FIG. 7. The appearance of multiple Hi-C banding patterns was evaluated and determined to be a multimerization of incorporated linker sequences. For example, specific Sanger sequencing on each of the four bands obtained during creation of the Hi-C amplified product demonstrates: 0 Shift=addition of only a single adenosine to the sticky end; 1 Shift=addition of a single linker segment and a single adenosine to the sticky end; 2 Shift=addition of two linker segments and a single adenosine to the sticky end; and 3 Shift=addition of three linker segments and a single adenosine to the sticky end. Note that multimerization involves addition of multiple internal adenosines which mediate the multimerization of the linkers. See, FIG. 8.

Figure 9:
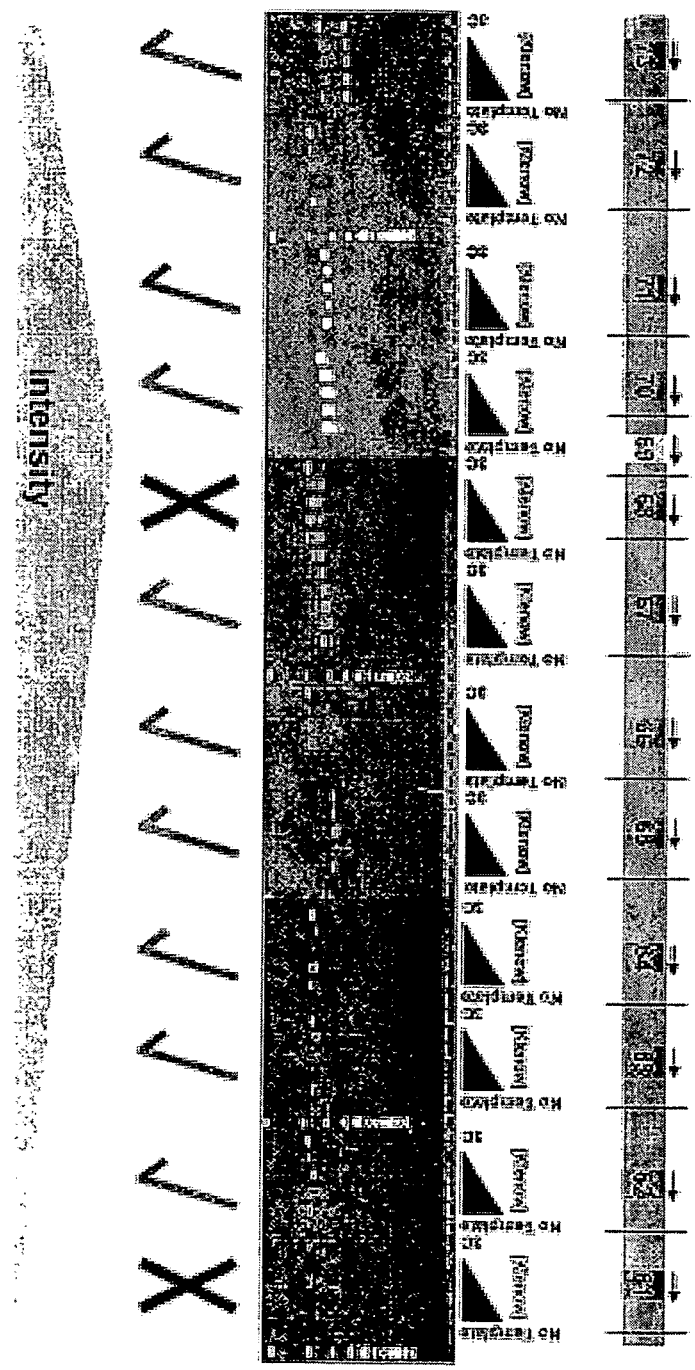
FIG. 9 presents exemplary gel electrophoresis isolation of Hi-C to 3C product comparisons using representative primer pairs. Primer 69 was successively paired with Primers 73-70 and 68-61, left to right.
Figure 10:
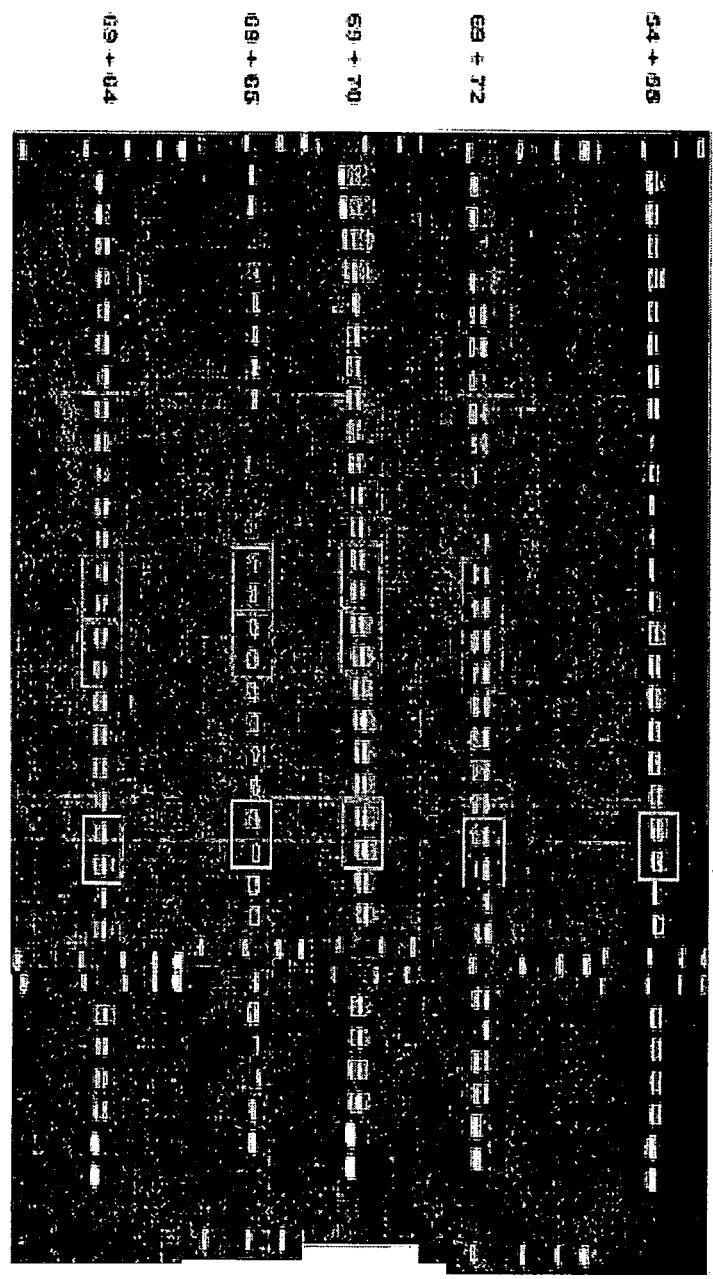
FIG. 10 presents exemplary gel electrophoresis isolation of Hi-C product showing reduced multimerization of linker incorporation in Primer pairs 69+64, 65, 70, or 72 and 54+55.

The Hi-C technique demonstrated a high level of reliability when comparing successive linker integrations using a variety of primer pairs. For example, Hi-C product was obtained when the technique was performed with Primer 69 paired successively with Primers 70-73 and 61-68. The Primer pairs 69+68 and 69+61 were observed not to provide an optimal result. See, FIG. 9. Although it is not necessary to understand the mechanism of an invention it is believed that optimization of the Hi-C technique may involve reduced generation of product sequences having more than one linker sequence. A close evaluation of data indicated that specific combinations of Primer 69 and the Primer pair 54-55 reduced linker multimerizations. See, FIG. 10.

Using the optimized techniques described above, Hi-C libraries derived from yeast and human samples were prepared. These libraries were then sequenced on a Solexa platform using a paired-end sequencing protocol. Each paired-end read corresponds to a ligation junction, and by aligning the two reads back to the genome, the identity of the two ligated fragments, and thus two co-located loci, can be determined. Thus the sequencing results enables computation of the ligation frequency of any two fragments (i.e., for example, HindIII fragments) in the yeast genome by inference co-location in three dimensions.

Figure 12:
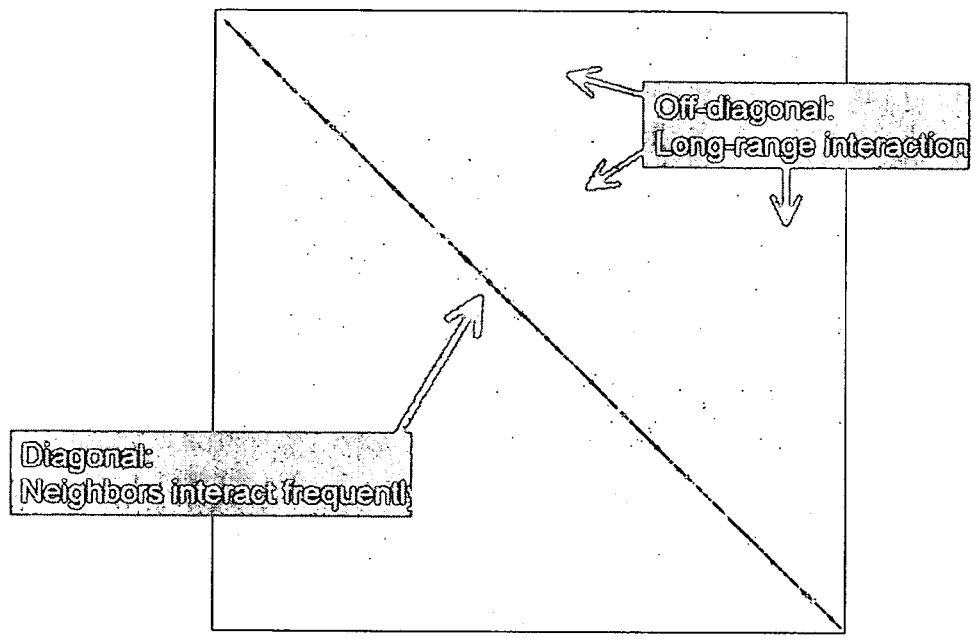
FIG. 12 presents exemplary Hi-C high throughput array heatmap data from yeast chromosome five (5) showing: i) products having infrequent long range interactions (off diagonal line) and ii) products having frequent close neighbor interactions (on diagonal line). Data points reflected by colored spots. The high throughput sequencing results enabled simultaneous examination of the frequency of all 192×192 (=36,864) possible Hi-C intrachromosomal interaction products from chromosome 5.

A subset of the Hi-C yeast results corresponding to intrachromosomal interactions within Chromosome 5 are presented using a heatmap analysis. See, FIG. 12. Each row and column corresponds to one of the 192 HindIII restriction fragments present along Chromosome 5. The intensity of each square corresponds to the number of paired-end reads indicating a ligation event between the two corresponding fragments (i.e., for example, maximum intensity corresponds to 5 or more reads). The diagonal elements of the heatmap correspond to 'self-loop' ligations, in which both ends of a single fragment ligate to each other (i.e., for example, frequent close neighbor intrachromosomal interactions). Squares near the diagonal correspond to ligation events between nearby fragments (i.e., for example, semifrequent short range intrachromosomal interactions). The relationship between proximity and genomic interaction frequency can be seen by the extreme intensity of close spatial proximity joins along the diagonal as compared to the more diffuse intensity of long range spatial proximity joins far off the diagonal. Although it is not necessary to understand the mechanism of an invention it is believed that these observations validate the Hi-C protocol in that three specific types of spatially diverse interactions can be readily observed that can be confirmed by chromosomal mapping.

Figure 13:
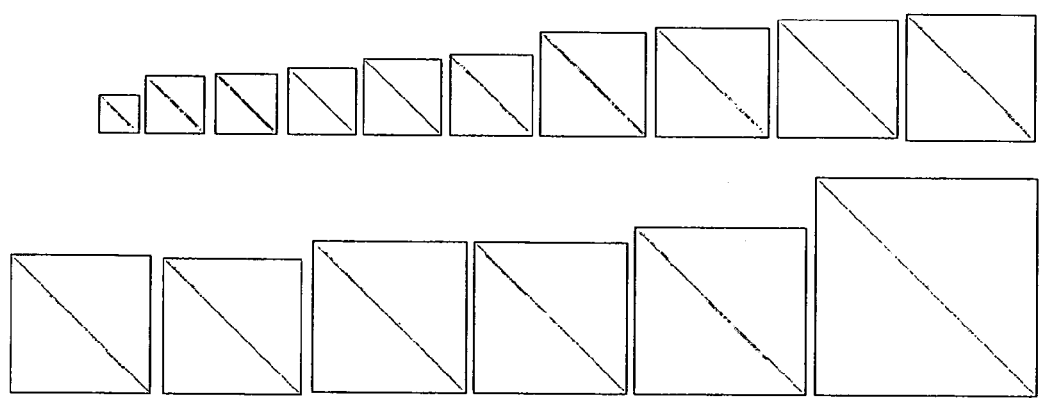
FIG. 13 presents exemplary Hi-C high throughput array heatmap data from all sixteen (16) yeast chromosomes, thereby providing a complete library of intrachromosomal interactions. Top Row: Heatmaps for Chromosomes 1-10: Bottom Row: Heatmaps for Chromosomes 11-16.

This technique was applied to all sixteen (16) yeast chromosomes at once (i.e., for example, the entire yeast genome) to create a database library of all the observed intrachromosomal interactions in the yeast genome. See, FIG. 13. Presently, the data show a clear display of close proximity interactions along the diagonal of each heatmap assay. Identification of short range and long range interactions for each chromosome is in progress. Alternatively, isolated product libraries for each chromosome may be processed through high-throughput sequencing and then sequence-matched to the source chromosome to identify their specific loci.

Figure 14:
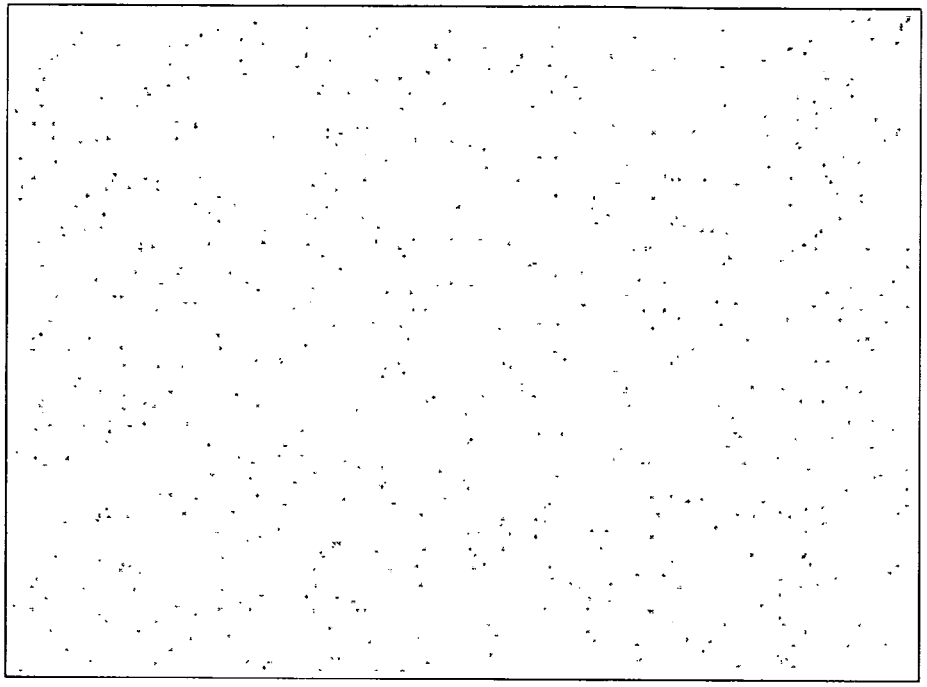
FIG. 14 presents exemplary 386×350 fragment Hi-C high throughput array heatmap data showing interchromosomal interactions between yeast chromosome fifteen (15) and yeast chromosome sixteen (16).

While the above discussion has reflected an analysis of intrachromosomal interactions, the Hi-C is not limited to that specific application. For example, Hi-C technology may also determine interchromosomal interactions. The data presented herein, demonstrate the creation of a preliminary Hi-C high throughput data array showing a number of putative genomic interactions between yeast chromosomes 15 and 16. Nonetheless, sequencing verification has not proceeded to the point where all the putative genomic interactions can be determined with accuracy. See, FIG. 14. Note that the interchromosomal 386×350 fragment array heatmap does not have a "close neighbor" diagonal that the above data reflects for intrachromosomal interaction studies. This observation is consistent with the fact that different chromosomes are inherently always at a disparate distance from one another. Therefore, frequent genomic interactions would not be expected. The data clearly indicate that the contents of the yeast Hi-C library reflect spatial co-location of loci in vivo, thereby fully validating the Hi-C technology.

Figure 15:
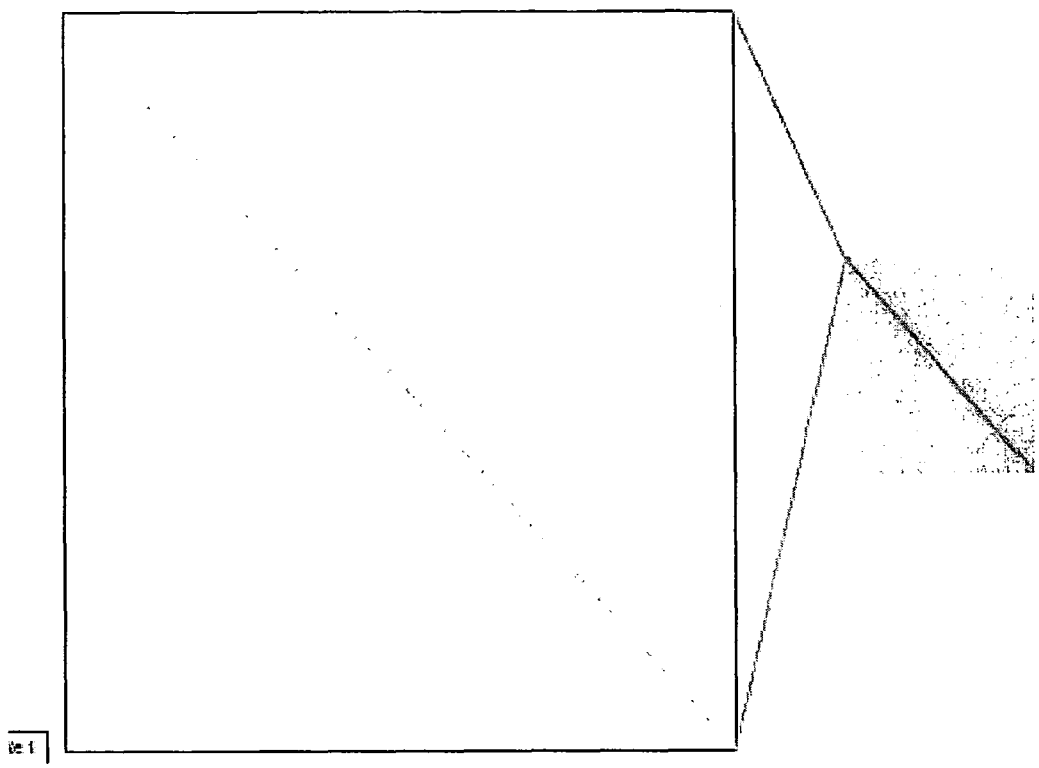
FIG. 15 presents exemplary Hi-C heatmap data showing the detailed distribution of close neighbor interactions (diagonal line intensities) and medium-long range genomic interactions (off diagonal intensities) of human chromosome 1.
Figure 16:
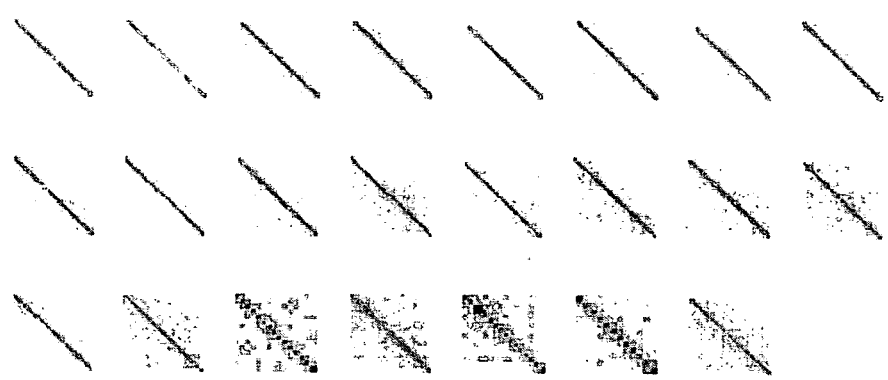
FIG. 16 presents exemplary Hi-C heatmap data showing the unique genomic interaction frequencies among a haploid set of human chromosomes. Top Row: Chromosomes 1-8. Middle Row: Chromosomes 9-16; Bottom Row: 17-23.

The human Hi-C results on chromosome 1 depict a strong close neighbor intrachromosomal interaction frequencies (i.e., diagonal line) in addition to a dense off-diagonal coloring reflective of a signification amount of long and medium range intrachromosomal interaction frequencies. See, FIG. 15. Similar intrachromosomal patterns can be seen for the complete haploid set of human chromosomes (i.e., for example, twenty-three chromosomes). The distinctive heatmap patterns and intensities suggest that a unique set of intra- and interchromosomal interaction frequencies are associated with the specific genes on each chromosome. See, FIG. 16.

IV. Gene Interaction Analysis

Color mapping of gene interaction data using contour color mapping approaches may be found in two, three, and four dimensional contour heatmaps. Contour color heatmapping uses the entire data space or data matrix (image) as the basis for the color process. Color intensity may thereby reflect that amount of data being processed for any particular data point.

Systems biology aims to understand biological systems on a comprehensive scale, such that the components that make up the whole are connected to one another and work through dependent interactions. Molecular correlations and comparative studies of molecular expression can establish interdependent connections in systems biology. Commercially available software packages provide limited data mining capability. These programs require the user to first generate visualization data with a preferred data mining algorithm and then upload the resulting data into the visualization package for graphic visualization of molecular relations. Alternative interactive visual data mining applications, (i.e., for example, SysNet) provide an interactive environment for the analysis of high data volume molecular expression information of most any type from biological systems. The interactive nature of the program presents intermolecular correlation information compatible with heatmap layouts. Zhang et al., "Interactive analysis of systems biology molecular expression data" *BMC Syst Biol.* 2:23 (2008).

Large quantities of chemical structure and biological activity data brought about through combinatorial chemistry and high-throughput screening technologies has created the need for sophisticated graphical tools to evaluate the data. Many chemoinformatics software applications apply standard clustering techniques to organize structure-activity data, but they differ significantly in their approaches to visualizing clustered data. For example, Molecular Property eXplorer (MPX) can presents clustered data in the form of heatmaps. MPX employs agglomerative hierarchical clustering to organize data on the basis of the similarity between 2D chemical structures or similarity across a predefined profile of biological assay values. Visualization of hierarchical clusters as heatmaps provides simultaneous representation of cluster members along with their associated assay values. Heatmaps provide visualization of the cluster members across an activity profile. Kibbey et al., "Molecular Property eXplorer: a novel approach to visualizing SAR using tree-maps and heatmaps" *J Chem Inf Model.* 45:523-32 (2005).

A genome-wide contact matrix (M) was constructed by dividing the genome into 1 Mb regions ('loci') and defining the matrix entry $m_{ij}$ to be the number of ligation products between locus i and locus j (SOM). This matrix reflects an ensemble average of the interactions present in the original sample of cells; it can be visually represented as a heatmap, with intensity indicating contact frequency. See, FIG. 17B.

Hi-C results were seen to be reproducible by repeating the experiment using either the same restriction enzyme (HindIII) and using a different restriction enzyme (NcoI). See, FIG. 17C and FIG. 17D, respectively. Both contact matrices were extremely similar to the original contact matrix (Pearson's r=0.990 [HindIII] and r=0.814 [NcoI]; p was negligible [<10-300] in both cases).

Figure 18:
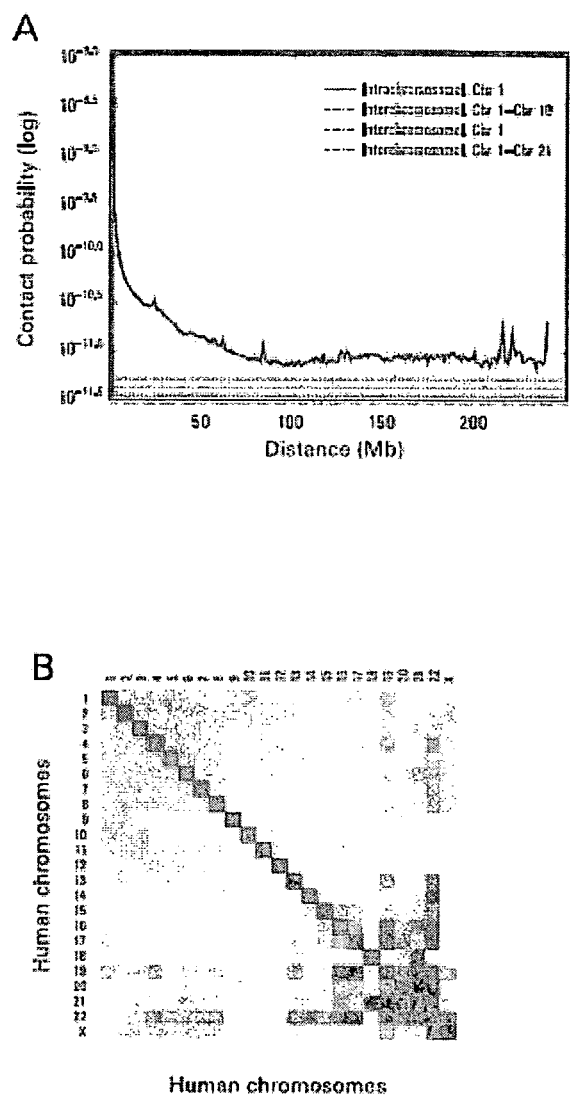
FIG. 18 presents exemplary data showing the presence and organization of chromosome territories.

Data was consistent with known features of genome organization—for example, chromosome territories (the tendency of distant loci on the same chromosome to be near one another in space) and patterns in sub-nuclear positioning (the tendency of certain chromosome pairs to be near one another). An average intrachromosomal contact probability (In(s)) was calculated for pairs of loci separated by a genomic distance s (distance in base pairs along the nucleotide sequence) on chromosome n. In(s) were observed to decrease monotonically on every chromosome, suggesting polymer-like behavior in which the three-dimensional distance between loci increases with increasing genomic distance. These findings are in agreement with 3C and fluorescence in situ hybridization (FISH). Dekker et al., *Science* 295:1306 (2002); and Yokota et al., *J Cell Biol* 130:1239 (1995). The data suggest that at distances greater than 200 Mb, In(s) is always much greater than the average contact probability between different chromosomes. See, FIG. 18A. Although it is not necessary to understand the mechanism of an invention, it is believed that this In(s) differential implies the existence of chromosome territories.

The above data show interchromosomal contact probabilities between pairs of chromosomes suggesting that small, gene-rich chromosomes (i.e., for example, chromosomes 16, 17, 19, 20, 21, 22) preferentially interact with each other. See, FIG. 18B. This is consistent with FISH studies showing that these chromosomes frequently co-localize in the center of the nucleus. Boyle et al., *Hum Mol Genet* 10:211 (2001); and Tanabe et al., *Mutat Res* 504:37 (2002). Interestingly, chromosome 18, which is small but gene-poor, does not interact frequently with the other small chromosomes. Again, this observation agrees with FISH studies showing that chromosome 18 tends to be located near the nuclear periphery. Croft et al., *J Cell Biol* 145:1119 (1999).

Figure 19:
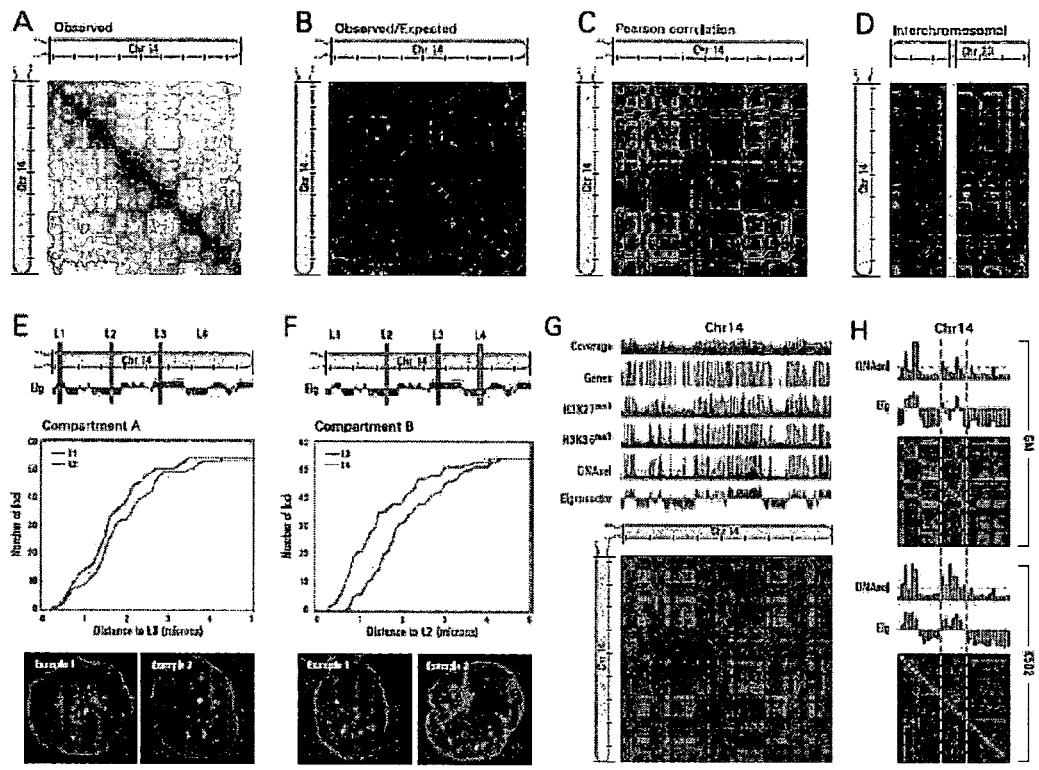
FIG. 19 presents exemplary data wherein a nucleus is segregated into two compartments corresponding to open and closed chromatin.

An individual chromosome analysis can identify whether chromosomal regions may preferentially associate with each other. Although it is not necessary to understand the mechanism of an invention, it is believed that because sequence proximity strongly influences contact probability, a normalized contact matrix (M*) was defined by dividing each entry in the contact matrix by the genome-wide average contact probability for loci at that genomic distance (SOM). For example, a normalized matrix was generated showing many large blocks of enriched and depleted interactions generating a 'plaid' pattern. See, FIG. 19B.

If two loci (i.e., for example, 1 Mb regions) are nearby in space, they might share neighbors and have correlated interaction profiles. In the study of this interaction, a correlation matrix (C) was defined in which $c_{ij}$ is the Pearson correlation between the $i^{th}$ row and $j^{th}$ column of M*. The data demonstrated that this process dramatically sharpened the plaid pattern wherein approximately 71% of the resulting matrix entries represent statistically significant correlations ($p \le 0.05$). See, FIG. 19C.

Figure 20:
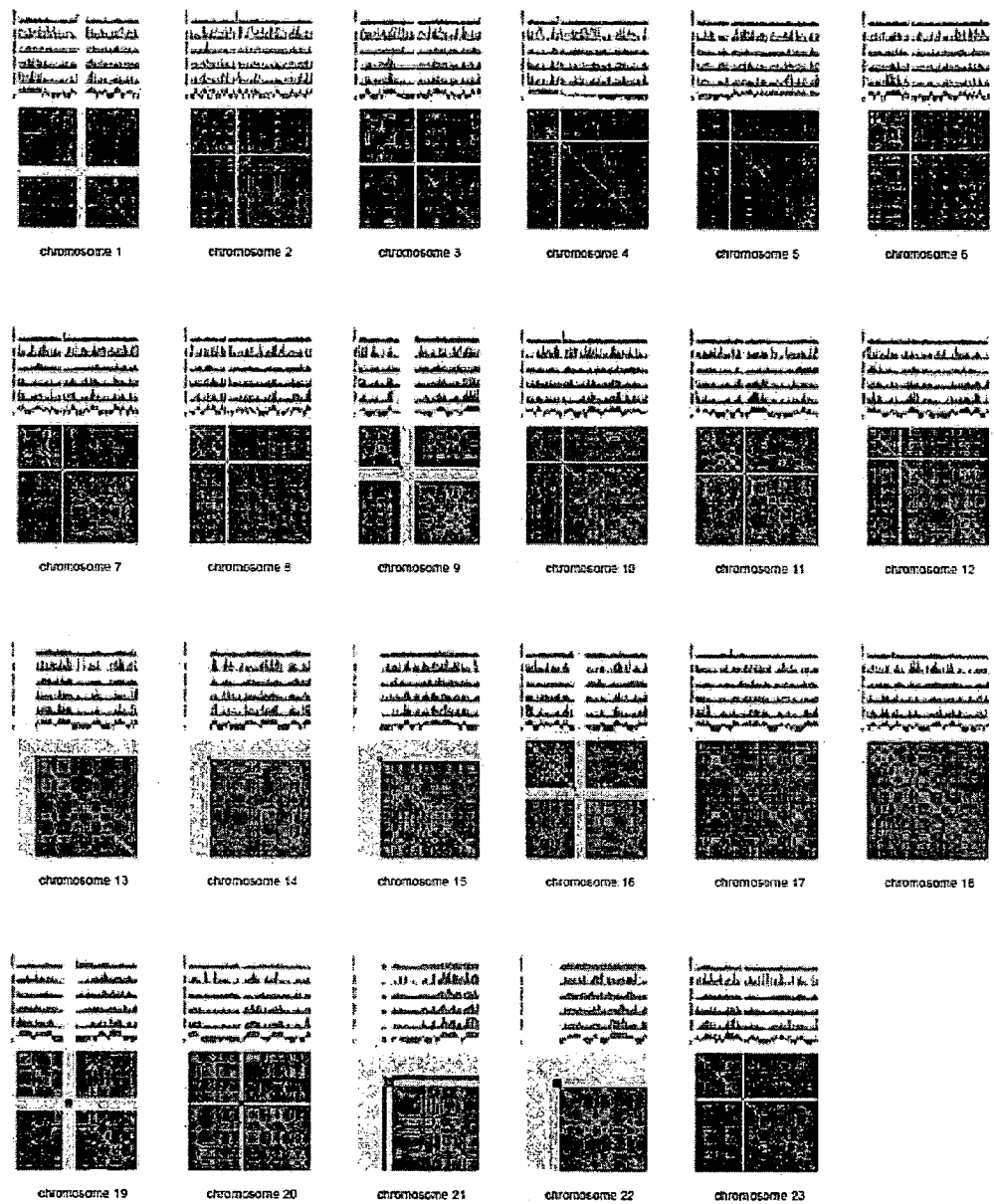
FIG. 20 presents exemplary data showing a partitioning of chromatin into two spatial compartments is seen for all 23 chromosomes in GM06990. Correlation maps at a resolution of 1 Mb are shown for every chromosome (grey: unalignable, blue: centromeres). There is a strong correlation between the principal component (eigenvector), which reflects the compartmentalization inherent in the heatmaps, and the distribution of fixed features such as genes. The eigenvector also correlates with dynamic features such as open chromatin (DNAseI sensitivity), activating histone modifications (H3K36me3), repressive histone modifications (H3K27me3). At higher resolutions, the correlation to repressive marks is dramatically reduced.

Although it is not necessary to understand the mechanism of an invention, it is believed that a plaid pattern suggests that each chromosome can be decomposed into two sets of loci (arbitrarily labeled A and B) such that contacts within each set are enriched and contacts between sets are depleted. Each chromosome may be partitioned in this way using principal component analysis. For all but two chromosomes, the first principal component (PC) clearly corresponded to the plaid pattern (positive values defining one set, negative values the other). See, FIG. 20. For example, the data for chromosomes 4 and 5 show that the first PC corresponded to the two chromosome arms, but the second PC corresponded to the plaid pattern. The entries of the PC vector reflected the sharp transitions from compartment to compartment observed within the plaid heatmaps. Moreover, the plaid patterns within each chromosome were consistent across chromosomes: the labels (A and B) could be assigned on each chromosome so that sets on different chromosomes carrying the same label had correlated contact profiles, and those carrying different labels had anticorrelated contact profiles. See, FIG. 19D. These results imply that the entire genome can be partitioned into two spatial compartments such that greater interaction occurs within each compartment rather than across compartments.

These data imply that regions tend be closer in space if they belong to the same compartment (i.e., for example, A vs. B) than if they do not. A 3D-FISH technique confirmed this hypothesis by probing four loci (i.e., for example, L1, L2, L3, and L4) on chromosome 14 that alternate between the two compartments (L1 and L3 in compartment A; L2 and L4 in compartment B). See, FIG. 19E and FIG. 19F, respectively. The 3D-FISH data showed that L3 tends to be closer to L1 than to L2, despite the fact that L2 lies between L1 and L3 in the linear genome sequence. Similarly, L2 was closer to L4 than to L3.

Figure 21:
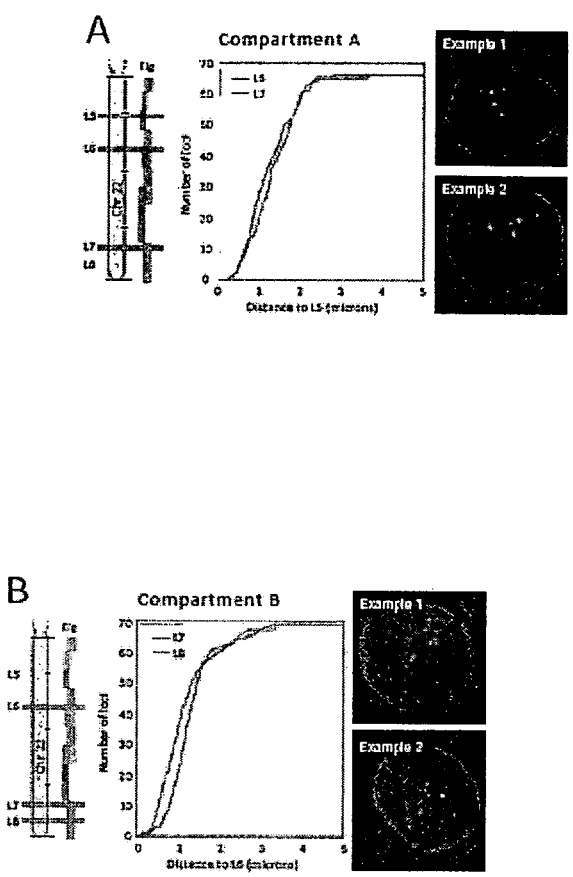
FIG. 21 presents exemplary data showing a confirmation of genome compartmentalization by 3D-FISH. To confirm the compartmentalization of the genome, FISH probes for four loci (L5, L6, L7, and L8) were selected that lie consecutively along Chromosome 22 but alternate between the two compartments (i.e., for example, L5, L7 in A; L6, L8 in B).
Figure 22:
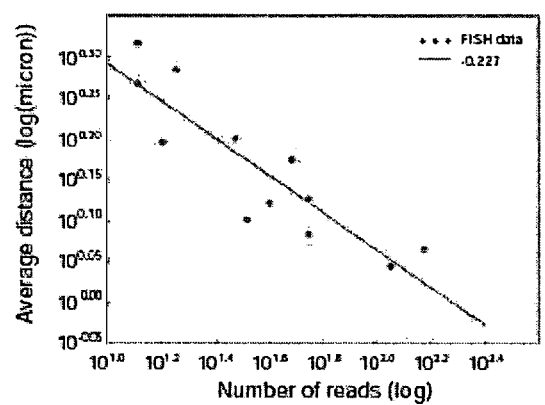
FIG. 22 presents exemplary data showing that a Hi-C interaction frequency correlates with 3D distance. Average inter-locus distance as determined by 3D FISH is compared to the number of reads with one end in each of the tested loci (blue dots). A strong correlation is observed (red).

Comparable results were obtained for four consecutive loci on chromosome 22. See, FIG. 21A and FIG. 21B. Taken together, these observations confirm the spatial compartmentalization of the genome inferred from a Hi-C experiment (supra). More generally, a strong correlation was observed between the number of Hi-C reads $m_{ij}$ and the three-dimensional distance between locus i and locus j as measured by FISH (Spearman's rho=0.874, p=0.0002, suggesting that Hi-C read count may serve as a proxy for distance. See, FIG. 22.

Figure 23:
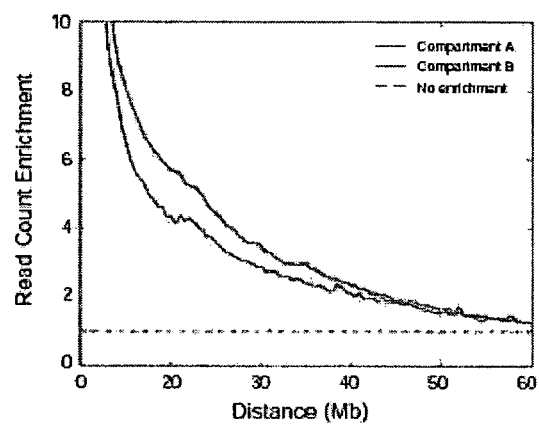
FIG. 23 presents exemplary data showing that compartment A is less compact then compartment B and/or compartment B is more compact than compartment A. Read enrichment as a function of distance for interactions between loci in noncontiguous blocks belonging to the same compartment (A: blue; B: green). Compartment B is consistently more enriched at every inter-locus distance. Read enrichment is computed as number of reads divided by expected number of reads assuming random ligation.

The data further demonstrate that pairs of loci in compartment B showed a consistently higher interaction frequency at a given genomic distance than pairs of loci in compartment A. See, FIG. 23. These data suggest that compartment B may be more densely packed. Dekker, J., *J Biol Chem* 283:34532 (2008). The FISH data are consistent with this observation; wherein loci in compartment B exhibited a stronger tendency for close spatial localization.

Figure 24:
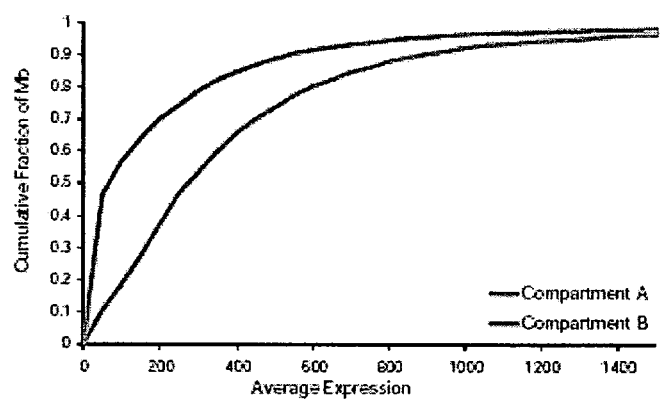
FIG. 24 presents exemplary data demonstrating a cumulative distribution showing expression in compartment A (red) and compartment B (blue). The results demonstrate that genes in compartment B have markedly lower expression as compared to genes in compartment A.

Compartments A and B were evaluated using 1 Mb correlation maps as to whether they correspond to known genetic and epigenetic features of the genome. Compartment A correlates strongly with the presence of: i) genes (Spearman's rho=0.431, $p<10^{-137}$); ii) higher expression (i.e., for example, via genome-wide mRNA expression, Spearman's rho=0.476, $p<10^{-145}$; and iii) accessible chromatin (i.e., for example, by measuring DNAseI sensitivity, Spearman's rho=0.651, p negligible). See, FIG. 24. Sabo et al., *Nat Methods* 3:511 (2006); and Hesselberth et al., *Nat Methods* 6:283 (2009). Compartment A also shows enrichment for both activating chromatin marks (i.e., for example, H3K36 trimethylation, Spearman's rho=0.601, $p<10^{-296}$) and repressive chromatin marks (i.e., for example, H3K27 trimethylation, Spearman's rho=0.282, $p<10^{-56}$). Mikkelsen et al., *Nature* 448:553 (2007). The above analysis was repeated at a resolution of 100 kb. Correlation of compartment A with all other genomic and epigenetic features remained strong (Spearman's rho>0.4, p negligible), but the correlation with a repressive chromatin mark (i.e., for example, H3K27 trimethylation) was dramatically attenuated (Spearman's rho=0.046, $p<10^{-15}$). See, FIG. 19G. These results suggest that compartment A is more closely associated with open, accessible, actively transcribed chromatin.

Figure 25:
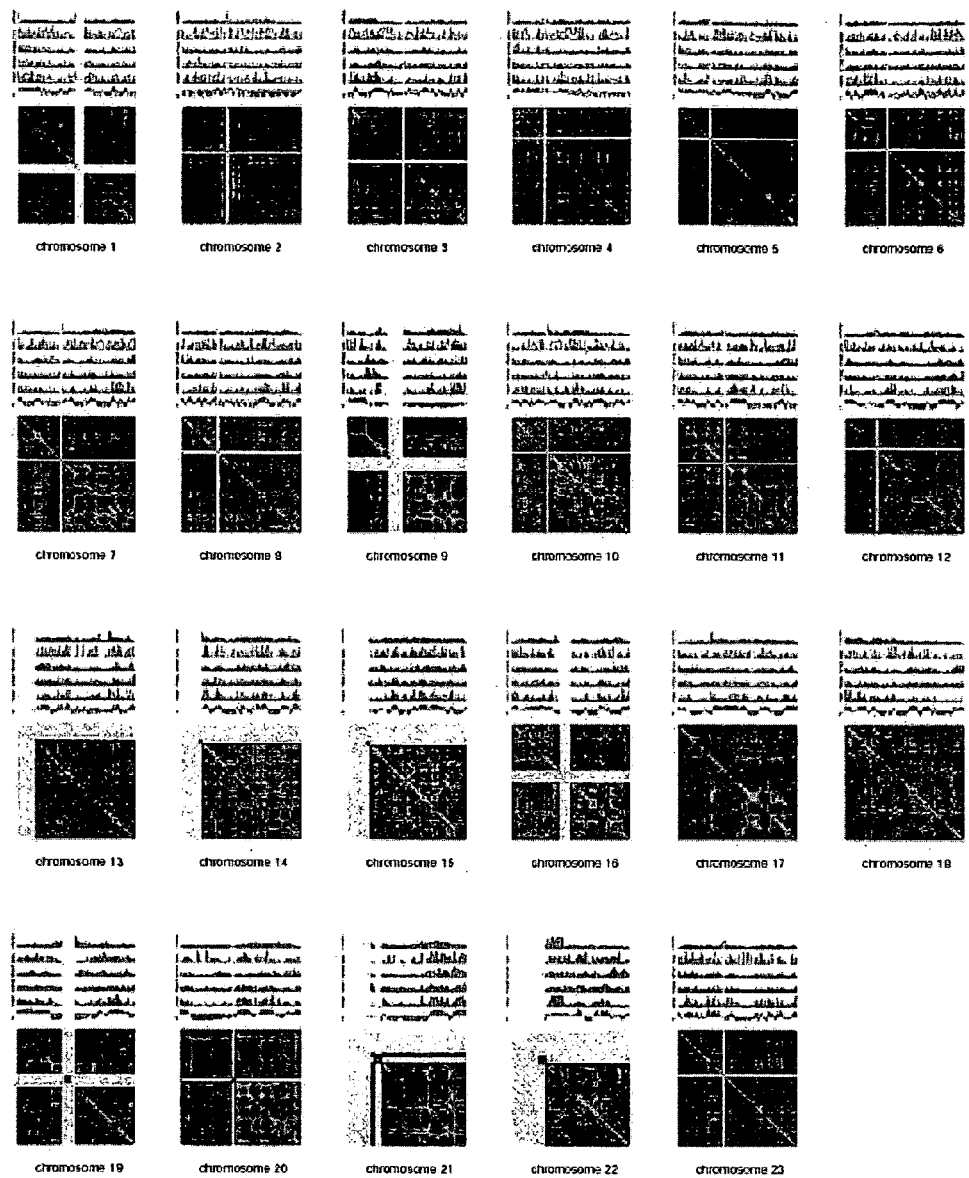
FIG. 25 presents exemplary data showing a partitioning of chromatin into two spatial compartments is seen for all 23 chromosomes in K562. Correlation maps at a resolution of 1 Mb are shown for every chromosome (grey: unalignable, blue: centromeres). There is a strong correlation between the principal component (eigenvector), which reflects the compartmentalization inherent in the heatmaps, and the distribution of fixed features such as genes. The eigenvector also correlates with dynamic features such as open chromatin (DNAseI sensitivity), activating histone modifications (H3K36me3), repressive histone modifications (H3K27me3). At higher resolutions, the correlation to repressive marks is dramatically reduced.

The above experimental design was also used to study K562 cells, an erythroleukemia cell line with an aberrant karyotype. Naumann et al., *Leuk Res* 25:313 (2001). Two compartments were again observed having a similar composition to those observed in GM06990 cells (Pearson's r=0.732, p negligible) and showed strong correlation with open and closed chromatin states as indicated by DNAseI sensitivity (Spearman's rho=0.455, $p<10^{-154}$). See, FIG. 25. The compartment patterns in K562 and GM are similar, but there are many loci in the open compartment in one cell type and the closed compartment in the other. See, FIG. 19H. These discordant loci were examined on karyotypically normal chromosomes in K562. A strong correlation was observed between the compartment pattern in a cell type and chromatin accessibility in that same cell type (GM06990, Spearman's rho=0.384, p=0.012; K562, Spearman's rho=0.366, p=0.017). Thus, even in a highly rearranged genome, spatial compartmentalization correlates strongly with chromatin state.

Although it is not necessary to understand the mechanism of an invention, it is believed that these results demonstrate that open and closed chromatin domains throughout the genome occupy different spatial compartments in the nucleus. It is further believed that these findings may expand upon studies of individual loci that have observed particular instances of such interactions; both between distantly located active genes, and between distantly located inactive genes. Osborne et al., *Nat Genet* 36:1065 (2004); Brown et al., *J Cell Biol* 182:1083 (2008); Dernburg et al., *Cell* 85:745 (1996); Shopland et al., *J Cell Biol* 174:27 (2006); and Fraser et al., *Nature* 447:413 (2007).

Figure 52:
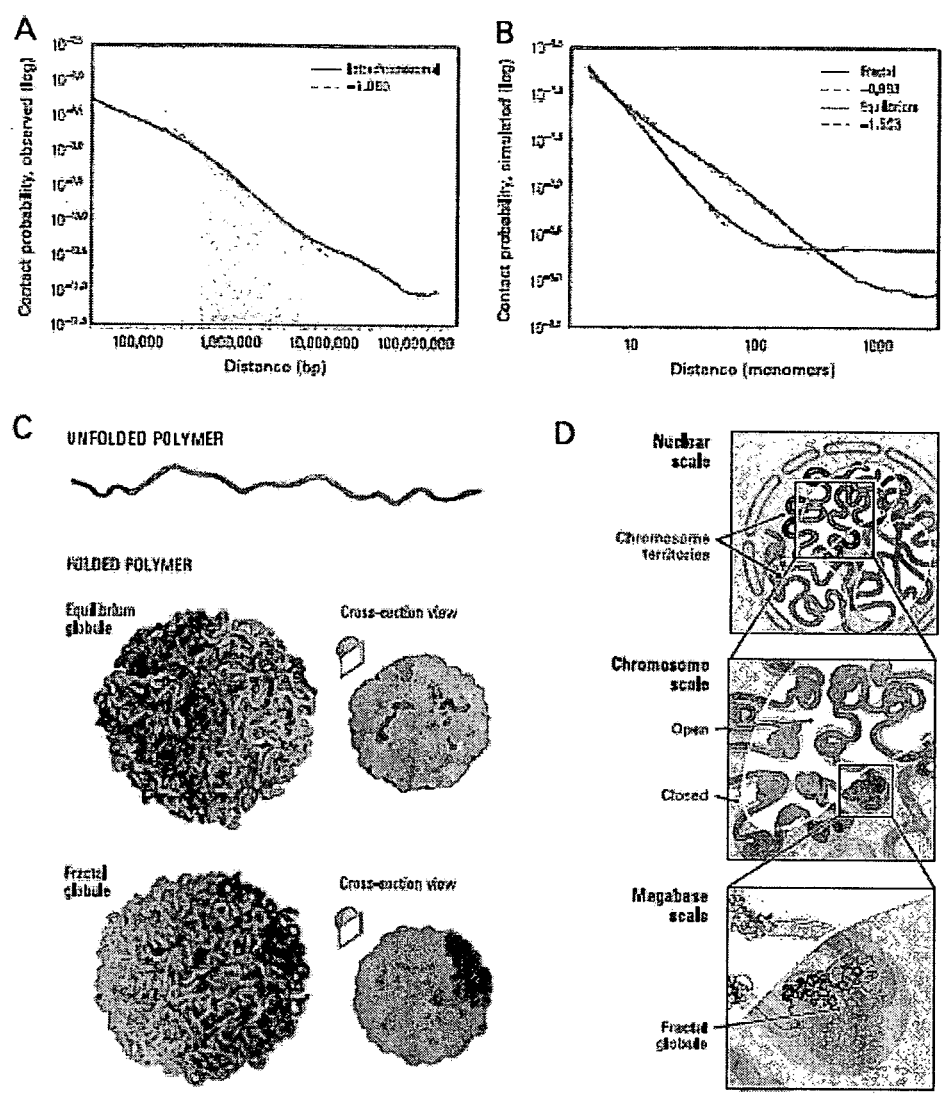
FIG. 52 presents exemplary data showing that local packing of chromatin may be consistent with the behavior of a fractal globule.

The data further show an analysis of the internal structure of the open and closed chromatin domains that correspond to the compartments seen in the plaid correlation maps. For example, the average behavior of intrachromosomal contact probability was examined as a function of genomic distance by calculating the genome-wide distribution (I(s)). When plotted on log-log axes, I(s) exhibits a prominent power law scaling between ~500 kb and ~7 Mb, where contact probability scales as $s^{-1}$. See, FIG. 52A. This range corresponds to the known size of open and closed chromatin domains.

It has been reported that power-law dependencies can arise from polymer-like behavior. P. G. d. Genres, In: Scaling concepts in polymer physics (Cornell University Press, Ithaca, N.Y., 1979), pp. 324 p. Various reports have proposed that chromosomal regions can be modeled as an 'equilibrium globule'—a compact, densely knotted configuration originally used to describe a polymer in a poor solvent at equilibrium. Münkel et al., *Physical Review E*57:5888 (1998); and Mateos-Langerak et al., *Proc Natl Acad Sci USA* 106:3812 (2009). Historically, this specific model has often been referred to simply as a 'globule' or 'equilibrium globule' to distinguish it from other globular states.

One alternative model was proposed theorizing that polymers, including interphase DNA, can self-organize into a long-lived, non-equilibrium conformation that they described as a 'fractal globule'. Grosberg et al., *J. Phys. France* 49:2095 (1988); and Grosberg et al., *Europhysics Letters,* 373 (1993). Although it is not necessary to understand the mechanism of an invention, it is believed that this highly compact state is formed by an unentangled polymer when it crumples into a series of small globules in a 'beads-on-a-string' configuration. These beads may serve as monomers in subsequent rounds of spontaneous crumpling until only a single globule-of-globules-of-globules remains. It is believed that the resulting structure resembles a Peano curve, a continuous fractal trajectory that densely fills three-dimensional space without crossing itself. Mandelbrot B. D., In: The fractal geometry of nature (W.H. Freeman, New York, ed., 1983), pp. 468. Fractal globules have been proposed as an attractive structure for chromatin segments because they lack knots thereby facilitating unfolding and refolding, e.g. during gene activation, gene repression, or the cell cycle. Vasilyev et al., *Theoretical and Mathematical Physics* 134:142 (2003). For example, in a fractal globule, contiguous regions of the genome tend to form spatial sectors whose size corresponds to the length of the original region. In contrast, an equilibrium globule is highly knotted and lacks such sectors; instead, linear and spatial positions are largely decorrelated after at most a few megabases. See, FIG. 52C. The fractal globule has not previously been observed. Grosberg et al., *Europhysics Letters,* 373 (1993).

The 'equilibrium globule' and 'fractal globule' models make very different predictions concerning the scaling of contact probability with genomic distance s. The equilibrium globule model predicts that contact probability will scale as $s^{-3/2}$, which is not observed in the data presented herein. Analytical derivation of contact probabilities for the presently disclosed data in relation to a fractal globule found a decay as $s^{-1}$ (SOM) that corresponds closely with the observed prominent scaling (−1.08).

Equilibrium and fractal globule models also make differing predictions about the three-dimensional distance between pairs of loci (i.e., for example, $s^{1/2}$ for an equilibrium globule and $s^{1/3}$ for a fractal globule). These data are consistent with 3D-FISH techniques finding an $s^{1/3}$ scaling for genomic distances between 500 kb and 2 Mb. Mateos-Langerak et al., *Proc Natl Acad Sci USA* 106:3812 (2009).

Monte Carlo simulations were used to construct ensembles of fractal globules and equilibrium globules (i.e., for example, 500 each). The properties of the ensembles matched the theoretically-derived scalings for contact probability (i.e., for example, fractal: $s^{-1}$, equilibrium: $s^{-3/2}$) and three dimensional distance (i.e., for example, fractal: $s^{1/3}$, equilibrium: $s^{1/2}$). These simulations also illustrated the lack of entanglements as measured by the knot-theoretic Alexander polynomial. Kolesov et al., *Nucleic Acids Res* 35:W425 (2007). The simulations also found the formation of spatial sectors within a fractal globule. See, FIG. 52B.

Although it is not necessary to understand the mechanism of an invention, it is believed that the data presented herein, when evaluated at the scale of several megabases, are consistent with a fractal globule model for chromatin organization and find chromatin interactions at relatively large scales. The techniques disclosed herein can also be used to construct comprehensive, genome-wide interaction maps at finer scales by increasing the number of reads. In some embodiments, the present invention contemplates mapping of specific long-range interactions between enhancers, silencers, and insulators. Blackwood et al., *Science* 281:60 (1998); Bell et al., *Science* 291:447 (2001); and Phillips et al., *Cell* 137:1194 (2009). In one embodiment, the method increasing the resolution by a factor of n, by increasing the number of reads by a factor of $n^2$.

V. Purification Processes

In one embodiment, the present invention contemplates purifying junction markers comprising affinity chromatography. In one embodiment, the junction marker may be concentrated using a commercially available protein concentration filter, for example, an Amicon or Millipore Pellicon ultrafiltration unit. Following the concentration step, the concentrate can be applied to a suitable purification matrix, wherein the matrix is capable of selectively binding to the marker. For example, a suitable affinity matrix can comprise a strepavidin, a histidine ligand, a FLAG ligand, and/or an antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in purification. Alternatively, a cation exchange step can be employed. Suitable cation exchangers include various insoluble matrices comprising sulfopropyl or carboxymethyl groups. Sulfopropyl groups are preferred.

In one embodiment, the present invention contemplates a purification method comprising a reversed-phase high performance liquid chromatography (RP-HPLC) technique comprising hydrophobic RP-HPLC media, e.g., silica gel having pendant methyl or other aliphatic groups, can be employed to further purify junction markers.

In one embodiment, the present invention contemplates a purification method comprising gel electrophoresis. Many types of electrophoresis gels are commerically available that are suitable for the nucleic acids contemplated herein.

VI. Therapeutic Agents For Disease-Correlated Genomic Activities

In one embodiment, the present invention contemplates identifying regulatory genes or regulatory elements capable of modulating open reading frame sequences through physical interactions (close spatial proximity) between these regulatory elements and these open reading frames. The regulatory elements and open reading frame can be located near or far apart along the linear genome sequence or can be located on different chromosomes. In one embodiment, the open reading frame sequences are associated with a medical condition. In one embodiment, the medical condition comprises cancer. In one embodiment, the medical condition comprises a cardiovascular disease. In one embodiment, the medical condition comprises a kidney disease. In one embodiment, the medical condition comprises an autoimmune disease. In one embodiment, the medical condition comprises a pulmonary disease. In one embodiment, the medical condition comprises a liver disease. In one embodiment, the medical condition comprises a lymphoid disease. In one embodiment, the medical condition comprises a bone marrow disease. In one embodiment, the medical condition comprises a bone disease. In one embodiment, the medical condition comprises a blood disorder. In one embodiment the gene and regulatory elements are identified in a genome-wide association approach to be linked to a human condition or disease.

A genome-wide association approach in identifying genetic variants associated with complex human diseases has been a powerful and efficient study design. This approach became feasible as the result of several key advancements in genetic knowledge, genotyping technologies, statistical analysis algorithms and the availability of large collections of cases and controls. With all these necessary tools in hand, many genome-wide association studies were recently completed. Reports of genome-wide associations for several complex diseases including, but not limited to, inflammatory bowel disease, type-2 diabetes, breast cancer and prostate cancer have been released. Seng et al., "The success of the genome-wide association approach: a brief story of a long struggle" *Eur J Hum Genet.* 16:554-564 (2008).

A. Genetic Influences on Cancer

Patients with a genetic predisposition to colorectal cancer have significantly increased risks for developing this malignancy over their lifetime. These risks can approach an 80 to nearly 100% likelihood of colorectal malignancy with some of the known cancer predisposition syndromes. Burt et al. *Gastroenterolog;* 128:1696-1716 (2005). Specific gastrointestinal conditions having an underlying genetic basis include, but are not limited to, colorectal cancer, familial adenomatous polyposis, Lynch syndrome, attenuated familial adenomatous polyposis, MYH-associated polyposis, hereditary mixed polyposis, and hyperplastic polyposis. Gammon et al., "Can we identify the high-risk patients to be screened? A genetic approach" *Digestion* 76:7-19 (2007).

The genetic basis of acute myeloid leukemia (AML) has been described. Identifying leukemia-associated aberrant phenotypes, and real-time quantitative polymerase chain reaction (RQ-PCR) detecting leukemia-specific targets (e.g., fusion gene transcripts, NPM1 mutation) or genes overexpressed in AML (e.g., WT1), can provide a more precise measure of disease response. Freeman et al., "Development of minimal residual disease-directed therapy in acute myeloid leukemia" *Semin Oncol.* 35:388-400 (2008).

The Philadelphia chromosome-negative myeloproliferative disorders (MPDs) polycythemia vera (PV), essential thrombocytosis (ET) and primary myelofibrosis (PMF) are believed characterized by increased proliferation of terminally differentiated myeloid cells. The genetic basis for these disorders was identified in 2005 when a single recurrent mutation in the JAK2 tyrosine kinase (JAK2V617F) was identified in >90% of patients with PV and in a significant proportion of patients with ET and PMF. Subsequent studies of JAK2V617F-negative MPDs have identified mutations in JAK2 exon 12 and MPL, and these mutations also result in constitutive activation of JAK2 signaling. Koppikar et al., "JAK2 and MPL mutations in myeloproliferative neoplasms" *Acta Haematol.* 119:218-225 (2008).

Familial adenomatous polyposis is an archetypal disease illustrating the genetic basis of human cancer. The adenomatous polyposis coli gene functions as a tumor suppressor with hundreds of known mutations that result in a defective adenomatous polyposis coli protein. In addition to the certain fate of colon cancer without colectomy, patients with familial adenomatous polyposis are also at increased risk for other types of neoplasms, including those which affect the pancreas. This review focuses on periampullary and ampullary tumors, benign and malignant pancreatic neoplasms that are associated with familial adenomatous polyposis and Gardner syndrome and pancreatitis in these patients. Elkharwily et al., "The pancreas in familial adenomatous polyposis" *J Pancreas* 9:9-18 (2008).

Gastroenteropancreatic neuroendocrine tumors (GEP-NETs) are usually sporadic; however, familial (inherited) syndromes, such as the multiple endocrine neoplasia 1 (MEN-1) syndrome, von Hippel-Lindau (VHL) syndrome, neurofibromatosis (NF-1), as well as tuberous sclerosis, may be associated with proximal intestinal and pancreatic NETs. For example, 25% of gastrinoma patients have MEN-1 syndrome. The genetic basis of tumorigenesis for these familial syndromes has been clearly identified, providing clinicians with useful screening tools for affected families. Also, over the last few years, advanced molecular genetic techniques, such as comparative genomic hybridization (CGH) and loss of heterozygosity (LOH) analyses, have detected some differences in genomic aberrations among various types of NETs. Toumpanakis et al., "Molecular genetics of gastroenteropancreatic neuroendocrine tumors" *Am J Gastroenterol.* 103:729-732 (2008).

B. Genetic Influences on Cardiovascular Disease

Cardiovascular disease is the leading cause of death worldwide and premature arterial stiffening is a contributor to this risk. An overview of the current literature provides evidence that links genetic factors to arterial wall properties. There are a number of candidate genes and many of these could potentially affect the structure and function of the arterial wall. Indeed, it is likely that genes involving signaling pathways and control of the vessel wall matrix may be involved. Identifying the genes involved may suggest new biomarkers as well as provide drug targets. Yasmin et al., "Genetics of arterial structure and function: towards new biomarkers for aortic stiffness?" *Clin Sci (Lond)* 114:661-677 (2008).

Congenital heart disease is the leading cause of infant morbidity in the Western world, but only in the past ten years has its etiology been understood. Recent studies have uncovered the genetic basis for some common forms of the disease and provide new insight into how the heart develops and how dysregulation of heart development leads to disease. Bruneau B G., "The developmental genetics of congenital heart disease" *Nature* 451:943-948 (2008).

Inherited, or autosomal dominant, hypercholesterolemia, with an average global prevalence of one in 500 individuals, is one of the most frequent inherited metabolic disorders. The disorder is associated with a high risk for premature cardiovascular disease (CVD) and death as a consequence of accelerated atherosclerosis. Although the molecular genetic basis is largely elucidated and effective medical treatment, in the form of inhibitors of intracellular cholesterol synthesis, is available, the disorder is severely under diagnosed and under treated. On the other hand, with the well-understood etiology, the accurate diagnosis, the availability of sensitive predictive makers and efficacious therapy, this disorder can serve as a model for disease management: from early presymptomatic diagnosis, accurate prognosis, optimal treatment and large-scale screening to population-based prevention of CVD. Fouchier et al., "Management of hereditary dyslipidaemia; the paradigm of autosomal dominant hypercholesterolaemia" *Eur J Hum Genet.* 13:1247-1253 (2005).

Cardiomyopathies are primary disorders of cardiac muscle associated with abnormalities of cardiac wall thickness, chamber size, contraction, relaxation, conduction, and rhythm. They are a major cause of morbidity and mortality at all ages and, like acquired forms of cardiovascular disease, often result in heart failure. Over the past two decades, molecular genetic studies of humans and analyses of model organisms have made remarkable progress in defining the pathogenesis of cardiomyopathies. Hypertrophic cardiomyopathy can result from mutations in 11 genes that encode sarcomere proteins, and dilated cardiomyopathy is caused by mutations at 25 chromosome loci where genes encoding contractile, cytoskeletal, and calcium regulatory proteins have been identified. Causes of cardiomyopathies associated with clinically important cardiac arrhythmias have also been discovered: Mutations in cardiac metabolic genes cause hypertrophy in association with ventricular pre-excitation and mutations causing arrhythmogenic right ventricular dysplasia were recently discovered in protein constituents of desmosomes. This considerable genetic heterogeneity suggests that there are multiple pathways that lead to changes in heart structure and function. Defects in myocyte force generation, force transmission, and calcium homeostasis have emerged as particularly critical signals driving these pathologies. Delineation of the cell and molecular events triggered by cardiomyopathy gene mutations provide new fundamental knowledge about myocyte biology and organ physiology that accounts for cardiac remodeling and defines mechanistic pathways that lead to heart failure. Ahmad et al., "The genetic basis for cardiac remodeling" *Annu Rev Genomics Hum Genet.* 6:185-216 (2005)

C. Genetic Influences on Kidney Disease

The discovery of the functional link between TSC2 and the polycystic kidney disease 1 gene (PKD1) is beginning to build a foundation for understanding the heritable diseases associated with defects in each of these genes, namely, tuberous sclerosis complex and polycystic kidney disease. The functions of the TSC2 gene product, tuberin, has implications in the development of cystic kidney disease. Cai et al., "TSC2, a key player in tumor suppression and cystic kidney disease" *Nephrol Ther.* 2 Suppl 2:S119-S122 (2006).

Non-B DNA conformations adopted by certain types of DNA sequences promote genetic instabilities, especially gross rearrangements including translocations. It is believed that: (a) slipped (hairpin) structures, cruciforms, triplexes, tetraplexes and i-motifs, and left-handed Z-DNA are formed in chromosomes and elicit profound genetic consequences via recombination-repair, (b) repeating sequences, probably in their non-B conformations, cause gross genomic rearrangements (translocations, deletions, insertions, inversions, and duplications), and (c) these rearrangements may provide a genetic basis for numerous human diseases including, but not limited to, polycystic kidney disease. Bacolla et al., "The involvement of non-B DNA structures in gross chromosomal rearrangements" *DNA Repair (Amst).* 5:1161-1170 (2006)

Chronic Kidney Disease (CKD) susceptibility has a genetic basis. Recent studies of familial focal segmental glomerulosclerosis and the discoveries identified genetic and genomic approaches used to understand its pathogenesis. For example, slit diaphragm proteins were discovered using linkage analyses thereby causing glomerulosclerosis. Podocyte dysfunction is now recognized as a contributor to the functional and histologic derangements that characterize glomerular dysfunction in many common causes of CKD. In aggregate, these studies provide a paradigm for approaches to better define mechanisms of CKD and to identify novel therapeutic targets. Padiyar et al., "Genetic and genomic approaches to glomerulosclerosis" *Curr Mol Med.* 5:497-507 (2005).

D. Genetic Influences on Autoimmune Disease

Some people inherit an unfortunate combination of genetic sequences, such that exposure to an external trigger causes their immune response to turn on their own tissues. Although mutations in a single gene can cause autoimmunity, most autoimmune diseases are associated with several sequence variants. Marked advances in genetic resources and tools are now making it possible to identify the sequence variants that contribute to autoimmune diseases—promising a better understanding of how we normally remain tolerant of our own tissue components, and how this goes wrong in autoimmune disease. Rioux et al., "Paths to understanding the genetic basis of autoimmune disease" *Nature* June 2; 435:584-589 (2005).

Systemic lupus erythematosus (SLE) is a systemic autoimmune disease of unknown etiology with a complex genetic basis that includes many susceptibility genes on multiple chromosomes. As complex human diseases like SLE involve multiple, interacting genetic and environmental determinants, identifying genes for complex traits is challenging and has had limited success so far. Prioritization of candidate genes based on map position and biologic relevance is currently lacking. Obtaining the genomic structure of these genes as well as to study sequence variants will facilitate the identification of genes that are important in the development and expression (severity) of lupus and associated phenotypes. Castro et al., "The complex immunogenetic basis of systemic lupus erythematosus" *Autoimmun Rev.* 7:345-351 (2008).

Myocarditis is a clinically heterogeneous myocardial inflammatory disease, diagnosed by endomyocardial biopsy and may have an autoimmune basis. Myocarditis and dilated cardiomyopathy represent different stages of an organ-specific autoimmune disease in genetically predisposed individuals. Susceptibility may be based on multiple major histocompatibility complex and nonmajor histocompatibility complex genes. In patients the diagnosis of autoimmune myocarditis/dilated cardiomyopathy requires exclusion of viral genome on endomyocardial biopsy and detection of serum heart-reactive autoantibodies. They are directed against multiple antigens that are found in patients and relatives from about 60% of familial and nonfamilial pedigrees. They predict dilated cardiomyopathy development among relatives, years before disease. Consequently, the genetic basis of myocarditis/dilated cardiomyopathy may be established by cardiac-specific and disease-specific antibodies of IgG class biomarkers for identifying 'at risk' relatives as well as patients. Caforio et al., "Genetically determined myocarditis: clinical presentation and immunological characteristics" *Curr Opin Cardiol.* 23:219-226 (2008).

Autoimmune lymphoproliferative syndrome (ALPS) may be the first autoimmune hematological disease whose genetic basis has been defined. It is believed to be a disorder of apoptosis in which the inability of lymphocytes to die leads to lymphadenopathy, hypersplenism, and autoimmune cytopenias of childhood onset. Studies have determined that patients with germline mutations of the intracellular domain of Fas protein, the most frequent single genetic cause of ALPS, have a significantly increased risk of developing Hodgkin and non-Hodgkin lymphoma (NHL), underscoring the role played by cell surface receptor-mediated apoptosis in eliminating redundant proliferating lymphocytes with autoreactive and oncogenic potential. The major determinants of morbidity and mortality in ALPS are the severity of the autoimmune disease, hypersplenism, asplenia-related sepsis, and the risk of lymphoma, which in itself requires long-term surveillance. Rao et al., "Causes and consequences of the autoimmune lymphoproliferative syndrome" *Hematology* 11:15-23 (2006)

E. Genetic Influences on Pulmonary Disease

Chronic obstructive pulmonary disease (COPD) is the fourth leading cause of death worldwide and an accelerating decline of lung function is the earliest and a major indicator of the onset of COPD. Therefore it has become necessary to understand the genetic basis of this complex physiological trait in order to determine the potential susceptibility factors of this disease. REINHARD et al (2005) performed the genome wide linkage analysis study with inbred mice having extremely divergent lung function (C3H/HeJ versus JF1/Msf) and identified multiple Quantitative Trait Loci (QTLs) on mouse chromosomes (mCh) 5, 15, 17, and 19 with Logarithm of odd (LOD) scores> or =4. Significant linkages to total lung capacity (TLC) were detected on mCh 15 and 17, to dead space volume (VD) and lung compliance (C(L)) on mCh 5 and 15, to C(L) on mCh 19, and to diffusing capacity for CO (D(co)) on mCh 15 and 17. Several of the mouse chromosomal regions identified were syntenic to human chromosomal regions identified with linkage to FEV1 (forced expiratory volume-1 second), FVC (forced vital capacity), or FEV1/FVC in separate studies. Using a systematic approach of expression QTL (e-QTL) strategy and exon-wise sequencing of suggested candidate genes followed by predicted protein structure and property, four candidate genes for lung function have been proposed in mice. These genes include, but are not limited to, are superoxide dismutase 3, extracellular [SOD3; mCh 5: V(D)], trefoil factor 2 (TFF2; mCh 17: TLC and D(co)), ectonucleotide pyrophosphatase/phosphodiesterase 2 (ENPP2; mCh 15:TLC and C(L)), and relaxin 1 (RLN1; mCh 19; CL and CL/TLC). As a part of functional validation, gene-targeted $Sod3^{-/-}$ mice were detected with increased conducting airway volume (V(D)/TLC) compared with strain-matched control $Sod3^{+/+}$ mice, consistent with the QTL on mCh 5. Findings with gene-targeted mice suggested that SOD3 is a contributing factor defining the complex trait of conducting airway volume. The human variation in these genes needs further study both in lung development and in the development of lung disease as a part of translational approach. Ganguly et al., "Association studies of lung function in mice" *Dtsch Tierarztl Wochenschr.* 115:276-284. (2008).

Cystic fibrosis was observed to be an autosomal recessive genetic disorder linked to chromosome 7q in several families. Expression of the disease varies, but the genetic basis for clinical heterogeneity is unknown. One extended consanguineous family with pulmonary disease and the sweat gland phenotype of cystic fibrosis had a mild clinical expression of the disease (i.e., for example, manifested by the absence of severe childhood lung disease and increased longevity) with better functional status than that expected for age. The degree of pancreatic exocrine insufficiency varied (4/10), but the older patients had normal pancreatic function. The pedigree suggested the likelihood of common ancestry, and eight of the ten affected persons were clearly related. At least three of the family members with the mildest clinical disease had consanguineous parents and may therefore have been homozygous for a variant cystic fibrosis gene. The mild expression of cystic fibrosis in this family provides evidence for a form of cystic fibrosis that is intrinsically less debilitating than the classic form. Knowles et al., "Mild cystic fibrosis in a consanguineous family" *Ann Intern Med.* 110:599-605 (1989).

The etiology of allergic bronchopulmonary aspergillosis (ABPA) is not well understood. A clinical phenotype resembling the pulmonary disease seen in cystic fibrosis (CF) patients can occur in some individuals with ABPA. Reports of familial occurrence of ABPA and increased incidence in CF patients suggest a possible genetic basis for the disease. To test this possibility, the entire coding region of the cystic fibrosis transmembrane regulator (CFTR) gene was analyzed in 11 individuals who met strict criteria for the diagnosis of ABPA and had normal sweat electrolytes (< or =40 mmol/liter). One patient carried two CF mutations (deltaF508/R347H), and five were found to carry one CF mutation (four deltaF508; one R117H). The frequency of the deltaF508 mutation in patients with ABPA was significantly higher than in 53 Caucasian patients with chronic bronchitis (P<0.0003) and the general population (P<0.003). These results suggest that CFTR plays an etiologic role in a subset of ABPA patients. Miller et al., "Cystic fibrosis transmembrane conductance regulator (CFTR) gene mutations in allergic bronchopulmonary aspergillosis" *Am J Hum Genet.* 59:45-51 (1996).

F. Genetic Influences on Pancreatic Disease

Progress in understanding pancreatic diseases has been limited by a number of factors. Primary problems include the absence of good animal models, and difficulty in understanding the origin of pancreatic disease since the disease is usually manifest by the progressive destruction of the gland itself. The human genome project has allowed mapping and identification of hereditary pancreatitis genes, including, but not limited to, cationic trypsinogen (PRSS1). Whitcomb D C., "Hereditary pancreatitis: a model for understanding the genetic basis of acute and chronic pancreatitis" *Pancreatology* 1:565-570 (2001)

Tropical pancreatitis (TP) refers to a severe type of idiopathic chronic pancreatitis that develops in children in tropical regions of Africa and southern Asia. Recently, an association was identified between idiopathic pancreatitis in the USA and Europe and mutations in the serine protease inhibitor, Kazal type 1 (SPINK1) gene (i.e., for example, pancreatic secretory trypsin inhibitor, PST1). Two disease-associated SPINK1 mutations have been detected (N34S/IVS1–37T>C and IVS3+2T>C) in 6 of 8 patients from Bangladesh with FCPD but not in 4 patients with TCP (p<0.03) or 4 controls (p<0.03). Consequently, a mutated SPINK1 may increases the risk of developing a variety of pancreatic diseases, possibly through a chronic elevation of active trypsin within the pancreas. Rossi et al., "SPINK1/PST1 mutations are associated with tropical pancreatitis in Bangladesh. A preliminary report" *Pancreatology* 1:242-245 (2001).

Altered frequencies of alpha 1 antitrypsin phenotypes have been reported in patients with chronic pancreatitis, suggesting a possible genetic basis for individual susceptibility to this disease. Alpha 1 antitrypsin phenotypes, with particular regard to alcoholic pancreatitis, were studied. Patients with alcoholic pancreatitis were compared with alcoholic control subjects with no history of pancreatic disease. Serum alpha 1 antitrypsin concentrations were raised in pancreatitis patients sampled within one month of an acute attack of pancreatitis, but otherwise values were similar to those of control subjects. There were no significant differences in alpha 1 antitrypsin phenotypes between alcoholics with pancreatitis and alcoholic control subjects. This study of alpha 1 antitrypsin phenotypes provides no evidence of an inherited susceptibility to alcoholic pancreatitis. Haber et al., "Alpha 1 antitrypsin phenotypes and alcoholic pancreatitis" *Gut.* 32:945-948 (1991).

G. Genetic Influences on Muscular Disease

The genetic basis of many muscular disorders, including many of the more common muscular dystrophies, have been widely reported. Clinically, recent genetic advances have improved diagnostic capabilities, but they have not yet provided clues about treatment or management. It is also unlikely that advances in gene therapy will significantly alter clinical treatment in the near future. Lovering et al., "The muscular dystrophies: from genes to therapies" *Phys Ther. December;* 85:1372-1388 (2005).

The genetic basis for many inherited myopathies and muscular dystrophies have been identified. For example, diseases have been found to result from loss of function of structural components of the muscle basal lamina (e.g., MCD1A), sarcolemma (e.g., the sarcoglycanopathies), nucleus (e.g., EDMD) and sarcomere (e.g., the nemaline myopathies). A few have been associated with abnormalities in the genes for muscle enzymes (e.g., calpain and fukutin). Alternate mechanisms of pathogenesis have also recently been suggested by mutations lying outside of coding regions, such as the "field effect" of chromosomal mutations in DM2. Wagner K R., "Genetic diseases of muscle" *Neurol Clin* 20:645-678 (2002).

In particular, the genetic basis of muscle disease has grown dramatically over the last few years. For example, genetic tests are now available for the diagnosis of several conditions and molecular research is providing greater understanding of pathogenesis. Duchenne and Becker muscular dystrophies have been reported to have underlying allelic disorders that differ in age of onset and severity. At the genetic level, these diseases are believed to have different types of mutations, one giving total protein loss (i.e., for example, Duchenne's disease) whereas the other results in a less severe deficiency (i.e., for example, Becker's disease). Also, facioscapulohumeral muscular dystrophy is associated with deletion involving repeated DNA in the sub-telomeric region of the human chromosome 4, although no single gene responsible for this disorder has yet been identified. Nonetheless, it is believed that gene deletion size correlates with disease severity. Limb girdle muscular dystrophies share similar phenotypes, but genetic and protein studies show mutation in very different types of protein (i.e., for example, a protease) may be responsible for the different phenotypes. There are now two forms of myotonic dystrophy, both caused by what are called gene expansions (i.e., for example, an increased number of triplet repeats). Bindoff et al., "The genetic basis of muscle disease" *Tidsskr Nor Laegeforen* 123:2588-2592 (2003).

The congenital muscular dystrophies are a heterogeneous group of inherited disorders. The clinical features range from severe and often early fatal disorders to relatively mild conditions compatible with survival into adult life. The recent advances in the genetic basis of congenital muscular dystrophies have allowed to significantly improve our understanding of their pathogenesis and clinical diversity. These advances have allowed classification of these forms according to a combination of clinical features and primary biochemical defects. In this review we present how the congenital muscular dystrophies field has evolved over the last decade from a clinical and genetic point of view. Muntoni et al., "The congenital muscular dystrophies in 2004: a century of exciting progress" *Neuromuscul Disord.* 14:635-49 (2004).

The hereditary neurodegenerative disease spinal muscular atrophy (SMA) with childhood onset is believed one of the most common genetic causes of infant mortality. The disease is characterized by selective loss of spinal cord motor neurons leading to muscle atrophy. It has been widely reported that this neuronal loss is the result of mutations in the survival motor neuron (SMN) gene. The SMN protein has been implicated in diverse nuclear processes including splicing, ribosome formation and gene transcription. Even though the genetic basis of SMA is well understood, it is not clear how defects in these ubiquitous processes result in motor neuron degeneration leaving other tissues unaffected. Recent evidence from animal and cell culture models of SMA points to roles for SMN in neurite outgrowth and axonal transport. Disruption of these functions might be particularly detrimental to motor neurons given their high metabolic demands and precise connectivity requirements, thus providing a possible explanation for the specificity of motor neuron susceptibility in SMA. Briese et al., "Is spinal muscular atrophy the result of defects in motor neuron processes?" *Bioessays September;* 27:946-957 (2005).

One mutation for muscle development in sheep comprises the callipyge (CLPG) gene, which causes a postnatal muscle hypertrophy that is localized to the pelvic limbs and loin. Enhanced skeletal muscle growth is also observed in animals with the Carwell (or rib-eye muscling) mutation, and a double-muscling phenotype has been documented for animals of the Texel sheep breed. However, the actual mutations responsible for these muscular hypertrophy phenotypes in sheep have yet to be identified. Cockett et al., "The callipyge mutation and other genes that affect muscle hypertrophy in sheep" *Genet Sel Evol.* 37 Suppl 1:S65-S81 (2005).

H. Genetic Influences on Bone Disease

Osteoporosis is a common disease with a strong genetic component characterized by reduced bone mass and an increased risk of fragility fractures. Twin and family studies have shown that genetic factors contribute to osteoporosis by influencing bone mineral density (BMD), and other phenotypes that are associated with fracture risk, although the heritability of fracture itself is modest. Linkage studies have identified several quantitative trait loci that regulate BMD but most causal genes remain to be identified. In contrast, linkage studies in monogenic bone diseases have been successful in gene identification, and polymorphisms in many of these genes have been found to contribute to the regulation of bone mass in the normal population. Population-based studies have identified polymorphisms in several candidate genes that have been associated with bone mass or osteoporotic fracture, although individually these polymorphisms only account for a small amount of the genetic contribution to BMD regulation. Ralston S. H., "Genetics of osteoporosis" *Proc Nutr Soc.* 66:158-165 (2007).

Fanconi anemia (FA) is a rare hereditary disease characterized by bone marrow failure and developmental anomalies. The genetic basis of FA is believed to be mutations in any one of the known FA genes. The function of the proteins is largely unknown, but many form complexes with each other, and in one canonical "pathway," eight of the known FA proteins bind together in a complex and monoubiquitinate FANCD2, a protein not present in the core complex. Monoubiquitinated FANCD2 translocates to damage-induced nuclear foci containing BRCA1, BRCA2, and Rad51, thereby protecting the genome. There is strong in vitro and in vivo evidence that at least some of the FA proteins promote survival signaling pathways in hematopoietic cells by forming complexes with signaling molecules. Bagby et al., "Fanconi anemia" *Semin Hematol.* 43:147-156 (2006).

I. Genetic Influences on Blood Disorders

Type 1 von Willebrand disease (VWD) is a form of VWD and is believed to have a genetic basis: For example, linkage analysis demonstrates that dominantly inherited, fully penetrant VWD is present in approximately 50% of type 1 families. Between 55 and 70% of index cases analyzed have a candidate von Willebrand factor gene (VWF) mutation, but no mutations are present in the promoter, or protein coding sequences or splice sites. Nonetheless, missense mutations occur throughout VWF associated genes. Currently, it is believed that Type 1 von Willebrand disease can be divided into two primary genotype groups: i) fully penetrant VWF mutations expressed by low plasma von Willebrand factor and bleeding; and ii) VWF mutation acting as a risk factor for bleeding in combination with blood group O. Goodeve A., "Genetics of type 1 von Willebrand disease" *Curr Opin Hematol.* 14:444-449 (2007).

Thrombophilia can best be defined as a disorder of coagulation that contributes to a predisposition towards thrombosis. Although the term thrombophilia has been used to describe arterial thrombosis, its most common usage has been in reference to venous thromboembolism (VTE). Thrombophilia can be a consequence of both acquired and inherited or genetic causes. Acquired causes include conditions such as surgery, cancer, and prolonged immobilization, while genetic causes have been linked to the inherited deficiencies of antithrombin, protein C, and protein S. The identification of the genetic basis of these inherited causes of thrombophilia ushered in a new way of thinking about thrombosis and the importance of its genetic component. Interest in the genetic basis of VTE was accelerated with the subsequent discovery of factor V Leiden, prothrombin G20210A, and MTHFR C677T. These single nucleotide polymorphisms (SNPs) and other genetic variants associated with VTE have become fixtures in the molecular diagnosis of inherited thrombophilia. Because of the large volume of current and anticipated future genetic testing, there has been a push to develop many different genotyping methods which are now used in both clinical and research settings. The identification of new genetic variants that may either directly or indirectly affect coagulation or the anticoagulant pathway, may greatly advance the understanding and clinical management of thrombophilia. League et al., "Molecular diagnostics of inherited thrombosis" *Clin Lab Sci.* 18:271-279 (2005).

J. Genetic Influences on Sleep Disorders

Sleep disorders are believed to arise by an interaction between the environment and the genetic makeup of the individual but the relative contribution of nature and nurture varies with diseases. At one extreme are the disorders with simple Mendelian patterns of inheritance such as familial advanced sleep phase syndrome, and at the other extreme are diseases such as insomnia, which can be associated with a multitude of medical and psychiatric conditions. Despite this knowledge, identification of susceptibility genetic loci for complex diseases such as obstructive sleep apnea has yet to be identified. Raizen et al., "Genetic basis for sleep regulation and sleep disorders" *Semin Neurol.* 26:467-483 (2006).

The molecular basis of one autosomal dominant form of familial advanced sleep phase syndrome has been identified as due to mutations in the human period 2 gene. Further, genetic studies in an autosomal recessive canine model of narcolepsy and in gene-targeted mice have identified the hypothalamic hypocretin (orexin) neuropeptide system as a target for human narcolepsy. The study of the role of genes in the obstructive sleep apnea syndrome is likely to integrate with respiratory, cardiovascular, and metabolic dysfunction. Current research is focused on role of genetic factors in the obstructive sleep apnea syndrome, restless leg syndrome, narcolepsy, and circadian rhythm disorders. Taheri S., "The genetics of sleep disorders" *Minerva Med.* 95:203-212 (2004).

Several sleep disorders are believed to have a genetic basis. These conditions include, but are not limited to, the narcoleptic syndrome, sleep walking, periodic movements in sleep, circadian delay syndromes and familial insomnia. These disorders illustrate different control mechanisms involved in sleep and wakefulness, including but not limited to, those determining the prevalence and timing of NREM and REM activity, somatomotor inhibition and excitation, autonomic discharge, and the circadian framework of sleep. For example, one genetic defect in narcolepsy has been localized to the short arm of chromosome 6, but the chromosomal localizations of the genetic basis for the other disorders are not known. Parkes et al., "Genetic factors in sleep disorders" *J Neurol Neurosurg Psychiatry June; Suppl:* 101-108 (1989).

VII. Derivation of Contact Probability Scaling

Contact probability may be derived as a function of distance for fractal globules and, en passant, for finite iterations of Peano curves in d dimensions. For example, predictions of the theory may be illustrated with simulations exploring a variety of Peano curves and exhibiting a previously unexplored family of power-law scalings that emerge.

Contact probability P(x) may be described as a function of distance x along a fractal globule. Note that the same argument works well for finite iterations of Peano curves in an arbitrary number of dimensions, since their structure is analogous. As such, the argument here will be stated for d dimensions. Iactual(x) may be defined as the number of actual interactions between loci separating by a distance x along the 1D polymer contour, and Ipossible(x) as the number of pairs of loci separated by a distance x along the polymer contour. Then by definition we have:

$$P_{contact}(x) = \frac{I_{actual}(x)}{I_{possible}(x)}$$

Figure 30:
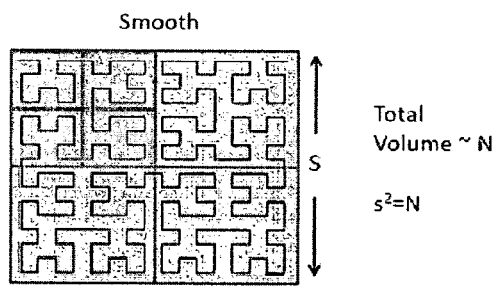
FIG. 30 illustrates a sketch of calculation for a 2D Hilbert Curve, comparing two consecutive iterations.

Let us compare the contact probability at two consecutive iterations of the space-filling fractal. See, FIG. 30. At the larger of the scales we have $2^d$ cubes, each of which contains $N/2_d$ monomers and at the smaller scale we have $2^{2d}$ cubes, each of which contains $N/2^{2d}$ monomers.

The total actual number of interactions satisfies:

$$I_{actual} = (\text{number of cubes}) \times (\text{interactions/cube})$$

We get the following value at the large scale:

$$I_{actual}\left(\frac{N}{2^d}\right) \approx 2^d f\left(\frac{N}{2^d}\right)$$

where $f$ is a function governing the number of local interactions per cube (blob) which we will discuss further below. At the small scale we obtain:

$$I_{actual}\left(\frac{N}{2^{2d}}\right) \approx 2^{2d} f\left(\frac{N}{2^{2d}}\right)$$

The number of possible interactions at the large scale is simply $\sim N^2$. At a smaller scale, the number of interactions is the product of the number of possible interactions within a cube (blob) times the number of such cubes $2^d$. We get the following values at the large and small scale:

$$I_{possible}\left(\frac{N}{2^d}\right) \approx N^2$$

$$I_{possible}\left(\frac{N}{2^{2d}}\right) \approx 2^d \left(\frac{N}{2^d}\right)^3 = \frac{N^2}{2^d}$$

Combining and $I_{actual}(x)$ and $I_{possible}(x)$, we obtain:

$$P_{contact}\left(\frac{N}{2^d}\right) = \frac{2^d}{N^2} f\left(\frac{N}{2^d}\right)$$

and $$P_{contact}\left(\frac{N}{2^{2d}}\right) = \frac{2^{3d}}{N^2} f\left(\frac{N}{2^{2d}}\right)$$

Thus we have:

$$\frac{P_{contact}\left(\frac{N}{2^{2d}}\right)}{P_{contact}\left(\frac{N}{2^d}\right)} = 2^{2d} \frac{f\left(\frac{N}{2^{2d}}\right)}{f\left(\frac{N}{2^d}\right)}$$

Figure 31:
FIG. 31 illustrates a sketch of smooth and interdigitated cases.
Figure 32:
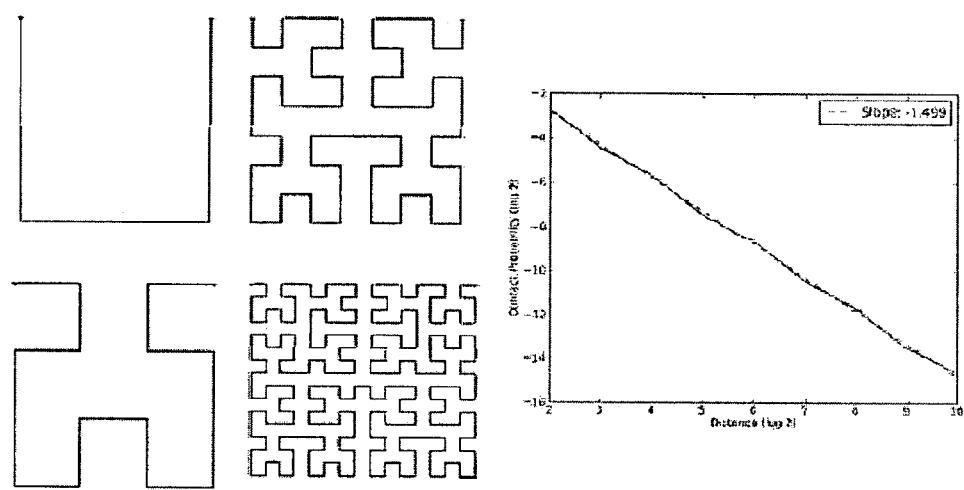
FIG. 32 presents one embodiment of a Hilbert Curve in 2 Dimensions, $\alpha_{smooth}=-3/2$.
Figure 33:
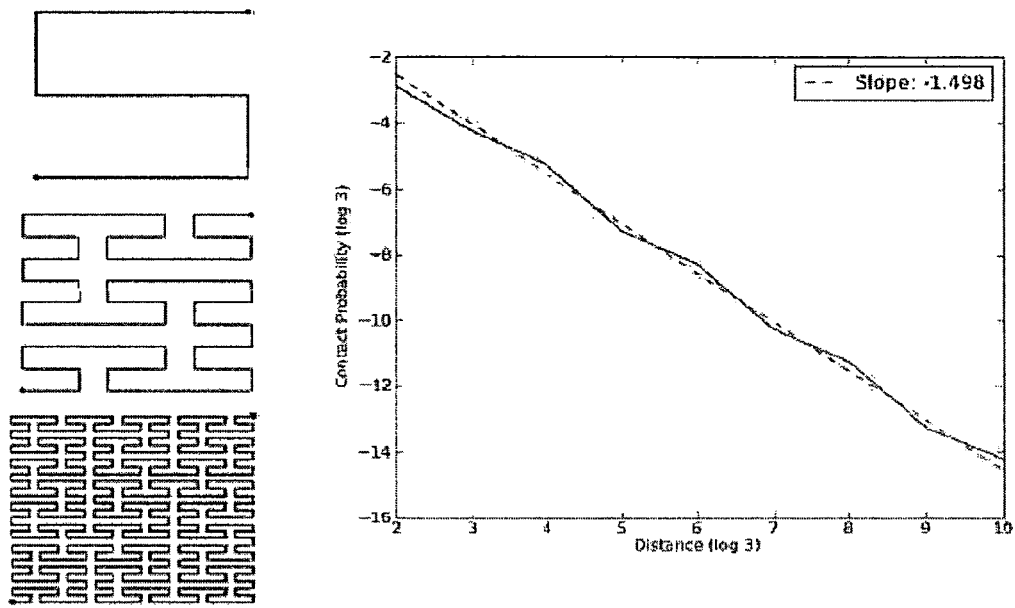
FIG. 33 presents one embodiment of a Peano Curve in 2 Dimensions, $\alpha_{smooth}=-3/2$.
Figure 34:
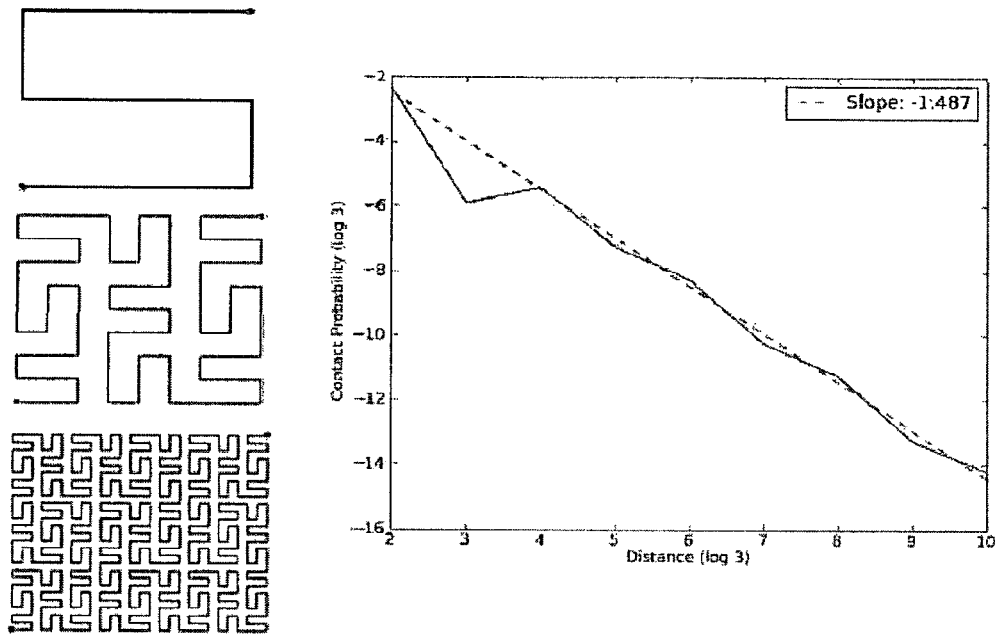
FIG. 34 presents one embodiment of a Symmetrized Peano Curve in 2 Dimensions, $\alpha_{smooth}=-3/2$.
Figure 35:
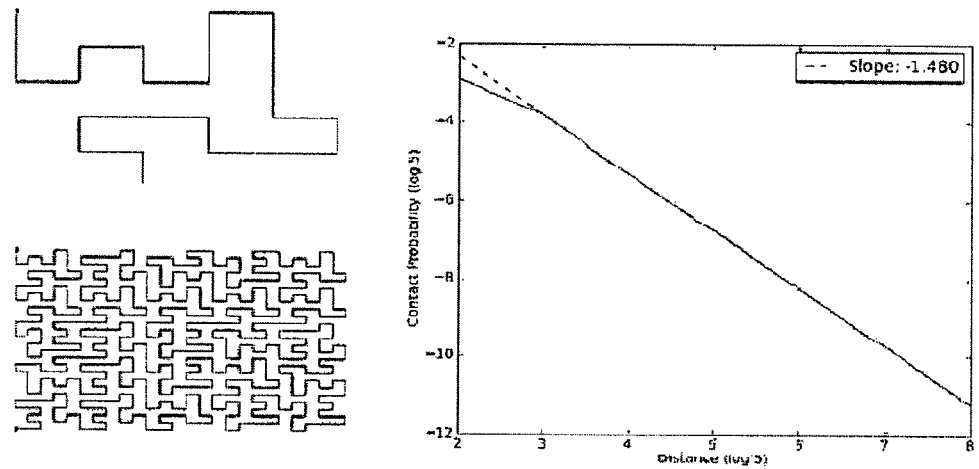
FIG. 35 presents one embodiment of a Quadratic Gosper Curve in 2 Dimensions, $\alpha_{smooth}=-3/2$.
Figure 36:
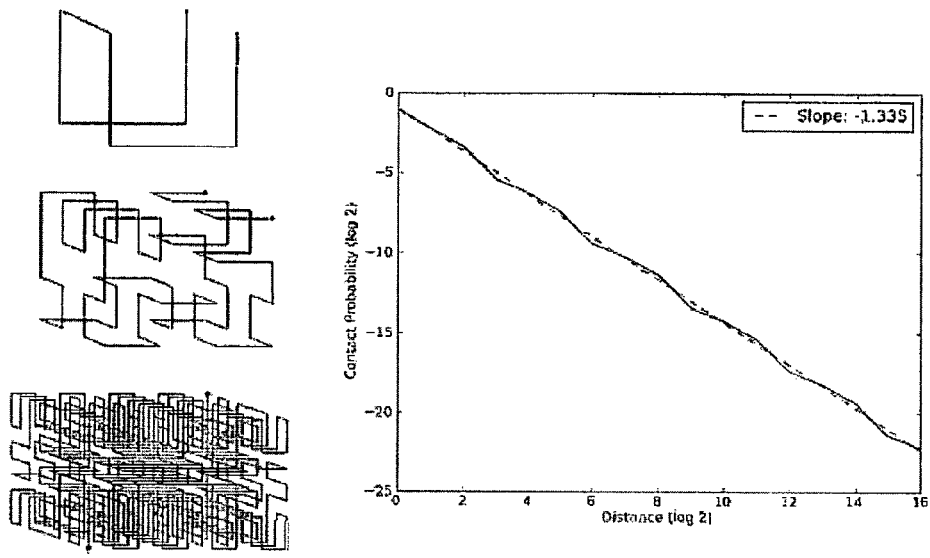
FIG. 36 presents one embodiment of a Hilbert Curve in 3 Dimensions, $\alpha_{smooth}=-4/3$.
Figure 37:
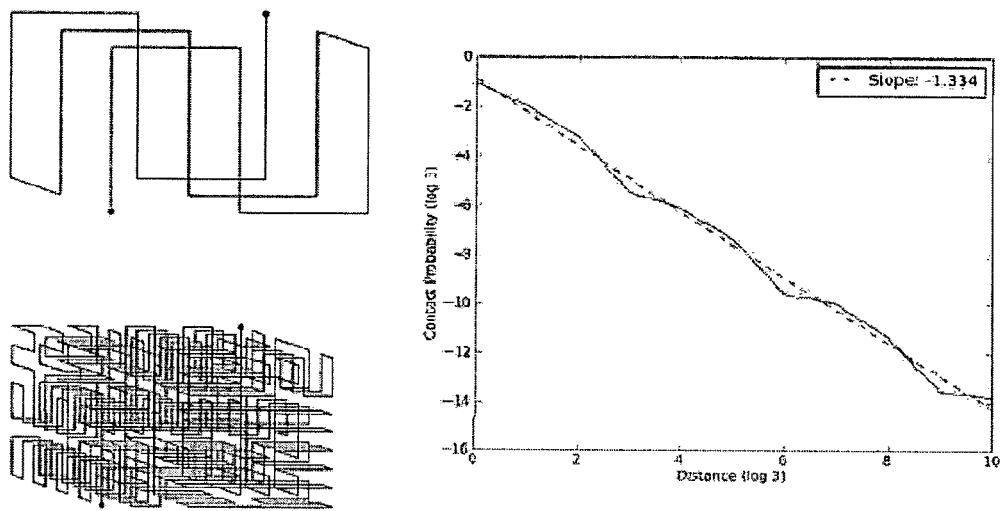
FIG. 37 presents one embodiment of a Peano Curve in 3 Dimensions, $\alpha_{smooth}=-4/3$.
Figure 38:
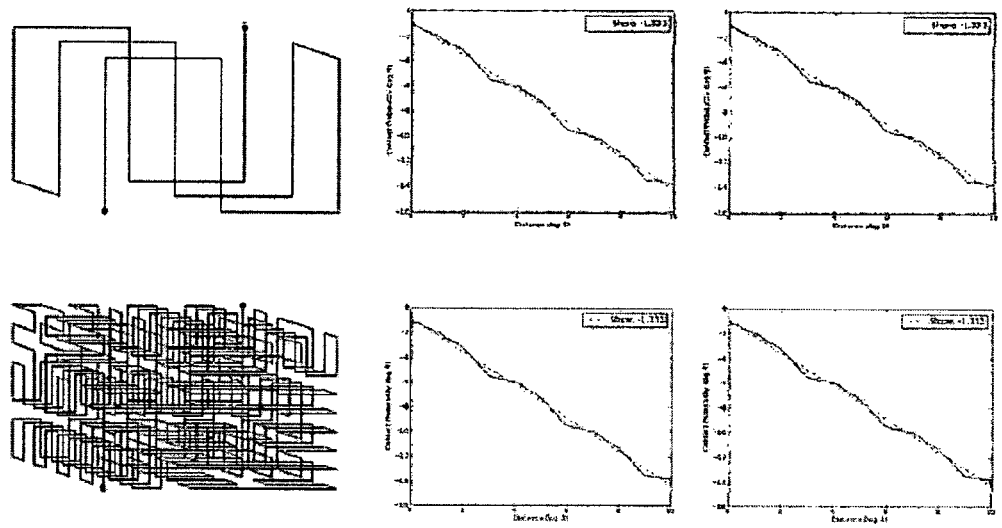
FIG. 38 presents one embodiment of a Randomized Peano Curve in 3 Dimensions, $\alpha_{smooth}=-4/3$. The elementary motif may be rotated in 3 different ways (or left intact) without affecting the starting position or ending position. To create the randomized curve, at each iteration, one of these four options is chosen for each subregion of the curve.
Figure 39:
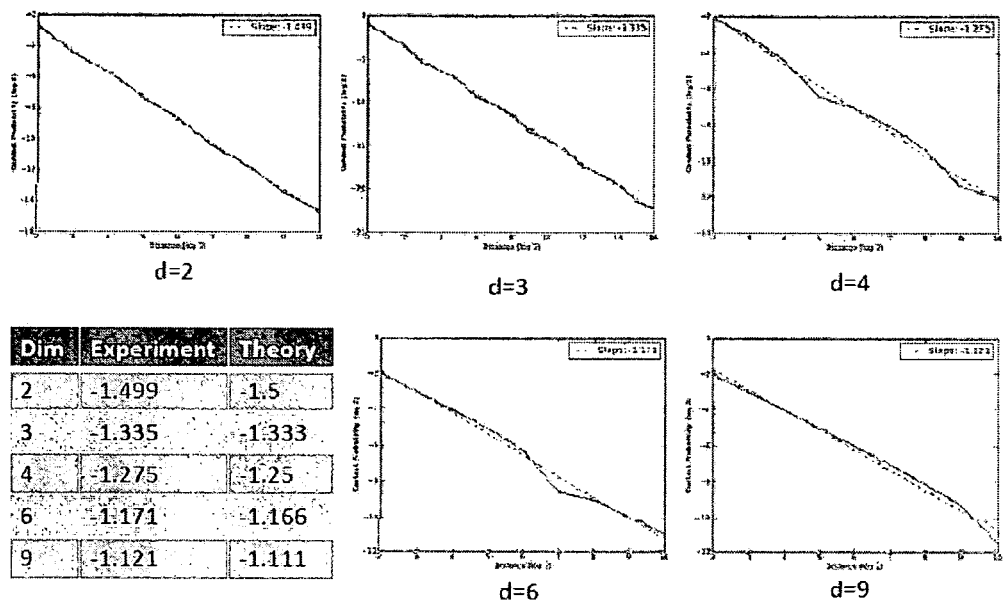
FIG. 39 presents one embodiment of a Hilbert Curve in many dimensions (2, 3, 4, 6, 9); $\alpha_{smooth}=-(1+1/d)$.
Figure 40:
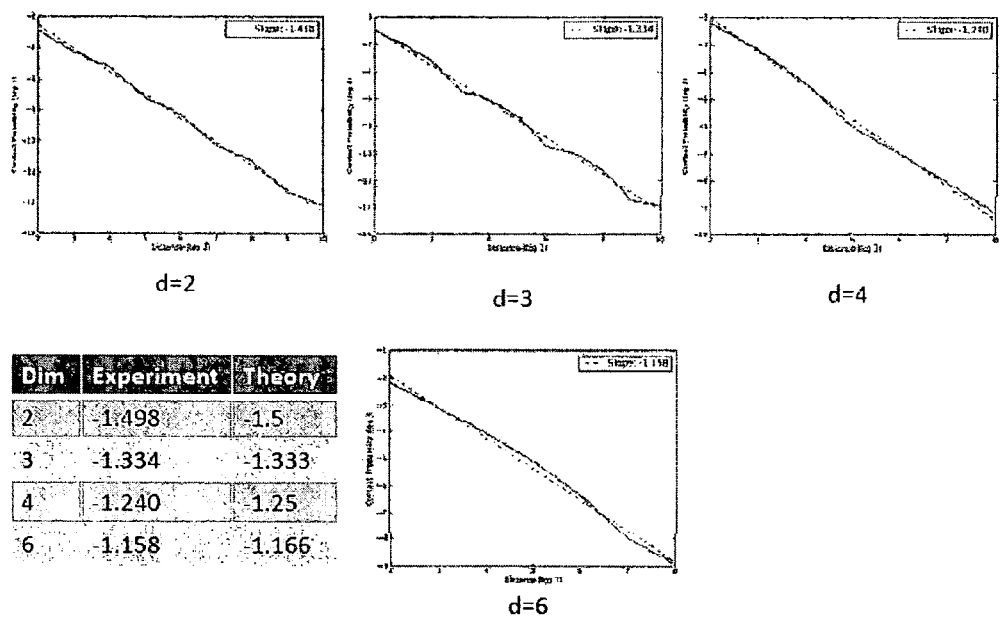
FIG. 40 presents one embodiment of aPeano Curve in many dimensions (2, 3, 4, 6); $\alpha_{smooth}=-(1+1/d)$.

There are two cases to address: where the globules have smooth surfaces where interactions occur along the surface (such as in the Hilbert Curve), or where two globules interpenetrate as they meet, and interaction density is proportional to volume (such as DNA and chromatin. See, FIG. 31. Vettorel et al., *Phys Biol* 6:25013 (2009). For smooth globules, $f(x)$, the local density of interactions, is proportional to the surface area in d−1 dimensions, and thus scales with $X^{d-1/d}$. Thus we obtain:

$$\frac{P_{contact}\left(\frac{N}{2^{2d}}\right)}{P_{contact}\left(\frac{N}{2^d}\right)} = 2^{2d} \frac{c \frac{N}{2^{2d}}}{c \frac{N}{2^d}} = 2^d$$

In both these cases we find that P exhibits scalefree behavior and is of the form $kx^\alpha$. In general if we have $$P(x) = kx^\alpha$$

and $$\frac{P\left(\frac{x}{2^d}\right)}{P(x)} = \beta \text{ then: } \frac{\left(\frac{x}{2^d}\right)^\alpha}{x^\alpha} = \beta \text{ yielding } \alpha = \frac{-\log_2 \beta}{d}.$$

In summary, we find that $P_{contact}(x) = kx^\alpha$, where $\alpha$ is given by $$\alpha_{smooth} = -\left(1 + \frac{1}{d}\right)$$

and $$\alpha_{interdigitated} = -1.$$

The smooth case may be illustrated in silico using Peano curves. See, FIGS. 33-40. The behavior of interphase DNA reflects the interdigitated case.

VIII. Monte Carlo Simulations

Polymer conformations were modeled that have statistical properties similar to those observed in chromatin at megabase length-scales. Two possible models of the polymer packing were analyzed: the equilibrium globule and the fractal globule. Monte Carlo simulations were used to construct large ensembles of representative conformations for both models. Conformations in both ensembles have densities comparable to those of the interphase chromatin.

Figure 42:
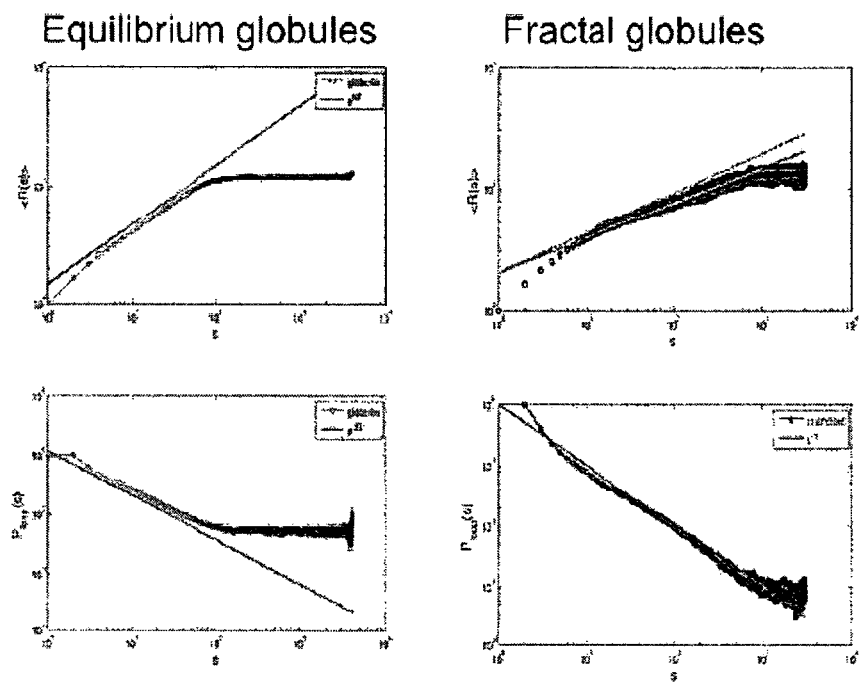
FIG. 42 presents representative statistical properties of equilibrium and fractal globules. Upper row: The mean end-to-end distance vs. contour length, averaged over 100 conformations. For the crumpled globules we show the average within individual conformations (blue dots) and the average over the ensemble (black dots). The scaling $s^{0.29}$ provides the best fit to the data (solid red). The scaling $s^{1/3}$ shown by the dashed line constitutes an upper limit that is closely approached by individual conformations. Lower row. The probability of a contact between two points separated by contour length s. Simulated structures show very good agreement with the differing theoretical predictions for the two models.

The chromatin fiber was modeled by a polymer chain of N=4000 freely-joined spherical monomers connected by hard bonds. The distance between the centers of consecutive monomers is equal to their diameter, such that the chain is continuous. See, FIG. 42. These spheres thus define an excluded volume. The presence of excluded volume is important not only for taking into account steric interactions between the monomers, but also because it suppresses nonphysical, topology-violating moves where one fragment of the chain goes across the other one. Occasionally, excluded volumes are turned off, wherein the chains are referred to as phantoms.

Figure 41:
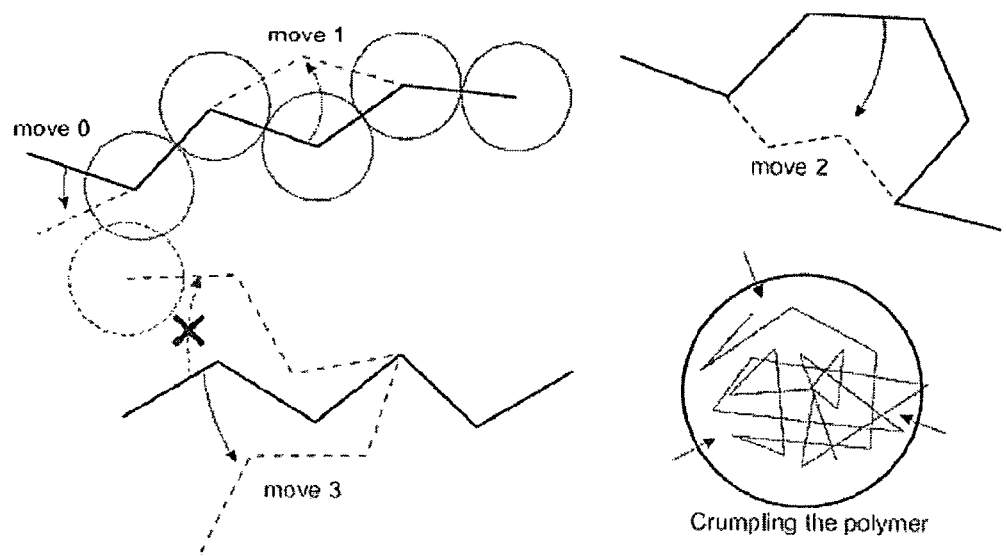
FIG. 41 illustrates several representative moves of a Monte Carlo procedure.

The dynamics of the polymer chain are simulated by a standard Metropolis Monte Carlo procedure that involves numerous moves: See, FIG. 41. Binder K., In Monte Carlo and molecular dynamics simulations in polymer science (Oxford University Press, New York, 1995), pp. 587; Shimada et al., *J Mol Biol* 308:79 (2001); and Vologodskii et al., *J Mol Biol* 227:1224 (1992):

0. displacement of the terminal monomers;
1. random rotation of monomer i around axis connecting the i–1$^{st}$ and i+1$^{st}$ monomers;
2. generating a random conformation of 3 consecutive monomers, while keeping all the bond lengths constant.
3. rotating a fragment of the chain between a monomer i and one of the termini by a random angle.

The latter move has been used only for initial compaction of the chain, but was eliminated later to avoid knotting of the chain through topologically impossible moves. This is useful when simulating the crumpling of a fractal globule, which is governed primarily by topological factors. Moves that lead to collisions between the monomers are rejected, except in the phantom chain.

To obtain conformations of sufficiently high density, the polymer was confined into a spherical cage of radius $R_0$ and modeled by an exponentially increasing external potential:

$$U_{(r)} = e^{(r-R0)\sigma}$$

Equilibrium Globule

An equilibrium globule is believed to be a macroscopic state of a polymer reached after it has collapsed in: i) the presence of a poor solvent (i.e., in the presence of attractive interactions between the monomers); or ii) confined into a spherical cage. A. I. U. Grosberg, Khokhlov, A. R., In: Statistical physics of macromolecules, AIP series in polymers and complex materials (AIP Press, New York, 1994), pp. 350. A spherical cage method was used to determine equilibrium conformations described herein. The protocol may include, but is not limited to: (1) confinement and equilibration of the phantom chain in a small cage (i.e., with excluded volume off); and (2) equilibration of the non-phantom chain in a larger cage reflecting a realistic interphase volume. The initial phantom stage is essential for efficiency as it allows the chain to obtain entangled (knotted) conformations of the polymer that are part of the equilibrium ensemble but hard to achieve by equilibration of the confined non-phantom chain. Specifically, the first stage consists of 2500×N steps of gradual polymer confinement and 4000×N steps of equilibration in the cage of $R_0$=16 (in the units of the bond length). The second stage involves 1500×N steps during which the excluded volume is gradually reintroduced. During this stage, the natural expansion of the chain in response to the presence of excluded volume is counteracted by compression into a cage of $R_0$=11, such that the radius of gyration of the chain stays approximately constant. Finally, the chain is equilibrated for 1000×N further steps until the polymer density in the cage is uniform. Statistical properties of the conformations may be verified by comparing them with theory, and with the reported properties of the conformations obtained by full enumeration on a cubic lattice. Lua et al., *Polymer* 45:717 (2004).

Fractal Globule

A fractal globule (or crumpled globule) is believed to be a transient state of a collapsed or confined polymer. It has been suggested that this state should be very long-lived state due to the topological constraints which prevent rapid knotting. Grosberg et al., *J. Phys. France* 49:2095 (1988. Over a long period of time, the fractal globule gradually transforms into the equilibrium globule through the reptation of the polymer ends. Although it is not necessary to understand the mechanism of an invention, it is believed that it is possible that a genome suppresses this process via anchoring of telomeres or gelation. To obtain conformations corresponding to the fractal globule, the polymer is rapidly crumpled by adiabatically compressing a spherical cage. The simulations begin with 3150×N steps in which the polymer is confined to a cage modeled by the external potential $U_{(r)} = e^{(r-R0)\sigma}$. This cage "chases" the polymer since at every step we dynamically set $R_0 = 0.7 R_{max}$ and $\sigma = R_0/6$ (e.g., $R_{max}$ is the distance from the center of mass to the most remote monomer). Note that a "tail wagging" move (i.e., Move #3, FIG. 41) is turned off after 175×N steps to avoid polymer knotting. After 3150×N steps the cage is set to a fixed radius $R_0$=11, $\sigma$=1.1. In a second stage, we allow the confined polymer to settle for another 3850×N steps, enabling uniform polymer density in the cage to be obtained. Note that the time provided in this step is far too short to allow the chain to reach the equilibrium globular state. The scaling properties of the resulting conformations are very close to the properties of the fractal (crumpled) globule.

The fractal and equilibrium globules were observed to have dramatically different conformations. Statistical properties of the equilibrium and fractal globules obtained are described. See, FIG. 42. Examples of physical representations of the globules themselves are illustrated. See, FIG. 43.

Consider the mean end-to-end distance R(s) for a fragment of contour length s. In the equilibrium globule, theory suggests that the chains traveling within the globule before touching the confining walls behave like Gaussian chains (i.e., random walks) with $R(s) \sim s^{1/2}$. This is the scaling observed in the presently disclosed simulated equilibrium globules. At larger s ($s > R_0^2 \approx 100$) the end-to-end distance saturates due to perfect mixing of the monomers inside the globule. See, FIG. 43. The fractal globule, in contrast, shows a different scaling. According to the theory, the fractal globule consists of the hierarchy of blobs that do not interpenetrate. Each blob constitutes a well-packed fractal globule itself. The volume of a fully packed globule (with a uniform polymer density) should be comparable to that of the total volume of the polymer monomers, i.e. V~s, suggesting that $R^3$~s and $R(s)$~$s^{1/3}$. This scaling in fact is an upper limit, since for any particular conformation a polymer does not fully fill the volume of a blob. In agreement with this argument, simulations show that $R(s)$~$s^{0.29-0.30}$ fits the data best, while $R(s)$~$s^{1/3}$ provides an upper limit that is closely approached. See, FIG. 42.

Comparison of the scaling in the equilibrium and fractal globules clearly demonstrates the marked differences between the two configurations. Similarly, the two models exhibit very different probability of a contact (loop) P(s) between regions separated by distance s along the chain. The equilibrium globule demonstrates $P(s)$~$s^{-3/2}$ for small s, corresponding to the results for a Gaussian chain, and a uniform contact density for larger $s > R_0^2 \approx 100$. The fractal globule demonstrates a very different scaling of $P(s)$~$s^{-1}$, as predicted by the theory (see above), and in good agreement with the intra-chromosomal contact probability we obtained using Hi-C. This latter scaling makes the fractal globule a good statistical model for arrangement of interphase chromatin at the megabase scale.

Topological State of Equilibrium and Fractal Globules

Figure 44:
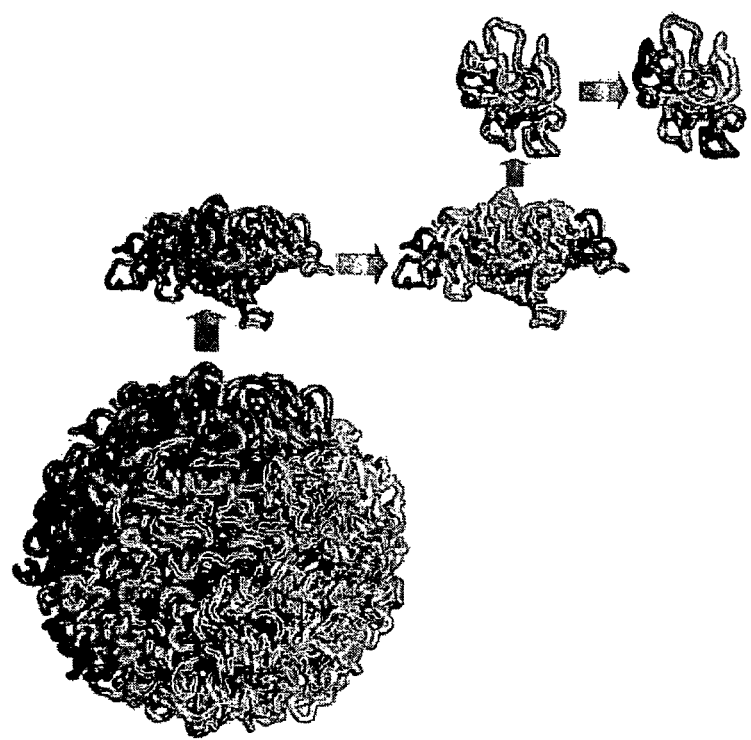
FIG. 44 presents representative hierarchical structure of the fractal globule. Monochromatic domains at one level are isolated and repainted to reveal their domain organization at the next level. One property of the fractal globule is its hierarchical organization, wherein individual domains may be isolated at one level, while comprising well-separated (monochromatic) domains at the next level of folding.

The fractal and equilibrium globule states are expected to have very different topologies. The fractal globule is the state of a collapsed polymer that lacks entanglements, i.e., it should have a largely unknotted conformation. The equilibrium globule, in contrast, has been shown to be highly knotted; only an exponentially small fraction of equilibrium globules are unknotted. Vasilyev et al., *Theoretical and Mathematical Physics* 134:142 (2003); and Kolesov et al., *Nucleic Acids Res* 35:W425 (2007). These predictions were confirmed by the data presented herein. See, FIG. 44 and FIG. 45. These data show that changes in topological state may be quantified using knot-theoretic analysis, and then illustrated its functional consequences on both global and local decondensation.

Knot Invariants

Ensembles of fractal and equilibrium globules obtained by Monte Carlo simulations were compared with theoretical expectations. Several reports using the Alexander and Jones polynomials detect knots in collapsed polymers, and protein structures. Vasilyev et al., *Theoretical and Mathematical Physics* 134:142 (2003); Kolesov et al., *Nucleic Acids Res* 35:W425 (2007); Lua et al., *PLoS Comput Biol* 2:e45 (2006); and Virnau et al., *PLoS Comput Biol* 2:e122 (2006).

A previously developed tool was used to characterize the topological state of the conformations obtained herein. Kolesov et al., *Nucleic Acids Res* 35:W425 (2007); and knots.mit.edu. Since knots are defined only on closed contours, the ends of the polymer need to be connected to test whether the polymer is knotted and to examine the complexity of the knots. To avoid additional crossings introduced by a procedure to connect polymer ends, only those conformations of the fractal and equilibrium globule that have both ends of the chain close to the surface of the globule were selected for analysis ($|r|>11$ units).

Figure 46:
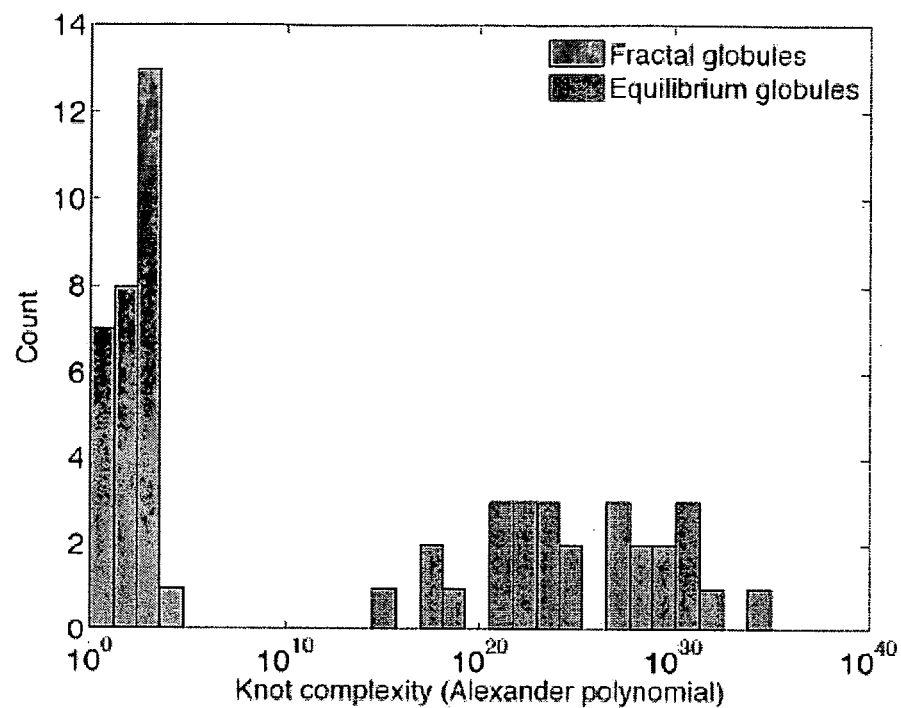
FIG. 46 present representative topological states of fractal and equilibrium globules. The distribution of the values of the Alexander polynomial, a knot invariant, computed for 29 fractal (green) and 27 equilibrium (red) globules. The Alexander polynomial characterizes the degree of complexity of the knot and equals 1 for unknotted chain, 9 for 3-1 knot, 25 for 4-1 knot, etc. For comparison, the most complex knot observed in proteins (6-1) has the value of 81. The polynomial has been computed for closed contours obtained by connecting the ends. Virnau et al., *PLoS Comput Biol* 2:e122 (2006). To avoid spurious knotting due to the endjoining procedure, only conformations with both ends on the surface of the globule have been used.

Values of the Alexander polynomial were computed (i.e., for example, measures of knot complexity) for 29 fractal and 27 equilibrium globules. See, FIG. 46. All of the equilibrium globules exhibited extraordinarily high values of the knot complexity (from ~1020 to ~1030) and are therefore highly knotted. In contrast, the fractal globules were either completely unknotted (>20% of them) or showed only a few crossings (knot complexity ~1-100). The few crossings observed may have been introduced by the large scale Move #3 used for initial polymer compression. As expected, a dramatic difference between the two types of globules was observed.

Global Expansion.

Figure 47:
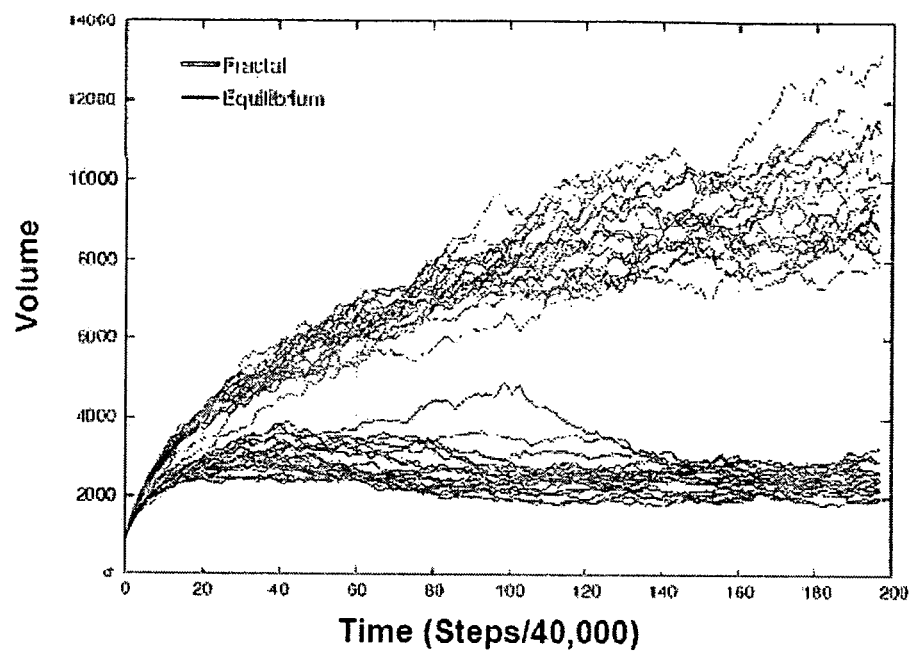
FIG. 47 presents exemplary data showing different expansion rates of fractal and equilibrium globules. When spatial constraints are removed, fractal globules unravel quickly (green); equilibrium globules expand briefly and then halt due to knotting.

To illustrate the functional consequences of the differing degree of knottedness in the fractal vs. equilibrium globules, the effects of a change in solvent conditions was simulated by taking 50 fractal and 50 equilibrium globules and removing the outer wall constraining them. The fractal globules rapidly unraveled. In contrast, the equilibrium globules expanded briefly, but the expansion soon halted because of the large number of knots. See, FIG. 47 and FIG. 48.

Local Expansion

The lack of knots in a fractal globule facilitated not only global, but also local, decondensation. 36 fractal and 40 equilibrium globules were removed from a contraining outer wall that was replaced with an attractive potential constraint. The attractive potential constraint was verified to not destabilized the folded structure. The effects of changing the interaction term for a contiguous region on the polymer were simulated. Such a change might correspond to changes in solubility properties when a chromatin domain gains or loses an epigenetic mark. For fractal globules, this local change in potential led to complete unraveling of the local region. In equilibrium globules, some unraveling was observed, but it was largely suppressed by the presence of knots.

Figure 49:
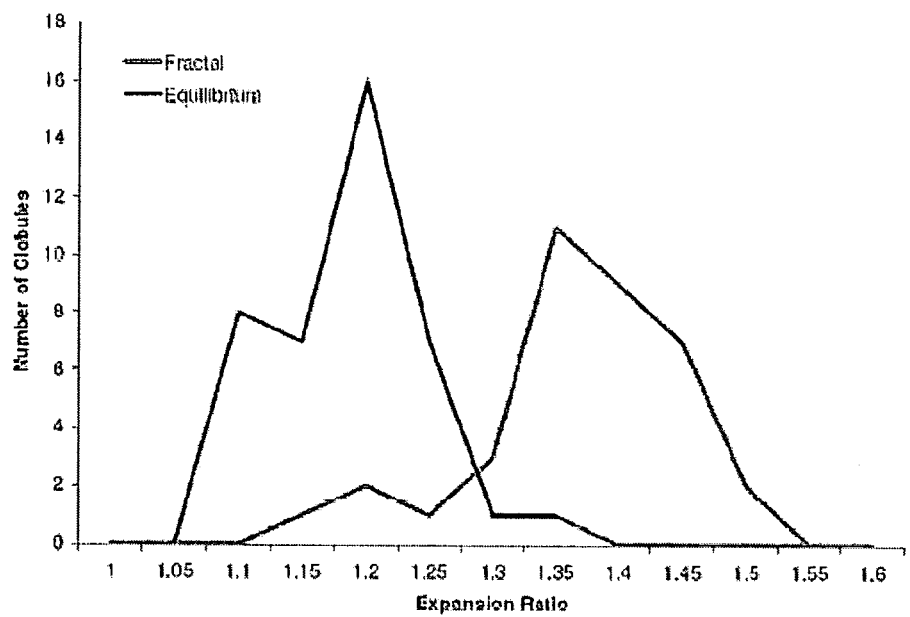
FIG. 49 presents exemplary data showing different expansion rates of local domains within fractal and equilibrium globules. Globules are stabilized by monomer attractions instead of hard boundaries. When the attraction is reversed and becomes repulsive for a subchain, the subchain bulges out of the fractal globule, but does not do so in an equilibrium globule. A ratio is plotted of the mean absolute distance from the globule center of mass after repulsions are introduced vs. mean absolute distance from the globule center of mass before repulsions are introduced. Results are for subchains of length 700 in both fractal (green) or equilibrium (red) globules. These findings suggest that changes in solubility of a chromatin domain due to such factors as changes to epigenetic marks may be sufficient to induce local decondensation in a fractal globule.
Figure 50:
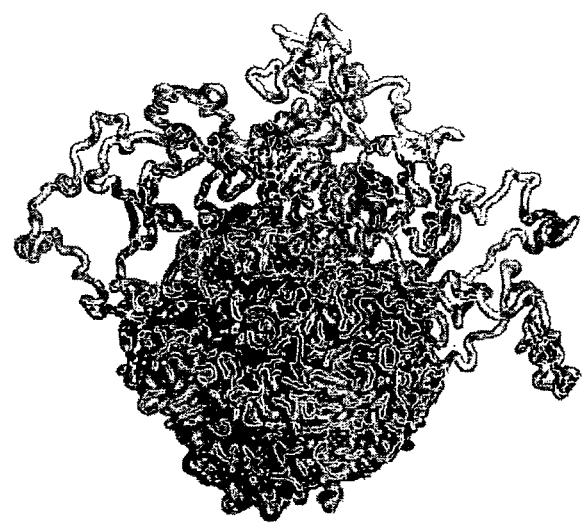
FIG. 50 illustrates that a representative fractal globule subchain unravels when the stabilizing attractive potential is replaced by a repulsive potential.

This effect was quantified by measuring the absolute distance from the perturbed monomers to the center of the globule over time. For fractal globules, this average distance was markedly larger than for equilibrium globules. See, FIG. 49 and FIG. 50

These results suggest that changes in solubility induced by such perturbations as the addition or removal of epigenetic marks may be sufficient to locally remodel chromatin and decondense the modified loci.

Estimate of the Volume Fraction of Chromatin in Human Cells

The Monte Carlo simulations obtained an ensemble of structures that, in their statistical properties, resemble some of the features of chromatin arrangement in the cell. For example, chromatin occupies a significant fraction of an in vivo cell volume, a property that was reproduced in the presently disclosed simulations.

Taking a nuclear diameter of a tissue culture cell to be approximately 5-10 μm, and assuming close to a spherical shape a volume in the range 50-500 $\mu m^3$ would be expected, with a (geometric) mean of ~160 $\mu m_3$. Assuming that chromatin is built of DNA wrapped around nucleosomes, one would expect approximately $6 \times 10^9$ bp/200 bp=$3 \times 10^7$ nucleosomes. Each may be approximated as a cylinder ~10 nm in diameter and ~5 nm in height, suggesting a volume of about 500 $nm^3$ each. The linker DNA after each nucleosome is about 50 bps long, suggesting a volume of about 50*0.34 nm*3.14*1 $nm^2$=50 $nm^3$. Thus, the total volume of chromatin=$550 \times 3 \times 10^7$=16 $um^3$, or ~10% (3-23%) of the nuclear volume. This strikingly large volume fraction is itself a significant underestimate, since all other DNA-bound proteins were ignored. Note that any further packing or localization of chromatin inside the nucleus will increase local density.

In the presently disclosed simulations, the radius of a final crumpled globule was R≈12.5 and the volume V≈8000 cubic units. The total volume of the 4000 monomers, 1 unit in diameters each, is V≈2000. This implies a volume fraction of about 25%, which is consistent with the volume fraction estimated above.

Monomer Length in Base Pairs

Each monomer of the chain corresponds to a fragment of chromatin that equals the Kuhn length of the chromatin fiber, i.e. approximately twice the persistence length of the fiber.

Although the persistence length of the chromatin fiber is unknown it can be estimated using the following arguments. DNA is packed into nucleosomes, where 150 bps are wrapped around the histone core and do not contribute to flexibility of the fiber. The linker DNA of about 50 bps that connects consecutive nucleosomes is bendable, and is the source of flexibility in the fiber. Since the persistence length of double-stranded DNA is 150 bps, an equally flexible region of the nucleosomal DNA should contain 3 linkers, i.e. 3 consecutive nucleosomes packing about 600 bps of DNA. The excluded volume of the nucleosomes, nucleosome interactions, and other DNA-bound proteins can make the fiber less flexible or prohibit certain conformation and may tend to increase the persistence length of the fiber.

Using this estimated lower bound estimate for the persistence length, the Kuhn length of the equivalent freely-jointed chain was obtained to be 6 nucleosomes, or ~1200 bp. A simulated chain of 4000 monomers corresponds to 4.8 Mb of packed DNA. The size of each monomer was chosen such that its volume is equal to (or slightly above) that of 6 nucleosomes ($V=6\times 600$ nm$^3$); thus the radius of the spherical monomer is R=10 nm. The diameter of each globules shown above are about 200 nm.

Lattice Analogues

As noted earlier, a fractal globule is, in many respects, analogous in structure to a finite iteration of a Peano curve. The equilibrium globule is analogous to a Hamiltonian path: a path traversing a lattice which need not satisfy the constraint of self-similarity. See, FIG. 51.

EXPERIMENTAL

Example I

Preparation of Standard Buffers

A. Tris-EDTA (TE) (1×)
  pH=8.0
    –10 mM Tris-HCl; pH=8.0
    –1 mM EDTA: pH=8.0
  Prepared from 10× stock solution and autoclaved water.
B. 10×NEB2 Restriction Buffer (10×)
  pH=8.0

| Final Concentration | Preparation Aliquot |
|---|---|
| 100 mM Tris-HCl | 5 ml 1M Tris-HCl; pH = 8.0 |
| 500 mM NaCl | 5 ml 5M NaCl |
| 100 mM MgCl$_2$ | 5 ml 1M MgCl$_2$ |
| 10 mM Dithiothreitol | 0.5 ml 1M DTT |
| Autoclaved water | 34.5 ml (pH = 7.9 @ 25° C.) |

Total preparation volume=50 ml. Storage of 10 ml and 1 ml aliquots at –20° C.

C. Phenol:Chloroform (1:1 Ratio)
  200 ml phenol, pH=8.0
  Add a little of upper phase from phenol bottle.
  200 ml chloroform
  Mix and let set overnight.
D. Lysis Buffer (1×)

| Final Concentration | Preparation Aliquot |
|---|---|
| 10 mM Tris-HCl, pH = 8.0 | 0.5 ml 1M Tris-HCl, pH = 8.0 |
| 10 mM NaCl | 0.1 ml 5M NaCl |

| Final Concentration | Preparation Aliquot |
|---|---|
| 0.2% Ige cal CA630 (NP40) | 1 ml 10% NP40 |
| Autoclaved MQ | 48.4 ml |

Total preparation volume=50 ml. Store at 4° C.
E. T4 Polynucleotide Kinase Reaction Buffer (PKRB)
  Final Concentration
  70 mM Tris-HCl, pH=7.6
  10 mM MgCl$_2$
  5 mM Dithiothreitol
F. Spheroplasting Buffer I
  0.4 M sorbitol
  0.4 M KCl
  40 mM Sodium Phosphate buffer, pH=7.2.
  0.5 mM MgCl$_2$
  Store at 4° C. for up to 6 months.
G. Zymolyase 100-T solution
  20 mg/mL Zymolyase 100-T
  2% (w/v) glucose
  50 mM Tris, pH=7.5.
  Twenty mg/mL zymolyase 100-T will not go into solution. Make up zymolyase solution at least 1 hour prior to use. Before zymolyase is added to the cells be sure the solution is mixed well as a suspension. Store at 4° C. for up to 1 month.
H. MES wash buffer
  0.1 M MES
  1.2 M sorbitol
  1 mM EDTA, pH=8.0.
  0.5 mM MgCl$_2$
  Adjust pH to 6.4 with NaOH
  Store at 4° C. for up to 6 months.
I. T4 Polynucleotide Kinase Reaction Buffer (PKRB)
  Final Concentration
  70 mM Tris-HCl, pH=7.6
  10 mM MgCl$_2$
  5 mM Dithiothreitol
J. 10× Ligation buffer (50 ml)

| Final Concentration | Preparation Aliquot |
|---|---|
| 500 mM Tris-HCl pH 7.5 | 25 ml 1M Tris-HCl pH 7.5 |
| 100 mM MgCl2 | 5 ml 1M MgCl2 |
| 100 mM DTT | 5 ml 1M DTT |
| Autoclaved MQ | 15 ml |

Store 20 ml and 1 ml aliquots at –80° C.

Example II

Hi-C Nucleic Acid Linker Protocol, Part I: Human

I. Non-Compatible Linker Preparation
  A. Perform 2 phosphorylation reactions, one for each fragment:

```
HiC-4b-T-bio fragment:
GCTGCATGA/iBiodT/GTACTAG

HiC-4b-BOT fragment:
GCTCTAGTACATCATGC
```

1. Mix 15.3 µl of 400 µM primer with:
  a. 30 µl PKRB
  b. 30 µl 10 mM ATP
  c. 15 µl (10 U/ul) T4 Polynucleotide Kinase (PNK)
  d. 209.7 µl water 2. Split into 6×50 µl aliquots.
3. Incubate each aliquot at 37° C. for 30 minutes.
4. Inactivate PNK by incubating at 65° C. for 10 minutes.
5. Pool all reaction products of both fragments into one tube and mix.

B. Split pooled phosphorylated fragments into 4×150 µl aliquots.
C. Bring 1 liter water to boiling point.
D. Put aliquot tubes with phosphorylated fragments into water (~95° C.).
E. Cool to room temperature (i.e., for example, ~25° C.) for ~4 hours.
F. Mix 5 µl of 1:100 phosphorylated fragment and 5 µl of 1:10 linker
G. Perform gel electrophoresis and analyze for fragment-linker dimer formation.
H. Store @–20° C.

II. Genomic Crosslinking
A. Centrifuge between $7\times10^7$ to $1\times10^8$ cells at 1200 rpm for ~10 min.
B. Resuspend the cell pellet in 45 ml of fresh medium, mix by pipetting.
C. Add 1.25 ml of 37% formaldehyde to obtain 1% final concentration and pipet to mix to initiate crosslinking.
D. Incubate at room temperature (i.e., for example, ~25° C.) for ~10 min, with intermittent shaking.
E. Add 2.5 ml of 2.5 M glycine to stop crosslinking
F. Incubate at (i.e., for example, ~25° C.) for ~5 min and transfer to 0° C. (i.e., for example, ice bath) for ~15 additional minutes.
G. Centrifuge at 1500 rpm for ~10 min and remove the supernatant.
H. Optional storage of pellet: incubate crosslinked pellet on dry ice for ~20 min and then store at –80° C.

III. Genomic Digestion
A. Resuspend crosslinked pellet by adding 2 ml of cold Lysis buffer and 200 µl of Protease inhibitors (optimal activity if added just before use) at 0° C. (i.e., for example, ice bath).
B. Incubate on ice>15 min to maximize cell swelling.
C. Cell lysis I at 0° C. ((i.e., for example, ice bath) by homogenization (i.e., for example, a dounce homogenizer). Incubate for ~1 minute on ice after 10 strokes, then perform at least 10 subsequent strokes.
D. Transfer to 2 microcentrifuge tubes, spin at 5000 rpm at room temperature (i.e., for example, 25° C. for ~5 min
E. Wash each pellet with 1 ml cold 1×NEB2 buffer and centrifuge at 5000 rpm, room temperature (i.e., for example, 25° C.) for ~5 min to create a cell lysis pellet I.
F. Repeat steps C-E using remaining cell supernatant from step D to create a cell lysis pellet II.
G. Resuspend cell lysis pellet I and cell lysis pellet II individually in 500 µl of 1×NEB2 buffer and then pool both suspensions.
H. Distribute 50 µl aliquots of the pooled suspension among approximately 22 microcentrifuge tube, avoiding suspension sedimentation.
I. Add 312 µl of 1×NEB2 buffer to each tube
J. Add 38 µl of 1% sodium docecylsulfate (SDS) to each tube and mix well, avoiding the creation of air bubbles.
K. Incubate at 65° C. for ~10 min.
L. Add 44 µl of 10% Triton X-100 to each tube, mix well, avoiding air bubbles thereby quenching SDS activity.
M. Add 20 µl (~j 400 U) of a restriction enzyme (i.e., for example, HindIII) to each tube, mix well and incubate at 37° C. for ~12 hours (i.e., for example, overnight).

IV. End-Filling, Ligation and Reverse Crosslinking
A. Transfer tubes containing restriction enzymes to 0° C. (i.e., for example, an ice bath).
B. Add 1.5 µl of 10 mM dATP (33 µM end concentration) per tube.
C. Add 10 µl (50 U) Klenow per tube.
D. Incubate for at 37° C.~15 min.
E. Incubate tubes at 0° C. (i.e., for example directly in an ice bath).
F. Add 86 µl of 10% SDS to all tubes as quickly as possible and mix by pipetting.
G. Incubate at 65° C. for ~30 min to inactivate the enzymes.
H. Incubate tubes at 0° C. (i.e., for example directly in an ice bath).
I. Prepare ligation cocktail master mix (except ligase) on ice and add 7.61 ml of cocktail per 15 ml conical tube. Incubate tubes at 0° C. (i.e., for example directly in an ice bath).

| Ligation cocktail | Amount per Tube | Total Volume for 23 Tubes |
| --- | --- | --- |
| 10% Triton X-100 | 745 µl | 7135 µl |
| 10X NEB2 | 745 µl | 7135 µl |
| 10 mg/ml BSA (100X, NEB) | 80 µl | 840 µl |
| 100 mM ATP | 80 µl | 840 µl |
| water | 5960 µl | 137080 µl |

J. Transfer 500 µl digestion product from Step H to one 15 ml conical tube.
K. Add 4 µl non-compatible linker.
L. Add 10 µl of (1 U/µl) T4 ligase (Invitrogen) per tube.
M. Mix by inverting the tubes several times and spin the tubes shortly.
N. Incubate at 16° C. for ~4 hrs.
O. Add 50 µl of 10 mg/ml proteinase K per tube.
P. Mix by inverting the tubes several times and spin the tubes shortly.
Q. Incubate at 65° C. overnight.

V. Purification
A. Add 50 µl of 10 mg/ml proteinase K per tube and incubate at 65° C. for ~2 hr
B. Transfer reaction products into 10 clean 50 ml conical tubes by pooling contents of two 15 ml tubes into one 50 ml tube).
C. Add 20 ml of phenol per 50 ml tube, vortex for ~2 min and centrifuge at 3500 rpm for ~10 min.
D. Transfer supernatant to fresh 50 ml conical tubes. This is optimally performed by first using a 10 ml pipet, and then switching a 1 ml pipet to obtain DNA close to the interphase. The supernatant may appear a bit cloudy.
E. Add 20 ml of phenol:chloroform (1:1) per tube, vortex for ~1 min and centrifuge at 3500 rpm for ~10 min.
F. Remove the aqueous supernatant from the conical tubes and pool 1.5 supernatants into a single new 50 ml conical tube, thereby resulting in six (6) 50 ml tubes. In most cases, the supernatant and interface should both be clear.
G. Add TE buffer to a total volume of 50 ml (dilution might help to prevent DTT to precipitate).
H. Transfer each 50 ml pool to an 250 ml screw-cap centrifuge tube that is suitable for high-speed centrifugation.

I. Add 5 ml of 3M sodium acetate, pH 5.2 per tube, mix and add 125 ml 100% ice-cold ethanol per tube, mix gently.
J. Incubate at −80° C. for at least 60 min and/or overnight.
K. Centrifuge at 10,000×g for ~20 min at 4° C.
L. Discard the supernatant and air dry the pellet briefly.
M. Dissolve each pellet in 225 µl of 1×TE buffer, pH 8.0 and transfer to a 1.7 ml centrifuge tube.
N. Wash the tubes with 225 µl of 1×TE buffer, pH 8.0 and transfer to the same 1.7 ml centrifuge tube (if dissolving is difficult, put samples at 65° C. for 10 minutes).
O. Add 500 µl of phenol:chloroform (1:1) to each tube and vortex for ~1 min; then
   centrifuge at room temperature (i.e., for example, 25° C.) at 2460×g (i.e., for example 3500 rpm, or full speed using a benchtop centrifuge) for ~5 min.
P. Transfer the upper aqueous phases to new 1.7 ml centrifuge tubes
Q. Add 500 µl of phenol:chloroform (1:1), vortex for ~30 sec and centrifuge at 2460×g (i.e., for example, 3500 rpm or full speed using a benchtop centrifuge for ~5 min. Optionally, a single chloroform extraction may be performed to remove last traces of phenol.
R. If the interfaces are clear, go to precipitation step; otherwise perform another purification.
S. Transfer the upper phases into a new 1.7 ml centrifuge tube.
T. Add 1/10 volume of 3M NaAc, pH 5.2, vortex briefly.
U. Add 2.5 volume of 100% ice-cold ethanol, mix gently.
V. Incubate at −80° C. for at least 30 min.
W. Centrifuge at 4° C. at 18,000×g for ~20 min.
X. Wash the pellets in 1 ml of 70% ethanol and centrifuge at 4° C. at 18,000×g for ~15 min
Y. Repeat the ethanol wash 5 times until pellets are "soft" or less "salty".
Z. Dissolve all pellets in a total volume of 1 ml 1×TE buffer, pH 8.0
AA. Add 1 µl 10 mg/ml of DNase-free, RNase A and incubate at 37° C. for ~15 min
BB. Load 2 µl of 10× diluted library on 0.8% agarose/0.5×TBE gel, along with 1 Kb DNA ladder; quick run to check quality and quantity of the library.
CC. Store HiC library for up to 2 years at −20° C.

Example II

Hi-C Nucleic Acid Linker Protocol, Part I: Yeast

I. Non-Compatible Linker Preparation
  A. Perform 2 phosphorylation reactions, one for each fragment:

```
HiC-4b-T-bio:
GCTGCATGA/iBiodT/GTACTAG

HiC-4b-BOT:
GCTCTAGTACATCATGC
```

1. Mix 15.3 µl of 400 µM primer with:
    a. 30 µl PKRB
    b. 30 µl 10 mM ATP
    c. 15 µl (10 U/ul) T4 Polynucleotide Kinase (PNK)
    d. 209.7 µl water
  2. Split into 6×50 µl aliquots.
  3. Incubate each aliquot at 37° C. for 30 minutes.
  4. Inactivate PNK by incubating at 65° C. for 10 minutes.
  5. Pool all reaction products of both fragments into one tube and mix.
  B. Split pooled phosphorylated fragments into 4×150 µl aliquots.
  C. Bring 1 liter water to boiling point.
  D. Put aliquot tubes with phosphorylated fragments into water (~95° C.).
  E. Cool to room temperature (i.e., for example, ~25° C.) for ~4 hours.
  F. Mix 5 µl of 1:100 phosphorylated fragment and 5 µl of 1:10 linker
  G. Perform gel electrophoresis and analyze for fragment-linker dimer formation.
  H. Store @−20° C.
II. Genomic Crosslinking
  A. Obtain a 200 mL culture of *Saccharomyces cerevisiae* cells at $OD_{600}=1$.
  B. Centrifuge cells 10 minutes at 2500 rpm and remove supernatant promptly.
  C. Resuspend cells in 10 mL spheroplasting buffer and transfer to 15 mL tubes.
  D. Add 50 µL 20 mg/mL zymolyase 100-T solution and gently mix tube.
  E. Incubate in roller drum for 40 minutes at ~30° C.
  Efficiency of digestion of cell wall should be tested by cell lysis. This can be done by adding water to a small amount of cells on a glass slide while observing under a microscope. Digestion is complete when approximately 80% of cells burst open and exhibit hypotonic lysis within 1-2 minutes.
  F. Wash cells two times in 10 mL of MES wash buffer. Between each wash centrifuge cells for ~5 minutes at 3500 rpm.
  G. Dissolve in 10 mL MES wash buffer.
  H. Add formaldehyde to 1% (263 µL of 37% stock), mix thoroughly and incubate for ~10 minutes at room temperature.
  I. Add 0.5 mL 2.5 M glycine and incubate for ~5 minutes at room temperature.
  J. Cells can now be stored at −80° C. in 1 mL aliquots or can directly be digested.
III. Crosslinked Genome Digestion
  A. Add 50 µL of crosslinked cells to individual 1.7 mL microfuge tubes. Reactions should not be pooled. Typically 40 tubes, each containing 50 µL of cells yields the best results although amount of cells used can vary depending on need.
  B. Wash cells three times with 100 µL 1×NEB2 per tube.
  C. Between each wash, mix by pipetting up and down and centrifuge for ~3 minutes at 14,000 rpm.
  D. Resuspend thoroughly in 36.2 µL 1×NEB2 per tube.
  E. Add 3.8 µL of 1% SDS per tube and incubate for 10 minutes for ~65° C.
  F. Add 4.4 µL 10% Triton X-100 per tube. Mix well by pipetting up and down. Triton X-100 binds SDS and will thereby effectively remove SDS, which facilitates the subsequent restriction digestion.
  G. Add 60 Units of a restriction enzyme (i.e., for example) HindIII per tube, mix well, and incubate reactions overnight at ~37° C.
IV. End Filling, Ligation And Reverse Crosslinking
  A. Place tubes containing restriction enzyme at ~0° C. (i.e., for example, ice bath).
  B. Add 1.5 µl of 1 mM dATP (~33 µM end concentration) per tube.
  C. Add 1 µl (5 U) Klenow per tube.
  D. Incubate at ~37° C. for ~15 minutes.
  E. Place tubes at ~0° C. (i.e., for example, ice bath).

F. Add 8.6 µl of 10% SDS to all tubes as quickly as possible and mix by pipetting to inactivate the restriction enzyme
G. Incubate at ~65° C. for ~30 min.
H. Place tubes at ~0° C. (i.e., for example, ice bath).
I. Prepare ligation cocktail master mix and add 761 µl of cocktail to each tube.

| Ligation Cocktail | Aliquot per Tube |
|---|---|
| 10% Triton X-100 | 74.5 µl |
| 10X NEB2 | 74.5 µl |
| 10 mg/ml BSA (100X, NEB) | 8 µl |
| 100 mM ATP | 8 µl |
| Non-compatible linker | 0.4 µl |
| water | 593.6 µl |
| T4 DNA ligase (Invitrogen, 1 U/µl) | 2 µl |
| Total Volume | 761 µl |

J. Incubate for ~4 hours at ~16° C.
K. Add 5 µL 10 mg/mL proteinase K in TE buffer, pH 8.0 and incubate for ~12 hours (i.e., for example, overnight) at ~65° C. to reverse crosslinks.
V. Purification
  A. Add an additional 5 µL 10 mg/mL proteinase K in TE buffer, pH 8.0 and incubate at ~42° C. for ~2 hours.
  B. Combine a maximum of 10 reaction tubes in a single 50 mL tube to end up with 4 larger pooled reactions (assuming 40 reaction tubes).
  C. Add an equal volume of 1:1 phenol/chloroform to each of the ligation mixtures, vortex for ~30 seconds and centrifuge for ~5 minutes at 3500 rpm. Aqueous (upper) phase at this step in purification will appear cloudy.
  D. Promptly collect the aqueous (upper) phase.
  E. Repeat phenol/chloroform extraction and transfer aqueous phase to a 30 mL centrifuge tube. Aqueous phase at this step in the purification should be clear. If the aqueous phase is still cloudy repeat phenol/chloroform extraction until aqueous phase is clear.
  F. Precipitate DNA by adding 1/10 volume of 3 M NaAc, pH 5.2, vortex briefly.
  G. Add 2.5 volumes of 100% ethanol and mix gently. Incubate for ~15 minutes at -80° C. and centrifuge for ~20 minutes at 10,000 rpm at ~4° C.
  H. Remove supernatant and let pellets dry completely before resuspending each pellet in 100 µL TE buffer, pH 8.0. Pool all 4 samples to obtain a 400 µL DNA solution.
  I. Add an equal volume of 1:1 phenol/chloroform to pooled sample, vortex for ~30 seconds and centrifuge for ~5 minutes at ~14,000 rpm.
  J. Promptly collect the aqueous (upper) phase.
  K. Precipitate DNA by adding 1/10 volume of 3 M NaAc, pH 5.2, vortex briefly.
  L. Add 2.5 volumes of ice cold 100% ethanol and mix gently. Incubate for ~15 minutes at -80° C. and centrifuge for ~20 minutes at 10,000 rpm at ~4° C.
  M. Remove supernatant and wash with 70% ethanol. Centrifuge for ~5 minutes at ~14,000 rpm.
  N. Remove supernatant and let pellets dry completely before resuspending the pellet in 200 µL TE buffer. If less than 40 tubes are initially used in step 9 the final volume should be adjusted accordingly.
  O. Add 2 µL 10 mg/mL DNase free RNase A and incubate for ~15 minutes at 37° C.
  P. Store HiC library at least at -20° C.

Example III

Hi-C Nucleic Acid Linker And Nucleotide Ligation Protocol, Part II

This protocol is followed regardless of cell source (i.e., for example, human or yeast).
I DNA Shearing
  A. Use 0.5-10 µg of HiC DNA in a final volume of 280 µl low TE (10 mM Tris pH8.0, 0.1 mM EDTA) and shear (i.e., for example, by using a Covaris S2):
    1. For 200-300 bp size range use twelve (12) cycles

| Treatment No | Duty Cycle | Intensity | Cycles/Burst | Time |
|---|---|---|---|---|
| 1 | 20 | 10 | 200 | 30 |
| 2 | 5 | 10 | 200 | 5 |

2. For 400-500 bp size range use four (4) cycles

| Treatment No | Duty Cycle | Intensity | Cycles/Burst | Time |
|---|---|---|---|---|
| 1 | 5 | 5 | 200 | 30 |

II. End Repair DNA
  A. Repair the ends of the sheared DNA using a commercially available kit (i.e., for example, End-it DNA End-repair Kit, Epicentre Biotechnologies).

| Reagent | Volume (µl) |
|---|---|
| Sheared DNA | 280 |
| 10X End-Repair Buffer | 40 |
| 2.5 mM dNTP | 40 |
| 10 mM ATP | 40 |
| End Repair Enzyme Mix | 4 |

Incubate at room temperature for 45 minutes
  B. Purify the DNA using a MinElute column (Qiagen) and elute in 2×15 ul of low TE buffer.
III. Adding an 'A' Tail
  A. Mix together the following reagents:

| Reagents | Volume (µl) |
|---|---|
| End-Repaired DNA | 30 |
| 10X NEBuffer 2 | 5 |
| 1 mM dATP | 10 |
| Water | 2 |
| Klenow Fragment (3' to 5' exo-) | 3 |

B. Incubate at ~37° C. for ~30 mins.
  C. Denature DNA at ~65° C. for ~20 mins and cool at ~0° C. (i.e., for example, an ice bath).
  D Evaporate the volume to ~20 µl (i.e., for example, by using a SpeedVac) and run on 3% agarose gel overnight in 1×TAE.
  E. Stain the agarose gel with SYBR green.
  F. Excise a gel slice around ~200-300 bp.
  G. Purify the DNA from the agarose gel using a commercially available kit (i.e., for example, QIAquick Gel Extraction Kit (Qiagen)) according to the manufacturers instructions, except that DNA should be eluted in 100 µl EB buffer and made to a final volume of 300 µl using EB buffer.

IV. Paired End Adapter Ligation
  A. Bind sheared DNA to Streptavidin beads (i.e., for example, MyOne Streptavidin C1 beads, Invitrogen) using DNA-resistant tubes (i.e., for example, 2 ml DNA LoBind tubes, Eppendorf). Streptavidin beads will specifically bind to the biotin labeled internal adaptor in the HiC sheared DNA molecules. This will isolate them from the non-biotin products formed during the shearing process.
  B. Prepare the following buffers:
    1. Binding and Wash buffer—NO Tween (2×)

| Final Concentration | Aliquot Preparation | |
|---|---|---|
| 10 mM Tris-HCl, pH = 8.0 | 1M Tris-HCl, pH = 8.0, | 500 μl |
| 1 mM EDTA | 0.5M EDTA | 100 ul |
| 2M NaCl | 5M NaCl | 20 mls |
|  | Water | 29.4 mls |

Total preparation volume=50 mls
    2. Binding and Wash buffer—Tween (2×)

| Final Concentration | Aliquot Preparation | |
|---|---|---|
| 10 mM Tris-HCl, pH = 8.0 | 0.5M EDTA | 100 μl |
| 1 mM EDTA | 0.5M EDTA | 100 μl |
| 2M NaCl | 5M NaCl | 20 mls |
| 0.1% Tween | 0.1% Tween | 50 μl |
|  | Water | 29.4 mls |

Total preparation volume=50 mls
  C. Vortex the bottle of streptavidin beads and remove 60 μl into a DNA resistant tube.
  D. Wash beads with 400 μl 1× Tween wash buffer.
  E. Mix by rotation at room temperature for ~3 minutes.
  F. Hold the tube against a magnet and discard supernatant.
  G. Wash beads with 400 μl 1× Tween wash buffer.
  H. Mix by rotation at room temperature for 3 minutes.
  I. Hold the tube against a magnet and discard supernatant.
  J. Add 300 μl of 2×NO Tween wash buffer.
  K. To bind the DNA to the streptavidin beads, add 300 ul of resuspended beads to the 300 μl of DNA purified from the gel slices.
  L. Mix by rotation at room temperature for 15 minutes.
  M. Hold the tube against a magnet and discard supernatant.
  N. Resuspend beads in 400 μl 1×NO Tween wash buffer.
  O. Mix by rotation at room temperature for 1 minute.
  P. Hold the tube against a magnet and discard supernatant.
  Q. Resuspend beads in 100 μl 1× Ligase buffer and transfer beads to a new tube.
  R. Mix by rotation at room temperature for ~1 minute.
  S. Hold the tube against a magnet and discard supernatant.
  T. Resuspend beads in 50 μl 1× Ligase buffer.
V. Illumina Paired End Adapter Ligation
  A. Calculate the number of pmol of Paired End Adapters needed for ligation using the following assumptions:
    1. The original non-sheared Hi-C DNA comprised 8 kb circles.
    2. Need 2 adapters per circle (i.e., one pair).
    3. For sheared 8 kb samples into 200-300 bp fragments, assume:
      a. A 16 fold reduction for two adaptors
      b. A 32 fold reduction for a single adaptor.
      c. Use 60 fold excess of adapters.
      d. For example:
Total Sheared DNA (μg)=X
DNA purified from excised Gel slice (μg)=Y
DNA Available for ligation=Y/16
pmol for 1 ug of 200-300 bp sheared DNA (assume 250 bp) 6.1
pmol of sheared DNA available for ligation (bound to beads) 6.1*(Y/16)
pmol of Paired End Adapter for ligation (60 fold excess) 6.1*(Y/16)*60
  B. Prepare the following ligation reaction:

| Bead bound HiC DNA | 50 ul |
|---|---|
| Paired End adapters | Calculated in accordance with step A |
| 10 mM ATP | 5 ul |
| T4 DNA Ligase (Ambion) | 4 ul |

C. Incubate the ligation at room temperature (i.e., for example, 25° C.) for ~2 hrs.
  D. Resuspend beads in 400 μl 1× Tween wash buffer.
  E. Incubate at 37° C. for 1 min to remove non-ligated Paired End Adapters
  F. Hold the tube against a magnet and discard supernatant.
  G. Resuspend beads in 400 μl 1× Tween wash buffer.
  H. Mix by rotation at room temperature for 1 min.
  I. Transfer to a new DNA-resistant tube. Hold the tube against a magnet and discard supernatant
  J. Resuspend beads in 200 μl 1×NO Tween wash buffer.
  K. Mix by rotation at room temperature for 1 min.
  L. Transfer to a new DNA resistant tube. Hold the tube against a magnet and discard supernatant.
  M. Resuspend beads in 200 μl 1×NEB2.
  N. Mix by rotation at room temperature for 1 min.
  O. Transfer to a new DNA resistant tube. Hold the tube against a magnet and discard supernatant.
  P. Resuspend beads in 50 μl 1×NEB2.
  Q. Mix by rotation at room temperature (i.e., for example, 25° C.) for 1 min.
  R. Transfer to a new DNA resistant tube. Hold the tube against a magnet and discard supernatant.
  S. Resuspend beads in 50 μl 1×NEB 2.
VI. Trial PCR using Illumina's paired end primers PE1.0 and PE2.0
  A. Trial PCR to determine the optimal number of PCR cycles for the enrichment of the HiC—Paired End Adapter ligated molecules.
    1. Use 3 μl of bead bound library in PCR

| SAMPLE | HiC DNA | control | control |
|---|---|---|---|
| library vol | 3.0 | 0.0 | 0.0 |
| primers | 0.6 | 0.0 | 0.6 |
|  | PE1.0/PE2.0 | PE1.0/PE2.0 | PE1.0/PE2.0 |
| 2XPhusion | 25.0 | 25.0 | 25.0 |
| dH2O | 21.4 | 25.0 | 24.4 |
| final volume | 50.0 | 50.0 | 50.0 |

B. Set up PCR reactions and split in 4. Cycle for 9/12/15/18 cycles PCR in 384 well plates

| 98 C. | 30 secs | |
|---|---|---|
| 98 C. | 10 secs | |
| 65 C. | 30 secs | CYCLE 9/12/15/18 |
| 72 C. | 30 secs | |
| 72 C. | 7 mins | |
| 4 C. | indefinite | |

C. Add 2.5 µl loading dye and run 10 µl of PCR reaction on a 10% polyacrylamide gel.
D. Stain the gel using Sybr Green.
E. Determine the optimal PCR cycle number for large scale PCR enrichment of the DNA.

VII. Large Scale PCR Enrichment

A. Use 42 µl of library in a 700 µl PCR reaction.

| SAMPLE | HiC DNA | control | control |
|---|---|---|---|
| library vol | 42.0 | 0.0 | 0.0 |
| primers | 16.8 PE1.0/PE2.0 | 0.0 PE1.0/PE2.0 | 0.6 PE1.0/PE2.0 |
| 2XPhusion | 350.0 | 25.0 | 25.0 |
| dH2O | 291.2 | 25.0 | 24.4 |
| final volume | 700.0 | 50.0 | 50.0 |

B. Set up PCR into 14 wells of 96 well plate. Use the number of PCR cycles determined by the trial PCR.

| | |
|---|---|
| 98 C. | 30 secs |
| 98 C. | 10 secs |
| 65 C. | 30 secs |
| 72 C. | 30 secs |
| 72 C. | 7 mins |
| 4 C. | indefinite |

C. Combine the PCR reactions from the 14 wells.
D. Reclaim the streptavidin beads by holding the tube against a magnet.
E. Transfer the 700 µl of PCR reaction to a new tube.
F. Remove 7 µl of PCR product (from 700 µl) and check it on a 4-20% polyacrylamide gel.
G. Purify the PCR product using AmPure beads (Agencourt).
H Add 1.8× the volume of AmPure beads.
I Pipet the samples up and down 10 times
J Separate the beads with PCR product attached from the PCR primers by holding the tube against a magnet for a few minutes.
K Remove the supernatant and wash the beads twice using 1 l of 70% ethanol while the tube remains on the magnet
L Airdry the beads.
M Elute the DNA from the beads by resuspending the beads in 50 µl of low TE buffer,
N. Hold the tube against a magnet and transfer the DNA solution to a new tube.
O. Remove 0.5 µl of the DNA solution to check against the original PCR product on a 4-20% polyacrylamide gel.
P. Evaporate the sample ~30 µl (i.e., for example, by using a SpeedVac).
Q. Measure the DNA concentration (i.e., for example, by using Qubit, Invitrogen).
R. Sequence samples in a high throughput sequencer (i.e., for example, Solexa, Illumina).

Example IV

Hi-C Nucleotide Ligation Protocol: Part 1: Human

A. Crosslinking & Fixation
1. Centrifuge between 7×10$^7$ and 1×10$^8$ cells at 1200 rpm for ~10 min.
2. Resuspend the cell pellet in 45 ml of fresh medium, mix by pipetting.
3. Add 1.25 ml of 37% formaldehyde to obtain 1% final concentration and pipet to mix.
4. Incubate at room temperature (~25° C.) for ~10 min, shaking occasionally.
5. Add 2.5 ml of 2.5M glycine to stop crosslinking
6. Incubate at room temperature (~25° C.) for ~5 min and then at 0° C. (i.e., for example, using an ice bath) for ~15 min
7. Centrifuge at 1500 rpm for ~10 min and remove the supernatant
8. Optional: Incubate pellet on dry ice for ~20 min and then store at −80° C.

II. Fragmentation & Digestion
8. Add 2 ml of cold Lysis buffer and 200 µl of Protease inhibitors (add PI just before use!) to the pellet and resuspend it well on ice
9. Incubate at 0° C. (i.e., for example, using an ice bath) for at least 15 min to let the cells swell
10. Lyse the cells at 0° C. (i.e., for example, using an ice bath) using the dounce homogenizer (>20 times up and down, incubate 1 minute at 0° C. (i.e., for example, using an ice bath) after 10 times, then continue)
11. Transfer to 2 microcentrifuge tubes, spin at 5000 rpm at room temperature (~25° C.) for ~5 min
12. Wash each pellet with 1 ml cold 1×NEB2 buffer and spin down at 5000 rpm, room temperature (~25° C.) for ~5 min
13. Repeat Step 12 once
14. Resuspend each pellet is 500 µl of 1×NEB2 buffer and pool both suspensions.
15. Distribute 50 µl of the suspension to each microcentrifuge tube (~22 tubes), avoid sedimentation of the suspension.
16. Add 312 µl of 1×NEB2 buffer per tube
17. Add 38 µl of 1% SDS per tube and mix well, avoiding air bubbles
18. Incubate at 65° C. for ~10 min.
19. Add 44 µl of 10% Triton X-100 to each tube, mix well, avoiding air bubbles (to quench SDS)
20. Add 20 µl of HindIII (400 U) per tube, mix well and incubate at 37° C. for ~12 hours (i.e., for example, overnight)

III. Filling in the Ends, Blunt-End Ligation and Reverse Crosslink
21. Place tubes at 0° C. (i.e., for example, using an ice bath).
22. Add per tube: 1.5 µl of 10 mM dATP
   1.5 µl of 10 mM dGTP
   1.5 µl of 10 mM dCTP
   15 µl of 1 mM biotinylated dUTP
23. Add 10 µl (50 U) Klenow per tube.
24. Incubate for at 37° C. for ~45 min.
25. Put tubes directly at 0° C. (i.e., for example, using an ice bath)
26. Add 86 µl of 10% SDS to all tubes as quickly as possible and mix by pipetting.
27. Incubate at 65° C. for ~30 min to inactivate the enzymes.
28. Place tubes at 0° C. (i.e., for example, using an ice bath).
29. Prepare ligation cocktail master mix (except ligase) at 0° C. (i.e., for example, using an ice bath) and add 7.61 ml of cocktail per 15 ml conical tube. Keep tubes at 0° C. (i.e., for example, using an ice bath)

| Ligation cocktail | per reaction | 23 reactions |
|---|---|---|
| 10% Triton X-100 | 745 µl | 17135 µl |
| 10X ligation buffer | 745 µl | 17135 µl |

-continued

| Ligation cocktail | per reaction | 23 reactions |
|---|---|---|
| 10 mg/ml BSA (100X, NEB) | 80 µl | 1840 µl |
| 100 mM ATP | 80 µl | 1840 µl |
| water | 5960 µl | 137080 µl |

30. Transfer 500 ul digestion product from Step 28 to one 15 ml conical tube.
31. Add 50 µl of (1 U/ul) T4 ligase (Invitrogen) per tube.
32. Mix by inverting the tubes several times and centrifuge the tubes briefly.
33. Incubate at 16° C. for ~4 hrs
34. Add 50 µl of 10 mg/ml proteinase K per tube
35. Mix by inverting the tubes several times and centrifuge the tubes briefly.
36. Incubate at 65° C. for ~12 hours (i.e., for example, overnight).

IV. Purification

37. Add 50 µl of 10 mg/ml proteinase K per tube and incubate at 65° C. for ~2 hr
38. Transfer reaction products into 10 clean 50 ml conical tubes (pool contents of 2 15 ml tubes into 1 50 ml tube).
39. Add 20 ml of phenol per 50 ml tube, vortex for ~2 min and then centrifuge at 3500 rpm for ~10 min
40. Transfer supernatant to fresh 50 ml conical tubes (First with 10 ml pipet, next with 1 ml pipet tip, most of the DNA is close to the interphase) (supernatant is a bit cloudy)
41. Add 20 ml of phenol:chloroform (1:1) per tube, vortex for ~1 min and centrifuge at 3500 rpm for ~10 min
42. Take the aqueous phase from the conical tubes. Pool 1.5 supernatants into one of each new 50 ml conical tube (6 tubes in total) (supernatant and interfase should both be clear).
43. Add TE buffer to a total volume of 50 ml (dilution might help to prevent DTT to precipitate).
44. Transfer each 50 ml pool to an 250 ml centrifuge tube (i.e., for example, a screw-cap) that is suitable for high-speed centrifugation.
45. Add 5 ml of 3M sodium acetate, pH 5.2 per tube, mix and add 125 ml 100% ice-cold ethanol per tube, mix gently.
46. Incubate at –80° C for at least 60 min or, alternatively for ~12 hours (i.e., for example, overnight)
47. Centrifuge at 10,000×g for ~20 min at 4° C.
48. Discard the supernatant and air dry the pellet briefly.
49. Dissolve each pellet in 225 µl of 1×TE buffer, pH 8.0 and transfer to a 1.7 ml centrifuge tube
50. Wash each tube with 225 µl of 1×TE buffer, pH 8.0 and transfer to the same 1.7 ml centrifuge tube (if dissolving is difficult, incubate samples at 65° C. for ~10 minutes).
51. Add 500 µl of phenol:chloroform (1:1) to each tube and vortex for ~1 min; then centrifuge at room temperature (i.e., for example, 25° C. at 2460×g (~3500 rpm) or full speed using a benchtop centrifuge for ~5 min
52. Transfer the upper aqueous phases to new 1.7 ml centrifuge tube
53. Add 500 µl of phenol:chloroform (1:1), vortex for ~30 sec and centrifuge at 2460×g (~3500 rpm) or full speed using a benchtop centrifuge for ~5 min. Optionally, repeat using chloroform only to remove last traces of phenol.
54. If the interfaces are clear, go to Step 55; otherwise repeat Step 53.
55. Transfer the upper phases into a new 1.7 ml centrifuge tube
56. Add 1/10 volume of 3M NaAc, pH 5.2, vortex briefly
57. Add 2.5 volume of 100% ice-cold ethanol, mix gently
58. Incubate at –80 C at least 30 min
59. Centrifuge at 4° C. at 18,000×g for ~20 min
60. Wash the pellets in 1 ml of 70% ethanol and centrifuge at 4° C. at 18,000×g for ~15 min
61. Repeat the ethanol wash 5 times until pellets are "soft" or less "salty".
62. Dissolve all pellets in a total volume of 1 ml 1×TE buffer, pH 8.0
63. Add 1 µl 10 mg/ml of DNase-free, RNase A and incubate at 37° C. for ~15 min
64. Load 2 µl of 10× diluted library on 0.8% agarose/0.5× TBE gel, along with 1 Kb DNA ladder; quick run to check quality and quantity of the library.
65. Store this HiC library up to 2 years at –20° C.

Example V

Crosslinking of Cells

Human cell line GM06990, an EBV-transformed lymphoblastoid cell line (Coriell, Camden, N.J.), was cultured in RPMI1640, 15% fetal calf serum, 1% penicillin-streptomycin, and 2 mM L-glutamine. Human erythroleukemia cell line K562 (ATCC, Manassas, Va.) was cultured in DMEM, 10% fetal calf serum, 1% penicillinstreptomycin, and 2 mM L-glutamine. One hundred million cells were spun down and resuspended in 45 ml fresh medium. Cells were fixed by adding 1.25 ml 37% formaldehyde and incubating for 10 minutes at room temperature (RT). The reaction was stopped by adding 2.5 ml 2.5 M glycine. The cell suspension was incubated for 5 minutes at RT, followed by 15 minutes on ice. The crosslinked cell suspension was split into 4 equal parts and centrifuged at 1500 rpm for 10 minutes. The supernatant was discarded and the cell pellets were stored at –80° C.

Example VI

Cell Lysis and Chromatin Digestion

For cell lysis, 550 µl lysis buffer (500 µl 10 mM Tris-HCl pH8.0, 10 mM NaCl, 0.2% Ige cal CA630; 50 µl protease inhibitors (Sigma, St. Louis, Mo.) were added to one batch of cells (~25 million cells). Cells were incubated on ice for at least 15 minutes. Next, cells were lysed with a Dounce homogenizer by moving the pestle A up and down 10 times, incubating on ice for one minute followed by 10 more strokes with the pestle. The suspension was spun down for 5 minutes at 5000 rpm at RT. The supernatant was discarded and the pellet was washed twice with 500 µl icecold 1×NEBuffer 2 (NEB, Ipswich, Mass.). The pellet was then resuspended in 1×NEBuffer 2 in a total volume of 250 µl and split into five 50 µl aliquots. Next, 312 µl 1×NEBuffer 2 was added per tube. To remove the proteins that were not directly crosslinked to the DNA, 38 µl 1% SDS was added per tube and the mixture was resuspended and incubated at 65° C. for 10 minutes exactly. Tubes were put on ice and 44 µl 10% Triton X-100 was added and mixed carefully avoiding bubbles to quench the SDS. Chromatin was subsequently digested overnight at 37° C. by adding 400 Units HindIII (NEB)

Example VII

Marking of DNA Ends and Blunt-End Ligation

Five tubes with digested chromatin were put on ice and tube 1 was kept separate and served as a 3C control. To fill in and mark the DNA ends, 1.5 µl 10 mM dATP, 1.5 µl 10 mM dGTP, 1.5 µl 10 mM dTTP, 37.5 µl 0.4 mM biotin-14-dCTP (Invitrogen, Carlsbad, Calif.) and 10 µl 5 U/µl Klenow (NEB) were added to tubes 2-5. The mixtures were incubated at 37° C. for 45 minutes and subsequently placed on ice. Enzymes were inactivated by adding 86 µl 10% SDS to tubes 1-5 and incubating all tubes at 65° C. for 30 minutes. Tubes were placed on ice immediately. Five 15 ml tubes were prepared, each containing 7.61 ml ligation mix (745 µl 10% Triton X-100, 745 µl 10× ligation buffer (500 mM Tris-HCl pH7.5, 100 mM MgCl2, 100 mM DTT), 80 µl 10 mg/ml BSA, 80 µl 100 mM ATP and 5.96 ml water). Each digested chromatin mixture was transferred to a corresponding 15 ml tube. For normal 3C ligation 10 µl 1 U/µl T4 DNA ligase (Invitrogen) was added to tube 1. For blunt-end ligation 50 µl 1 U/µl T4 DNA ligase was added to tubes 2-5. All 5 tubes were incubated at 16° C. for 4 hours.

Example VIII

DNA Purification

To reverse crosslinks and to degrade protein, 50 µl 10 mg/ml proteinase K was added per tube and the tubes were incubated overnight at 65° C. The next day an additional 50 µl 10 mg/ml proteinase K was added per tube and the incubation was continued at 65° C. for another 2 hours. Reaction mixtures were cooled to RT and transferred to five 50 ml conical tubes. The DNA was extracted by adding 10 ml phenol pH8.0, vortexing for 2 minutes and spinning for 10 minutes at 3,500 rpm. The supernatants were transferred to five new 50 ml conical tubes. Another DNA extraction was performed with 10 ml phenol pH8.0:chloroform (1:1). After vortexing and centrifugation for 10 minutes at 3,500 rpm, the supernatants were transferred to five 35 ml centrifugation tubes. The volume was brought to 10 ml per tube with 10 mM Tris pH8.0, 1 mM EDTA (1×TE). To precipitate the DNA, 1 ml 3M Na-acetate was added per tube and mixed well before adding 25 ml ice-cold 100% ethanol. Tubes were inverted several times to properly mix the contents and were incubated at −80° C. for at least one hour. Next, the tubes were spun at 4° C. for 20 minutes at 10,000×g. The supernatant was discarded and each DNA pellet was dissolved in 450 µl 1×TE and transferred to a 1.7 ml centrifuge tube. The DNA was extracted twice by adding 500 µl phenol pH8.0: chloroform (1:1), vortexing for 30 seconds and spinning at 14,000 rpm for 5 minutes at RT. After the second extraction, the supernatants (each ~400 µl) were transferred to five new 1.7 ml tubes and 40 µl 3M Na-acetate was added per tube and mixed. Next, 1 ml 100% ethanol per tube was added. After inverting the tubes several times, the tubes were incubated at −80° C. for at least 30 minutes. Tubes were spun at 18,000×g for 20 minutes at 4° C. The supernatant was discarded and the pellets were washed once with 500 µl 70% ethanol. After centrifuging at 14,000 rpm for 5 minutes, the supernatant was discarded and the pellets were air-dried briefly prior to resuspending in 25 µl 1×TE. To degrade any purified RNA, 1 µl 1 mg/ml RNAse A was added per tube and incubated at 37° C. for 15 minutes. The Hi-C contents of tubes 2-5 were pooled and tube 1 was kept separate as the 3C control.

Example IX

Quality Control HiC Libraries

Figure 26:
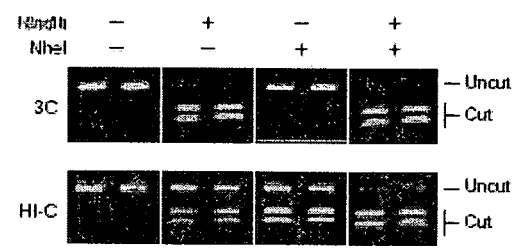
FIG. 26 presents exemplary data showing a polymerase chain reaction (PCR) digest control. Hi-C ligation products can be distinguished from those produced in conventional 3C by PCR amplification identifying a ligation junction formed by two nearby fragments followed by digestion of the ligation site. Hi-C junctions are cut by NheI, not HindIII; the reverse is true for 3C junctions. 70% of Hi-C amplicons were cut by NheI confirming efficient marking of ligation junction. Two replicates were performed to ensure reliable quantification.

Both 3C and Hi-C libraries were checked for quality and quantified by running an aliquot on a 0.8% agarose gel. To confirm that the ligation process worked as intended, we used the fact that successful fill-in and ligation of HindIII sites (AAGCTT) should create sites for the restriction enzyme NheI (GCTAGC). We used PCR to amplify a ligation product formed from two nearby restriction fragments and determined that 70% of amplicons were cut only by NheI. See, FIG. 26.

Sequences of the primers used for checking libraries are:

```
HindIII-1
                                (SEQ ID NO: 1)
GTTCATCTTGCTGCCAGAAATGCCGAGCCTG HindIII-2
                                (SEQ ID NO: 2)
ATCCCAGCTGTCTGTAGCTTTAGAAAGTGGG NcoI-1
                                (SEQ ID NO: 3)
ACCTGTTGTTTAATGAAGGGGCTCAGAAGC NcoI-2
                                (SEQ ID NO: 4)
GTTTGCAGTGTGCTGTGCAGCATGTGTGTA
```

Example X

Removal of Biotin from Unligated Ends

Biotin-14-dCTP at non-ligated DNA ends was removed with the exonuclease activity of T4 DNA polymerase. To this end 5 µg of Hi-C library was added to 1 µl 10 mg/ml BSA, 10 µl 10×NEBuffer 2, 1 µl 10 mM dATP, 1 µl 10 mM dGTP and 5 Units T4 DNA polymerase (NEB) in a total volume of 100 µl and incubated at 12° C. for 2 hours. If possible, multiple 5 µg reactions were performed. Reactions were stopped by adding 2 µl 0.5 M EDTA pH8.0. DNA was subsequently purified with one phenol pH8.0:chloroform (1:1) extraction followed by ethanol precipitation. DNA pellets were resuspended and pooled in a total of 100 µl water.

Example XI

Shearing and Size Selection

The DNA was sheared to a size of 300-500 basepairs with a Covaris S2 instrument (Covaris, Woburn, Mass.), Duty cycle 5, Intensity 5, Cycles/burst 200, time 60 secs for 4 cycles. The DNA ends were repaired by adding 14 µl 10× ligation buffer (NEB), 14 µl 2.5 mM dNTP mix, 5 µl T4 DNA polymerase (NEB), 5 µl T4 polynucleotide kinase (NEB), 1 µl Klenow DNA polymerase (NEB) and 1 µl water and was incubated at 20° C. for 30 minutes followed by purification of the DNA with a Qiagen MinElute column (Qiagen, Valencia, Calif.). The DNA was eluted with 2×15 µl 10 mM Tris pH8.0, 0.1 mM EDTA. Next, an 'A' was added to the 3' ends of the end repaired DNA by addition of 5 µl 10× NEBuffer2, 10 µl 1 mM dATP, 2 µl water and 3 µl Klenow (exo-) (NEB). The reaction was incubated at 37° C. for 30 minutes followed by 65° C. for 20 minutes to inactivate Klenow (exo-). The reactions were cooled on ice and the volume was reduced to 20 µl with a speedvac. DNA was electrophoresed on a 1.5% agarose gel in 1×TAE for 3.5 hours at 80 V. The gel was stained with SYBR green (Lonza Walkersville, Basel, Switzerland), visualized on a Dark-Reader (Clare Chemical, Dolores, Colo.) and DNA between 300 and 500 base pairs was excised and purified with a gel extraction kit (Qiagen). The gel slices were solubilized with three volumes of Buffer QG (Qiagen) at RT and the DNA purified with QIAquick spin columns (Qiagen). The DNA was eluted twice with 50 μl 10 mM Tris pH 8.0, 0.1 mM EDTA and the final volume was made up to 300 μl with 10 mM Tris pH 8.0, 0.1 mM EDTA. The DNA concentration was measured with the Quant-iT assay (Invitrogen).

Example XII

Biotin Pull-Down and Paired End Sequencing

All steps were performed in DNA LoBind tubes (Eppendorf, Westbury, N.Y.).

The biotin tagged Hi-C DNA was bound to Dynabeads MyOne Streptavin C1 Beads (Invitrogen) as follows. Sixty μl of resuspended Streptavidin beads were washed twice with 400 μl Tween Wash Buffer (TWB) (5 mM Tris-HCl pH8.0, 0.5 mM EDTA, 1 M NaCl, 0.05% Tween) by incubating for 3 minutes at RT with rotation. After this and for all subsequent incubations or washes of Streptavidin beads, the beads were reclaimed by holding against a magnetic particle concentrator (Invitrogen) for 1 minute and the supernatant was removed. These reclaimed beads were then resuspended in 300 μl 2× Binding Buffer (BB) (10 mM Tris-HCl pH8.0, 1 mM EDTA, 2 M NaCl) and combined with 300 μl Hi-C DNA. The mixture was incubated at RT for 15 minutes with rotation. The supernatant was removed and the DNA bound Streptavidin beads were resuspended in 400 μl 1×BB and transferred to a new tube. The beads were then resuspended in 100 μl 1× ligation buffer, transferred to a new tube before a final resuspension in 50 μl 1× ligation buffer. Six picomoles of Illumina Paired End adapters (Illumina, San Diego, Calif.) per μg of Hi-C DNA (measured after Qiagen gel purification) were ligated to the Hi-C DNA for 2 hours at RT in the presence of, 1 mM ATP and 20 U T4 DNA Ligase (Ambion, Austin, Tex.). The ligated Hi-C DNA was isolated by holding against the magnet and was washed with 400 μl of 1×TWB to remove non-ligated Paired End adapters. The beads were resuspended in a further 400 μl 1×TWB and the mixture was transferred to a new tube and the Streptavidin beads were recovered. This wash step was repeated with 200 μl 1×BB, then 200 μl 1×NEBuffer 2 and finally 50 μl 1×NEBuffer 2. The beads were resuspended in 50 μl 1×NEBuffer 2. Next, test PCR reactions were performed to determine the optimal PCR cycles needed to generate enough library for sequencing. Four trial PCR reactions, each containing 0.6 μl Streptavidin bead bound Hi-C library and Illumina PE1.0 and PE2.0 PCR primers (1.5 pmol each) in 10 μl 1× Phusion High Fidelity master mix with HF buffer (NEB), were set up to determine the number of cycles necessary to generate enough PCR product for sequencing. The temperature profile was 30 s at 98° C. followed by 9, 12, 15 or 18 cycles of 10 s at 98° C., 30 s at 65° C., 30 s at 72° C. and a final 7-minute extension at 72° C. The PCR reactions were run on a 5% polyacrylamide gel, stained with Sybr Green and the optimal cycle number was determined. A large-scale PCR was then set-up with the remainder of the Streptavidin bead bound Hi-C library with the number of PCR cycles determined by the trial PCR. 1% of the large scale PCR product was kept to run on a gel. The PCR product was purified by mixing with 1.8× volume Ampure beads (Beckman Coulter, Fullerton, Calif.). The mix was held against a magnet to separate the PCR product bound to the Ampure beads and the supernatant was discarded. The Hi-C library bound Ampure beads were washed twice with 1 ml 70% ethanol while the tube remained against the magnet. After air-drying the beads, the DNA was eluted by resuspending the beads in 50 μl of 10 mM Tris pH8.0, 0.1 mM EDTA. The tube was held against a magnet and the supernatant containing the purified PCR products was transferred to a new tube. Next, 1% of the Ampure bead purified PCR product was compared against the 1% aliquot of original PCR product on a 5% polyacrylamide gel. Finally, the Hi-C library was sequenced with Illumina paired end sequencing.

Example XIII

Chromatin Immunoprecipitation

ChIP experiments were carried out as described previously. Bernstein et al., *Cell* 120:169 (2005); and Mikkelsen et al., *Nature* 448:553 (2007). Briefly, chromatin from fixed cells was fragmented to a size range of 200-700 bases. Solubilized chromatin was immunoprecipitated with antibody against H3K27me3 (Upstate) or H3K36me3 (Abcam, Cambridge, Mass.). Antibody—chromatin complexes were pulled down with protein A-sepharose, washed and then eluted. After cross-link reversal and proteinase K treatment, immunoprecipitated DNA was extracted with phenol-chloroform, ethanol precipitated, and treated with RNase. ChIP DNA was quantified with PicoGreen.

Example IVX

Mapping of DNAseI Sensitivity

Cell lines (GM06990, Coriell and K562, ATCC) were cultured in humidified incubators at 37° C. in the presence of 5% CO2 according to the protocol provided by the source. Isolation of nuclei, DNaseI treatment, purification, and fractionation of small (<500 bp) DNaseI double-cleaved fragments was performed, as described. Sabo et al., *Nat Methods* 3:511 (2006). Endligation of sequencing adapters (Illumina) and cycle sequencing (to 27 bp) were performed, as described. Hesselberth et al., *Nat Methods* 6:283 (2009). 27 bp sequence reads were aligned to the human genome (NCBI build 37, UCSC HG18) with the Eland aligner (Illumina) (allowing 2 mismatches), and only reads mapping to unique genomic positions were utilized in downstream analyses. The density of DNaseI cleavages in a 150 bp (i.e., ~nucleosomesize) sliding window (step 20 bp, computed 5' to 3' across each chromosome individually) was computed for use in correlation analyses.

Example XV

Expression Analysis

Total RNA was extracted with QIAzol reagent following the miRNeasy kit's procedure (Qiagen), and sample quality was tested on a 2100 Bioanalyzer (Agilent, Palo Alto, Calif.). For oligonucleotide microarray hybridization, 1.5 μg of RNA were labeled, fragmented and hybridized to an Affymetrix Human Genome U133 plus 2.0 Array. After scanning, the expression value for each gene was calculated with RMA (Robust Multi-Array) normalization. The average intensity difference values were normalized across the sample set. Probe sets that were absent in all samples according to Affymetrix flags were removed.

Example XIV

DNA FISH

3D DNA FISH was performed essentially as described. Croft et al., *J Cell Biol* 145: 1119 (1999). BACs (Table S1) were obtained from the BACPAC Resource Center at Children's Hospital Oakland Research Institute in Oakland, Calif. See, Table 2.

TABLE 2

BAC clones used in 3D-FISH

| BAC name | Alias | Chromosome | Start position | End position |
|---|---|---|---|---|
| RP11-68M15 | L1 | Chr14 | 22546692 | 22722266 |
| RP11-91J1 | L2 | Chr14 | 45258185 | 45462464 |
| RP11-79B13 | L3 | Chr14 | 67744258 | 67904880 |
| RP11-88N20 | L4 | Chr14 | 86622674 | 86772926 |
| RP11-22M5 | L5 | Chr22 | 20569761 | 20724994 |
| RP11-79G21 | L6 | Chr22 | 26499393 | 26657386 |
| RP11-49M22 | L7 | Chr22 | 43469285 | 43637241 |
| RP11-66M5 | L8 | Chr22 | 46658148 | 46820598 |

About 100 ng of nick translated probes (labeled with DIG, DNP or biotin) and 10 ug of Cot-1 DNA were used in each hybridization. Image stacks (Z sections spaced 0.25 Km apart) were captured on an Olympus IX71 microscope (Olympus, Center Valley, Pa.) with a 100x/1.40 UPLS Apo objective and subsequently deconvolved with Deltavision SoftWorx software (Applied Precision, Issaquah, Wash.). 3D distance measurements were performed with the MeasurementPro module in Imaris (Bitplane, Saint Paul, Minn.). Specifically, measurements were taken from and to the perceived centers of each FISH spot. Example images of collapsed stacks were processed in Photoshop CS3 (Adobe, San Jose, Calif.).

Example XV

Read Alignment and Heatmap Generation

Figure 27:
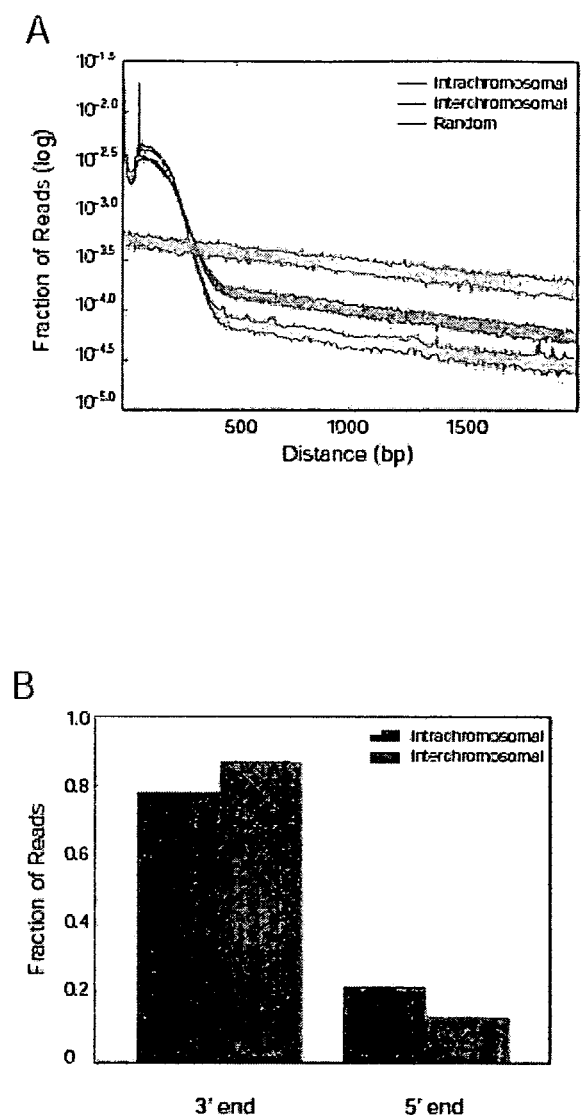
FIG. 27 presents exemplary data showing that Hi-C reads align near HindIII restriction sites with the correct orientation.

Each end of the 76 bp paired reads was aligned separately against the human hg18 reference sequence with Maq using a mismatch threshold of 150. maq.sourceforge.net. If both ends aligned successfully, the resulting pair was added to the interaction catalog. These reads were confirmed to tend to align near HindIII restriction sites with the expected orientation. See FIG. 27A and FIG. 27B.

To produce heatmaps, a genome was divided into 1 Mb loci and/or 100 Kb loci wherein each interaction was binned according to the location of both ends to produce the matrix M. Very few loci were identical at both ends, indicating that the effects of PCR bias are minimal. Alternative alignment strategies were compared of multiple aligners and parameter settings and verified that no substantive differences were observed. A random permutation of one end of the reads, resulted in essentially uniform heatmaps. Reads derived from sheared genomic DNA instead of from a Hi-C library, failed to form any heatmaps capable of analysis as described herein.

Example XVI

Presence of Chromosome Territories

The total number of possible interactions at a given genomic distance was computed explicitly for each chromosome and compared to the actual number of interactions at that distance. The possible number of pairs of genomic positions separated by d on a given chromosome is $L_c$-d, where $L_c$ is the length of the chromosome. To obtain the interchromosomal averages, the number of observed interactions between loci on a pair of chromosomes was divided by the number of possible interactions between the two chromosomes (the product of the number of loci on each chromosome). When multiple chromosome pairings were being averaged, such as in the computation of In(s), the numerators and denominators were summed independently. The genome wide average, I(s), is therefore the result of dividing the total number of interactions at a distance s by the number of possible interactions at distance s summed over all chromosomes.

Example XVII

Proximity of Chromosome Territories

The expected number of interchromosomal interactions for each chromosome pair i,j was computed by multiplying the fraction of interchromosomal reads containing i with the fraction of interchromosomal reads containing j and multiplying by the total number of interchromosomal reads. The enrichment was computed by taking the actual number of interactions observed between i and j and dividing it by the expected value.

Example XVIII

Correlation Analysis

Intrachromosomal

Figure 28:
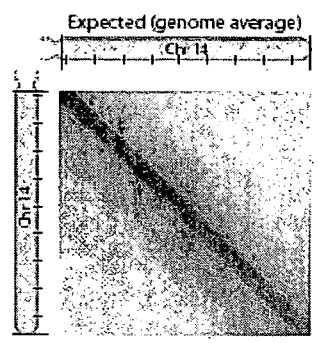
FIG. 28 presents exemplary data showing an expected matrix. The average contact probability for a pair of loci at a given genomic distance produces an expectation matrix corresponding to what would be observed if there were no long-range structure.
Figure 29:
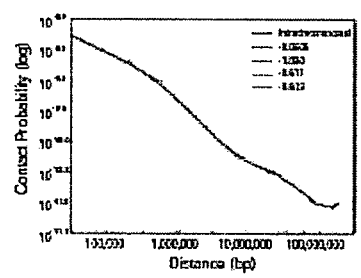
FIG. 29 presents exemplary data showing four distinct scaling regimes for contact probability at varying size scales.

The expected number of reads between two loci i,j was computed by calculating the distance between the midpoints of the two loci s(i,j). This distance was then used as an argument to the function I(s) to compute the expected number of reads between the pair. See, FIG. 28. The entries of the observed/expected matrix M* was computed by taking each $m_{ij}$ and dividing by I(s(i,j)). The corresponding entry of the correlation matrix was computed $c_{ij}$ by taking the observed/expected value for every intrachromosomal locus pair including i ($c_{ix}$) with every interchromosomal locus pair including j ($c_{xj}$) and computing the Pearson correlation coefficient between the two resulting vectors. Superior results at low resolution may be obtained with the Spearman correlation coefficient, but the latter is not suitable for analyzing the sparse matrices which arise at higher resolution (100 Kb).

Interchromosomal

Coverage was normalized, which does not exert a significant effect on intrachromosomal read counts but does exert a significant effect in the interchromosomal case. This was accomplished analogously to the proximity computation for chromosome territories. The expected number of interactions between each locus pair i,j is computed by multiplying the fraction of reads containing i with the fraction of reads containing j and multiplying by the total number of reads. See, FIG. 19G, coverage tracks. The enrichment was computed by taking the actual number of interactions observed between locus i and locus j, $m_{ij}$, and dividing it by this expected value. The correlations are then computed as in the intrachromosomal case, comparing the enrichment values for all interchromosomal locus pairs involving either i or j but excluding any intrachromosomal locus pairs.

Principal Component Analysis

Principal component analysis was performed as previously reported. Price et al., *Nat Genet* 38:904 (2006).

Example IXX

Genomic Tracks

UCSC gene annotations were combined with DNAseI and ChIP-Seq data. Total number of genic bases in a given locus was used in the gene density annotations shown. Raw DNAse data tracks were downloaded from the ENCODE UCSC browser; values within a given megabase or 100 Kb locus was summed to produce the track shown. For ChIP-Seq data, the number of reads in each locus was plotted. Ku et al., *PLoS Genet* 4: e1000242 (October, 2008).

Example XX

Expression Analysis

Expression data for GM and K562 cells were collected with Affymetrix HGU133 2 Plus expression arrays (Affymetrix, Santa Clara, USA). Two experiments were performed for each cell type. Expression data was averaged for all probes lying fully within each 1 Mb locus, including both experiments on the particular cell type. Probes overlapping the edges of the windows were not included in the analysis. Windows were grouped associated with either Compartment A or Compartment B, and computed the distribution of average expression for windows associated with each element type.

Example XXI

Polymer Physics

I(s) was plotted on log-log axes. A theoretical derivation of the scaling for fractal globules and Monte Carlo simulations are described supra. Images were rendered with PyMol. pymol.sourceforge.net.

We claim:

1. A method for identifying interaction frequencies, comprising:
   a) providing;
      i) a nuclear matrix comprising a first genomic region and a second genomic region; and
      ii) a junction marker labeled with an affinity marker for selective purification of a ligation product;
   b) fragmenting said first genomic region and said second genomic region into a plurality of first genomic region fragments and a plurality of second genomic region fragments;
   c) ligating said junction marker between at least one of said first genomic region fragments and at least one of said second genomic region fragments to create said ligation product;
   d) purifying said ligation product with said affinity marker;
   and
   e) analyzing said ligation product under conditions such that a genomic interaction frequency for said ligation product is identified.

2. The method of claim 1, wherein said affinity marker comprises biotin.

3. The method of claim 1, wherein said first and second genomic regions are located on the same chromosome.

4. The method of claim 1, wherein said first and second genomic regions are located on different chromosomes.

5. The method of claim 1, wherein said interaction frequency identifies a long range interaction.

6. The method of claim 1, wherein said interaction frequency identifies a short range interaction.

7. The method of claim 1, wherein said interaction frequency identifies a close neighbor interaction.

8. The method of claim 1, wherein said nuclear matrix is derived from a human cell nucleus.

9. The method of claim 1, wherein said nuclear matrix is derived from a yeast cell nucleus.

10. The method of claim 1, further comprising contacting said junction marker with a ligand.

11. The method of claim 10, wherein said ligand comprises streptavidin.

12. The method of claim 1, further comprising digesting said nuclear matrix fragments with a restriction endonuclease wherein a first region fragment comprising a first sticky end and a second region fragment comprising a second sticky end are created.

13. The method of claim 12, further comprising filling in said first sticky end and said second sticky end to create a first blunt end and a second blunt end; and ligating said first and second blunt ends, wherein said first region fragment and said second region fragment are joined.

14. The method of claim 1, further comprising digesting said nuclear matrix fragments with an exonuclease.

15. A method for identifying interaction frequencies, comprising:
    a) crosslinking a nuclear matrix comprising a first genomic region and a second genomic region;
    b) fragmenting said first genomic region and said second genomic region into a plurality of first genomic region fragments and a plurality of second genomic region fragments;
    c) ligating a junction marker labeled with an affinity marker between at least one of said first genomic region fragments and at least one of said second genomic region fragments to create a ligation product;
    d) purifying said ligation product with said affinity marker;
    and
    e) analyzing said ligation product under conditions such that a genomic interaction frequency for said ligation product is identified.

16. A method for identifying interaction frequencies, comprising:
    a) crosslinking a nuclear matrix comprising a first genomic region and a second genomic region;
    b) fragmenting said first genomic region and said second genomic region into a plurality of first genomic region fragments and a plurality of second genomic region fragments;
    c) ligating a junction marker labeled with an affinity marker between at least one of said first genomic region fragments and at least one of said second genomic region fragments to create a ligation product;
    d) purifying said ligation product with said affinity marker;
    and
    e) detecting a close proximity between said first genomic region and said second genomic region with said ligation product under conditions such that a genomic interaction frequency for said ligation product is identified.

17. A method for identifying interaction frequencies, comprising:
    a) crosslinking a nuclear matrix comprising a first genomic region and a second genomic region;
    b) fragmenting said first genomic region and said second genomic region into a plurality of first genomic region fragments and a plurality of second genomic region fragments;
    c) ligating a junction marker labeled with an affinity marker between at least one of said first genomic region fragments and at least one of said second genomic region fragments to create a ligation product;
    d) purifying said ligation product with said affinity marker;
    and
    e) identifying a contact probability as a function of genomic distance between said first genomic region and said second genomic region with said ligation product under conditions such that a genomic interaction frequency for said ligation product is identified.

18. A method for identifying interaction frequencies, comprising:
    a) crosslinking a nuclear matrix comprising a first genomic region and a second genomic region;
    b) fragmenting said first genomic region and said second genomic region into a plurality of first genomic region fragments and a plurality of second genomic region fragments;
    c) ligating a junction marker labeled with an affinity marker between at least one of said first genomic region fragments and at least one of said second genomic region fragments to create a ligation product;
    d) purifying said ligation product with said affinity marker;
    and
    e) identifying whether said first genomic region and said second genomic region preferentially associate with each other with said ligation product under conditions such that a genomic interaction frequency for said ligation product is identified.

* * * * *

UNITED STATES PATENT AND TRADEMARK OFFICE
CERTIFICATE OF CORRECTION

Page 1 of 1

PATENT NO. : 9,434,985 B2
APPLICATION NO. : 13/121158
DATED : September 6, 2016
INVENTOR(S) : Dekker et al.

It is certified that error appears in the above-identified patent and that said Letters Patent is hereby corrected as shown below:

In the Specification

Under the heading,

FEDERALLY SPONSORED RESEARCH OR DEVELOPMENT

Insert:

--This invention was made with Government support under Grant Nos. HG003143, HHSN266200400001C and U54 HG003067 awarded by the National Institutes of Health. The government has certain rights in the invention.--

Signed and Sealed this
Third Day of January, 2017

Michelle K. Lee
*Director of the United States Patent and Trademark Office*

SEQUENCE LISTING

```
<160> NUMBER OF SEQ ID NOS: 19

<210> SEQ ID NO 1
<211> LENGTH: 31
<212> TYPE: DNA
<213> ORGANISM: Artificial Sequence
<220> FEATURE:
<223> OTHER INFORMATION: Synthetic

<400> SEQUENCE: 1
gttcatcttg ctgccagaaa tgccgagcct g                              31

<210> SEQ ID NO 2
<211> LENGTH: 31
<212> TYPE: DNA
<213> ORGANISM: Artificial Sequence
<220> FEATURE:
<223> OTHER INFORMATION: Synthetic

<400> SEQUENCE: 2
atcccagctg tctgtagctt tagaaagtgg g                              31

<210> SEQ ID NO 3
<211> LENGTH: 30
<212> TYPE: DNA
<213> ORGANISM: Artificial Sequence
<220> FEATURE:
<223> OTHER INFORMATION: Synthetic

<400> SEQUENCE: 3
acctgttgtt taatgaaggg gctcagaagc                                30

<210> SEQ ID NO 4
<211> LENGTH: 30
<212> TYPE: DNA
<213> ORGANISM: Artificial Sequence
<220> FEATURE:
<223> OTHER INFORMATION: Synthetic

<400> SEQUENCE: 4
gtttgcagtg tgctgtgcag catgtgtgta                                30
```

```
<210> SEQ ID NO 5
<211> LENGTH: 6
<212> TYPE: DNA
<213> ORGANISM: Artificial Sequence
<220> FEATURE:
<223> OTHER INFORMATION: Synthetic

<400> SEQUENCE: 5 aagctt                                                                    6

<210> SEQ ID NO 6
<211> LENGTH: 7
<212> TYPE: DNA
<213> ORGANISM: Artificial Sequence
<220> FEATURE:
<223> OTHER INFORMATION: Synthetic

<400> SEQUENCE: 6 aaagctt                                                                   7

<210> SEQ ID NO 7
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: The "T" residue at this position is internally
      biotinylated.

<400> SEQUENCE: 7
gctgcatgat gtactag                                                       17

<210> SEQ ID NO 8
<211> LENGTH: 17
<212> TYPE: DNA
<213> ORGANISM: Artificial Sequence
<220> FEATURE:
<223> OTHER INFORMATION: Synthetic

<400> SEQUENCE: 8
gctctagtac atcatgc                                                       17

<210> SEQ ID NO 9
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: The residue at this position is a biotinylated
      deoxyuracil.

<400> SEQUENCE: 9 aagcnagctt                                                               10

<210> SEQ ID NO 10
<211> LENGTH: 17
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (10)..(10)
<223> OTHER INFORMATION: The residue "T" at this position is internally
      biotinylated.

<400> SEQUENCE: 10
gctgcatgat gtactag                                                      17

<210> SEQ ID NO 11
<211> LENGTH: 17
<212> TYPE: DNA
<213> ORGANISM: Artificial Sequence
<220> FEATURE:
<223> OTHER INFORMATION: Synthetic

<400> SEQUENCE: 11
gctctagtac atcatgc                                                      17

<210> SEQ ID NO 12
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: The residue "T" at this position is internally
      biotinylated.

<400> SEQUENCE: 12
aagctgcatg atgtactaga gctt                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
aagctctagt acatcatgca gctt                                              24

<210> SEQ ID NO 14
<211> LENGTH: 235
<212> TYPE: DNA
<213> ORGANISM: Artificial Sequence
<220> FEATURE:
<223> OTHER INFORMATION: Synthetic

<400> SEQUENCE: 14
cggcccaggg ttcatattaa gaaccaagtt ctgggagaca ctgaggcccc caggggttct        60
ggagtcagca ctaaaccagg cagccctcag gtgaggtctg agagcatctc agaagctcta       120
gtacatcatg cagcttggcc tttcggctca gatctcagcc cacagctggc ctgatctggg       180
tctcccctcc caccctcagg gagccaggct cggcatttct ggcagcaaga tgaac           235

<210> SEQ ID NO 15
<211> LENGTH: 217
<212> TYPE: DNA
<213> ORGANISM: Artificial Sequence
<220> FEATURE:
<223> OTHER INFORMATION: Synthetic
```

```
<400> SEQUENCE: 15
cggcccaggg ttcatattaa gaaccaagtt ctgggagaca ctgaggcccc caggggttct    60
ggagtcagca ctaaaccagg cagccctcag gtgaggtctg agagcatctc agaagcttgg   120
cctttcggct cagatctcag cccacagctg gcctgatctg ggtctcccct cccaccctca   180
gggagccagg ctcgccattt ctggcagcaa gatgaac                            217

<210> SEQ ID NO 16
<211> LENGTH: 35
<212> TYPE: DNA
<213> ORGANISM: Artificial Sequence
<220> FEATURE:
<223> OTHER INFORMATION: Synthetic

<400> SEQUENCE: 16
gctgcatgat gtactagagc tgcatgatgt actag                               35

<210> SEQ ID NO 17
<211> LENGTH: 35
<212> TYPE: DNA
<213> ORGANISM: Artificial Sequence
<220> FEATURE:
<223> OTHER INFORMATION: Synthetic

<400> SEQUENCE: 17
cgtactacat gatctcgacg tactacatga tctcg                               35

<210> SEQ ID NO 18
<211> LENGTH: 60
<212> TYPE: DNA
<213> ORGANISM: Artificial Sequence
<220> FEATURE:
<223> OTHER INFORMATION: Synthetic

<400> SEQUENCE: 18
aagctctagt acatcatgca gctgcatgat gtactagagc tctagtacat catgcagctt    60

<210> SEQ ID NO 19
<211> LENGTH: 42
<212> TYPE: DNA
<213> ORGANISM: Artificial Sequence
<220> FEATURE:
<223> OTHER INFORMATION: Synthetic

<400> SEQUENCE: 19
aagctctagt acatcatgca gctgcatgat gtactagagc tt                       42
```